(12) United States Patent
Heemstra et al.

(10) Patent No.: US 10,590,120 B2
(45) Date of Patent: Mar. 17, 2020

(54) PESTICIDAL COMPOSITIONS AND METHODS

(71) Applicant: Dow AgroSciences LLC, Indianapolis, IN (US)

(72) Inventors: Ronald J. Heemstra, Fishers, IN (US); Gary D. Crouse, Noblesville, IN (US); Thomas C. Sparks, Greenfield, IN (US); Natalie C. Giampietro, Carmel, IN (US); David A. Demeter, Fishers, IN (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 5 days.

(21) Appl. No.: 15/724,454

(22) Filed: Oct. 4, 2017

(65) Prior Publication Data
US 2018/0099958 A1    Apr. 12, 2018

Related U.S. Application Data

(60) Provisional application No. 62/405,315, filed on Oct. 7, 2016.

(51) Int. Cl.
| | | |
|---|---|---|
| *C07D 417/12* | (2006.01) |
| *A01N 43/78* | (2006.01) |
| *A01N 47/36* | (2006.01) |

(52) U.S. Cl.
CPC ........... *C07D 417/12* (2013.01); *A01N 43/78* (2013.01); *A01N 47/36* (2013.01)

(58) Field of Classification Search
USPC ........................................................ 504/358
See application file for complete search history.

(56) References Cited

U.S. PATENT DOCUMENTS

2012/0322660 A1* 12/2012 Beghyn ............ C07K 14/43563
504/319

* cited by examiner

*Primary Examiner* — Ali Soroush
*Assistant Examiner* — Courtney A Brown

(57) ABSTRACT

This disclosure relates to the field of molecules having pesticidal utility against pests in phyla Nematoda, Arthropoda, and/or Mollusca, processes to produce such molecules and intermediates used in such processes, compositions containing such molecules, and processes of using such molecules against such pests. These molecules may be used, for example, as nematicides, acaricides, insecticides, miticides, and/or molluscicides. This document discloses molecules having the structure of Formula A.

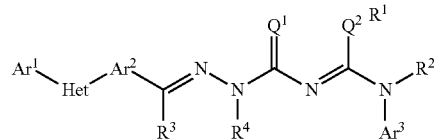

17 Claims, No Drawings

PESTICIDAL COMPOSITIONS AND METHODS

CROSS REFERENCES TO RELATED APPLICATIONS

This application claims priority under 35 U.S.C. § 119 of U.S. provisional patent application Ser. No. 62/405,315 filed Oct. 7, 2016, which application is hereby incorporated by reference in its entirety.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

SUMMARY OF THE INVENTION

In one aspect, provided are molecules having the structure of Formula A:

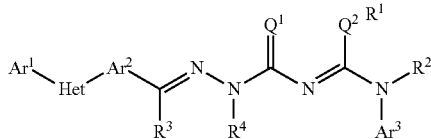

Formula A wherein:
(A) $Ar^1$ is selected from
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, and substituted thienyl have one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(O)NR^xR^y$, $(C_1$-$C_8$ alkyl)$NR^xR^y$, $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(O)(C_1$-$C_8$ alkyl), $C_1$-$C_8$ alkyl)phenyl, $C_1$-$C_8$ alkyl)-O-phenyl, phenyl, phenoxy, $Si(C_1$-$C_8$ alkyl)$_3$, or $S(=O)_n$ $NR^xR^y$, or (Het-1),
    wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(O)NR^xR^y$, $(C_1$-$C_8$ alkyl)$NR^xR^y$, $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(O)(C_1$-$C_8$ alkyl)$C(=O)O(C_1$-$C_8$ alkyl), $(C_1$-$C_8$ alkyl)$C(=O)OC_1$-$C_8$ alkyl), $(C_1$-$C_8$ alkyl)$C(O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_n$ $NR^xR^y$, or (Het-1);

(B) Het is a 5- or 6-membered, saturated or unsaturated, heterocyclic ring, containing one or more heteroatoms independently selected from nitrogen, sulfur, or oxygen, and where $Ar^1$ and $Ar^2$ are not ortho to each other (but may be meta or para, such as, for a five-membered ring they are 1,3 and for a 6-membered ring they are either 1,3 or 1,4) and where said heterocyclic ring may also be substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(O)NR^xR^y$, $(C_1$-$C_8$ alkyl)$NR^xR^y$, $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n$ ($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, or S(=O)$_n$NR$^x$R$^y$, wherein each alkyl, haloalkyl, cycloalkyl, halocycloalkyl, alkoxy, haloalkoxy, alkenyl, cycloalkenyl, haloalkenyl, alkynyl, phenyl, and phenoxy substituent may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S($C_1$-$C_8$ alkyl), S($C_3$-$C_8$ cycloalkyl), S($C_1$-$C_8$ haloalkyl), S($C_3$-$C_8$ halocycloalkyl), S(O)$_n$($C_1$-$C_8$ alkyl), S(O)$_n$($C_1$-$C_8$ haloalkyl), OSO$_2$($C_1$-$C_8$ alkyl), OSO$_2$($C_1$-$C_8$ haloalkyl), C(O)NR$^x$R$^y$, ($C_1$-$C_8$ alkyl)NR$^x$R$^y$, C(O)($C_1$-$C_8$ alkyl), C(=O)O($C_1$-$C_8$ alkyl), C(O)($C_1$-$C_8$ haloalkyl), C(=O)O($C_1$-$C_8$ haloalkyl), C(O)($C_3$-$C_8$ cycloalkyl), C(=O)O($C_3$-$C_8$ cycloalkyl), C(O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S($C_1$-$C_8$ alkyl), ($C_1$-$C_8$ alkyl)S(O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, or S(=O)$_n$NR$^x$R$^y$;

(C) Ar$^2$ is selected from
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, and substituted thienyl, have one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S($C_1$-$C_8$ alkyl), S($C_3$-$C_8$ cycloalkyl), S($C_1$-$C_8$ haloalkyl), S($C_3$-$C_8$ halocycloalkyl), S(O)$_n$($C_1$-$C_8$ alkyl), S(O)$_n$($C_1$-$C_8$ haloalkyl), OSO$_2$($C_1$-$C_8$ alkyl), OSO$_2$($C_1$-$C_8$ haloalkyl), C(O)NR$^x$R$^y$, ($C_1$-$C_8$ alkyl)NR$^x$R$^y$, C(O)($C_1$-$C_8$ alkyl), C(=O)O($C_1$-$C_8$ alkyl), C(O)($C_1$-$C_8$ haloalkyl), C(=O)O($C_1$-$C_8$ haloalkyl), C(O)($C_3$-$C_8$ cycloalkyl), C(=O)O($C_3$-$C_8$ cycloalkyl), C(O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S($C_1$-$C_8$ alkyl), ($C_1$-$C_8$ alkyl)S(O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1),
      wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) substituent may be optionally substituted with one or more substituents independently selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S($C_1$-$C_8$ alkyl), S($C_3$-$C_8$ cycloalkyl), S($C_1$-$C_8$ haloalkyl), S($C_3$-$C_8$ halocycloalkyl), S(O)$_n$($C_1$-$C_8$ alkyl), S(O)$_n$($C_1$-$C_8$ haloalkyl), OSO$_2$($C_1$-$C_8$ alkyl), OSO$_2$($C_1$-$C_8$ haloalkyl), C(O)NR$^x$R$^y$, ($C_1$-$C_8$ alkyl)NR$^x$R$^y$, C(O)($C_1$-$C_8$ alkyl), C(=O)O($C_1$-$C_8$ alkyl), C(O)($C_1$-$C_8$ haloalkyl), C(=O)O($C_1$-$C_8$ haloalkyl), C(O)($C_3$-$C_8$ cycloalkyl), C(=O)O($C_3$-$C_8$ cycloalkyl), C(O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S($C_1$-$C_8$ alkyl), ($C_1$-$C_8$ alkyl)S(O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(O)($C_1$-$C_8$ alkyl), ($C_1$-$C_8$ alkyl)phenyl, ($C_1$-$C_8$ alkyl)-O-phenyl, phenyl, phenoxy, Si($C_1$-$C_8$ alkyl)$_3$, S(=O)$_n$NR$^x$R$^y$, or (Het-1);

(D) L$^1$ is linker selected from
  (1) a saturated, substituted or unsubstituted, one carbon linker,
  (2) a saturated or unsaturated, substituted or unsubstituted, linear $C_2$-$C_4$ hydrocarbyl linker, or
  (3) a saturated or unsaturated, substituted or unsubstituted, cyclic $C_3$-$C_8$ hydrocarbyl group linker,
    wherein said substituted one carbon linker, substituted linear $C_2$-$C_4$ hydrocarbyl linker, and substituted cyclic $C_3$-$C_8$ hydrocarbyl linker has one or more substituents independently selected from R$^3$, R$^4$, R$^5$, R$^6$, and R$^7$, wherein each R$^3$, R$^4$, R$^5$, R$^6$, and R$^7$ is selected from H, F, Cl, Br, I, CN, OH, SH, NO$_2$, oxo, thioxo, NR$^x$R$^y$, $C_1$-$C_8$ alkyl, $C_1$-$C_8$ haloalkyl, $C_1$-$C_8$ alkoxy, $C_1$-$C_8$ haloalkoxy, $C_2$-$C_8$ alkenyl, $C_2$-$C_8$ haloalkenyl, $C_2$-$C_8$ alkynyl, $C_2$-$C_8$ haloalkynyl, $C_3$-$C_8$ cycloalkyl, $C_3$-$C_8$ halocycloalkyl, $C_3$-$C_8$ cycloalkenyl, $C_3$-$C_8$ halocycloalkenyl, S($C_1$-$C_8$ alkyl), S($C_3$-$C_8$ cycloalkyl), S($C_1$-$C_8$ haloalkyl), S($C_3$-$C_8$ halocycloalkyl), phenyl, or phenoxy;

(E) Q$^1$ is selected from O or S;
(F) Q$^2$ is selected from O or S;
(G) R$^1$ is selected from (J), H, $C_1$-$C_8$ alkyl, $C_3$-$C_8$ cycloalkyl, $C_2$-$C_8$ alkenyl, $C_2$-$C_8$ alkynyl, C(O)($C_1$-$C_8$ alkyl), ($C_1$-$C_8$ alkyl)O($C_1$-$C_8$ alkyl), ($C_1$-$C_8$ alkyl)S($C_1$-$C_8$ alkyl), ($C_1$-$C_8$ alkyl)S(O)$_n$($C_1$-$C_8$ alkyl), ($C_1$-$C_8$ alkyl)phenyl, ($C_1$-$C_8$ alkyl)-O-phenyl, C(O)(Het-1), (Het-1), ($C_1$-$C_8$ alkyl)-(Het-1), ($C_1$-$C_8$ alkyl)-C(O)—($C_1$-$C_8$ alkyl), ($C_1$-$C_8$ alkyl)-OC(=O)—($C_1$-$C_8$ alkyl), ($C_1$-$C_8$ alkyl)-O—C(=O)O—($C_1$-$C_8$ alkyl), ($C_1$-$C_8$ alkyl)-O—C(O)NR$^x$R$^y$, ($C_1$-$C_8$ alkyl)-C(O)N(R$^x$)($C_1$-$C_8$ alkyl)-(Het-1), ($C_1$-$C_8$ alkyl)-C(=O)(Het-1), ($C_1$-$C_8$ alkyl)-C(O)N(R$^x$)($C_1$-$C_8$ alkyl)N(R$^y$)C(=O)OH, ($C_1$-$C_8$ alkyl)-C(O)N(R$^x$)($C_1$-$C_8$ alkyl)N(R$^x$)(R$^y$), ($C_1$-$C_8$ alkyl)-C(O)N(R$^x$)($C_1$-$C_8$ alkyl)N(R$^y$)C(=O)O—($C_1$-$C_8$ alkyl), ($C_1$-$C_8$ alkyl)-C(O)N(R$^x$)($C_1$-$C_8$ alkyl)(N(R$^y$)C(=O)O—($C_1$-$C_8$ alkyl)C(=O)OH, ($C_1$-$C_8$ alkyl)-C(O)(Het-1)C(=O)O—($C_1$-$C_8$ alkyl), ($C_1$-$C_8$ alkyl)-OC(=O)O—($C_1$-$C_8$ alkyl), ($C_1$-$C_8$ alkyl)-OC(=O)—($C_1$-$C_8$ alkyl), ($C_1$-$C_8$ alkyl)-OC(=O)—($C_3$-$C_8$ cycloalkyl), ($C_1$-$C_8$ alkyl)-OC(O)-(Het-1), ($C_1$-$C_8$ alkyl)-OC(=O)—($C_1$-$C_8$ alkyl)N(R$^x$)C(=O)O—($C_1$-$C_8$ alkyl), ($C_1$-$C_8$ alkyl)-NR$^x$R$^y$, ($C_1$-$C_8$ alkyl)-S-(Het-1), ($C_1$-$C_8$ alkyl)S(O)$_n$(Het-1), or ($C_1$-$C_8$ alkyl)-O-(Het-1), wherein each alkyl, cycloalkyl, phenyl, and (Het-1) are optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(=O)H$, $C(=O)OH$, $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(O)(C_1$-$C_8$ alkyl), $(C_1$-$C_8$ alkyl)phenyl, $(C_1$-$C_8$ alkyl)-O-phenyl, phenyl, phenoxy, $Si(C_1$-$C_8$ alkyl)$_3$, $S(=O)_nNR^xR^y$, or (Het-1);

(H) $R^2$ is selected from (J), H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(O)H$, $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(O)(C_1$-$C_8$ alkyl), $(C_1$-$C_8$ alkyl)phenyl, $(C_1$-$C_8$ alkyl)-O-phenyl, phenyl, $(C_1$-$C_8$ alkyl)phenyl, $(C_1$-$C_8$ alkyl)-O-phenyl, $C(O)(Het-1)$, (Het-1), $(C_1$-$C_8$ alkyl)-(Het-1), $(C_1$-$C_8$ alkyl)-$C(O)$—$(C_1$-$C_8$ alkyl), $(C_1$-$C_8$ alkyl)-O—$(C_1$-$C_8$ alkyl), $(C_1$-$C_8$ alkyl)-OC$(=O)$—$(C_1$-$C_8$ alkyl), $(C_1$-$C_8$ alkyl)-O—$C(O)NR^xR^y$, $(C_1$-$C_8$ alkyl)-$C(O)N(R^x)(C_1$-$C_8$ alkyl)-(Het-1), $(C_1$-$C_8$ alkyl)-$C(=O)(Het-1)$, $(C_1$-$C_8$ alkyl)-$C(O)N(R^x)(C_1$-$C_8$ alkyl)$N(R^y)C(=O)OH$, $(C_1$-$C_8$ alkyl)-$C(O)N(R^x)(C_1$-$C_8$ alkyl)$N(R^x)(R^y)$, $(C_1$-$C_8$ alkyl)-$C(O)N(R^x)(C_1$-$C_8$ alkyl)$N(R^y)C(=O)$—$(C_1$-$C_8$ alkyl), $(C_1$-$C_8$ alkyl)-$C(O)N(R^x)(C_1$-$C_8$ alkyl)$(N(R^y)C(=O)O$—$(C_1$-$C_8$ alkyl)$C(=O)OH$, $(C_1$-$C_8$ alkyl)-$C(O)(Het-1)C(=O)O$—$(C_1$-$C_8$ alkyl), $(C_1$-$C_8$ alkyl)-$OC(=O)O$—$(C_1$-$C_8$ alkyl), $(C_1$-$C_8$ alkyl)-$OC(=O)$—$(C_1$-$C_8$ alkyl), $(C_1$-$C_8$ alkyl)-$OC(=O)$—$(C_3$-$C_8$ cycloalkyl), $(C_1$-$C_8$ alkyl)-$OC(O)$-(Het-1), $(C_1$-$C_8$ alkyl)-$OC(=O)$—$(C_1$-$C_8$ alkyl)$N(R^x)C(=O)O$—$(C_1$-$C_8$ alkyl), $(C_1$-$C_8$ alkyl)-$NR^xR^y$, $(C_1$-$C_8$ alkyl)-S-(Het-1), $(C_1$-$C_8$ alkyl)$S(O)_n$(Het-1), or $(C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(=O)H$, $C(=O)OH$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(O)(C_1$-$C_8$ alkyl), $(C_1$-$C_8$ alkyl)phenyl, $(C_1$-$C_8$ alkyl)-O-phenyl, phenyl, halophenyl, phenoxy, and (Het-1);

(I) Each of $R^3$ and $R^4$ is independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(=O)NR^xR^y$, $C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(O)(C_1$-$C_8$ alkyl), $C_1$-$C_8$ alkyl)phenyl, and $C_1$-$C_8$ alkyl)-O-phenyl, phenyl, phenoxy, $Si(C_1$-$C_8$ alkyl)$_3$, $S(=O)_nNR^xR^y$, or (Het-1), wherein each alkyl, haloalkyl, cycloalkyl, halocycloalkyl, alkoxy, haloalkoxy, alkenyl, cycloalkenyl, haloalkenyl, alkynyl, phenyl, phenoxy, and (Het-1) may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(=O)NR^xR^y$, $(C_1$-$C_8$ alkyl)$NR^xR^y$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)$O(C_1$-$C_8$ alkyl), $(C_1$-$C_8$ alkyl)$S(C_1$-$C_8$ alkyl), $(C_1$-$C_8$ alkyl)$S(O)_n(C_1$-$C_8$ alkyl), $(C_1$-$C_8$ alkyl)$OC(=O)(C_1$-$C_8$ alkyl), $(C_1$-$C_8$ alkyl)$OC(=O)O(C_1$-$C_8$ alkyl), $C(=O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(O)(C_1$-$C_8$ alkyl), $(C_1$-$C_8$ alkyl)phenyl, and $(C_1$-$C_8$ alkyl)-O-phenyl, phenyl, phenoxy, $Si(C_1$-$C_8$ alkyl)$_3$, $S(=O)_nNR^xR^y$, or (Het-1);

(J) $R^1$ and $R^2$ may be a 1- to 4-membered saturated or unsaturated, hydrocarbyl link, which may contain one or more heteroatoms selected from nitrogen, sulfur, and oxygen, and together with (Q²)(C)(N) forms a 4- to 7-membered cyclic structure, wherein said hydrocarbyl link may optionally be substituted with one or more substituents independently selected from $R^5$, $R^6$, and $R^7$, wherein each $R^5$, $R^6$, and $R^7$ is selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), C(O)H, $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)O$(C_1$-$C_8$ alkyl), $(C_1$-$C_8$ alkyl)S$(C_1$-$C_8$ alkyl), $(C_1$-$C_8$ alkyl)S(O)$_n$ $(C_1$-$C_8$ alkyl), $(C_1$-$C_8$ alkyl)OC(=O)$(C_1$-$C_8$ alkyl), $(C_1$-$C_8$ alkyl)OC(=O)O$(C_1$-$C_8$ alkyl), $C(O)(C_1$-$C_8$ alkyl)C (=O)O$(C_1$-$C_8$ alkyl), $(C_1$-$C_8$ alkyl)C(=O)O$(C_1$-$C_8$ alkyl), $(C_1$-$C_8$ alkyl)C(O)$(C_1$-$C_8$ alkyl), $(C_1$-$C_8$ alkyl)phenyl, $(C_1$-$C_8$ alkyl)-O-phenyl, phenyl, substituted phenyl, phenoxy, or (Het-1);

(K) $Ar^3$ is selected from $C_3$-$C_8$ cycloalkyl, phenyl, $(C_1$-$C_8$ alkyl)phenyl, $(C_1$-$C_8$ alkyl)-O-phenyl, $(C_2$-$C_8$ alkenyl)-O-phenyl, (Het-1), $(C_1$-$C_8$ alkyl)-(Het-1), $(C_1$-$C_8$ alkyl)-O-(Het-1), wherein the $C_3$-$C_8$ cycloalkyl, phenyl, $(C_1$-$C_8$ alkyl)phenyl, $(C_1$-$C_8$ alkyl)-O-phenyl, $(C_2$-$C_8$ alkenyl)-O-phenyl, (Het-1), $(C_1$-$C_8$ alkyl)-(Het-1), or $(C_1$-$C_8$ alkyl)-O-(Het-1) may be optionally substituted with one or more substituents independently selected from H, F, Cl, Br, I, CN, OH, SH, $NO_2$, oxo, thioxo, $NR^xR^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n$ $(C_1$-$C_8$ haloalkyl), $OSO_2(C_1$-$C_8$ alkyl), $OSO_2(C_1$-$C_8$ haloalkyl), $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)O$(C_1$-$C_8$ alkyl), $(C_1$-$C_8$ alkyl)S$(C_1$-$C_8$ alkyl), $(C_1$-$C_8$ alkyl)S(O)$_n$$(C_1$-$C_8$ alkyl), $(C_1$-$C_8$ alkyl)OC (=O)$(C_1$-$C_8$ alkyl), $(C_1$-$C_8$ alkyl)OC(=O)O$(C_1$-$C_8$ alkyl), $C(O)(C_1$-$C_8$ alkyl)C(=O)O$(C_1$-$C_8$ alkyl), $(C_1$-$C_8$ alkyl)C(=O)O$(C_1$-$C_8$ alkyl), $(C_1$-$C_8$ alkyl)C(O) $(C_1$-$C_8$ alkyl), $(C_1$-$C_8$ alkyl)phenyl, $(C_1$-$C_8$ alkyl)-O-phenyl, phenyl, phenoxy, Si$(C_1$-$C_8$ alkyl)$_3$, $S(=O)_n$ $NR^xR^y$, or (Het-1);

(L) $R^x$ and $R^y$ are independently selected from H, OH, SH, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), C(O)H, $C(O)(C_1$-$C_8$ alkyl), $C(=O)O(C_1$-$C_8$ alkyl), $C(O)(C_1$-$C_8$ haloalkyl), $C(=O)O(C_1$-$C_8$ haloalkyl), $C(O)(C_3$-$C_8$ cycloalkyl), $C(=O)O(C_3$-$C_8$ cycloalkyl), $C(O)(C_2$-$C_8$ alkenyl), $C(=O)O(C_2$-$C_8$ alkenyl), $(C_1$-$C_8$ alkyl)O$(C_1$-$C_8$ alkyl), $(C_1$-$C_8$ alkyl)S$(C_1$-$C_8$ alkyl), $(C_1$-$C_8$ alkyl)S(O)$_n$$(C_1$-$C_8$ alkyl), $(C_1$-$C_8$ alkyl)OC (=O)$(C_1$-$C_8$ alkyl), $C(O)(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)$C(=O)O(C_1$-$C_8$ alkyl), $(C_1$-$C_8$ alkyl)phenyl, $(C_1$-$C_8$ alkyl)-O-phenyl, phenyl, $(C_1$-$C_8$ alkyl)phenyl, $(C_1$-$C_8$ alkyl)-O-phenyl, C(O) (Het-1), (Het-1), $(C_1$-$C_8$ alkyl)-(Het-1), $(C_1$-$C_8$ alkyl)-C (O)—$(C_1$-$C_8$ alkyl), $(C_1$-$C_8$ alkyl)-OC(=O)—$(C_1$-$C_8$ alkyl), $(C_1$-$C_8$ alkyl)-O—C(=O)O—$(C_1$-$C_8$ alkyl), $(C_1$-$C_8$ alkyl)-C(=O)(Het-1), $(C_1$-$C_8$ alkyl)-C(O)(Het-1)C (=O)O—$(C_1$-$C_8$ alkyl), $(C_1$-$C_8$ alkyl)-OC(=O)O—$(C_1$-$C_8$ alkyl), $(C_1$-$C_8$ alkyl)-OC(=O)—$(C_1$-$C_8$ alkyl), $(C_1$-$C_8$ alkyl)-OC(=O)—$(C_3$-$C_8$ cycloalkyl), $(C_1$-$C_8$ alkyl)-OC (O)-(Het-1), $(C_1$-$C_8$ alkyl)-S-(Het-1), $(C_1$-$C_8$ alkyl)S(O)$_n$ (Het-1), or $(C_1$-$C_8$ alkyl)-O-(Het-1), wherein each alkyl, haloalkyl, cycloalkyl, halocycloalkyl, cycloalkoxy, halocycloalkoxy, alkoxy, haloalkoxy, alkenyl, cycloalkenyl, haloalkenyl, alkynyl, phenyl, and (Het-1), are optionally substituted with one or more substituents independently selected from H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n$ $(C_1$-$C_8$ haloalkyl), $OSO_2(C_1$-$C_8$ alkyl), $OSO_2(C_1$-$C_8$ haloalkyl), $C(=O)H$, $C(=O)OH$, $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O $(C_1$-$C_8$ alkyl), $(C_1$-$C_8$ alkyl)S$(C_1$-$C_8$ alkyl), $(C_1$-$C_8$ alkyl)S(O)$_n$$(C_1$-$C_8$ alkyl), $(C_1$-$C_8$ alkyl)OC(=O)$(C_1$-$C_8$ alkyl), $(C_1$-$C_8$ alkyl)OC(=O)O$(C_1$-$C_8$ alkyl), $C(=O)(C_1$-$C_8$ alkyl)C(=O)O$(C_1$-$C_8$ alkyl), $(C_1$-$C_8$ alkyl)C(=O)O$(C_1$-$C_8$ alkyl), $(C_1$-$C_8$ alkyl)C(O)$(C_1$-$C_8$ alkyl), $(C_1$-$C_8$ alkyl)phenyl, $(C_1$-$C_8$ alkyl)-O-phenyl, phenyl, halophenyl, phenoxy, and (Het-1), or $R^x$ and $R^y$ together can optionally form a 5- to 7-membered saturated or unsaturated cyclic group which may contain one or more heteroatoms selected from nitrogen, sulfur, and oxygen, and where said cyclic group may be substituted with H, F, Cl, Br, I, CN, OH, SH, $NO_2$, oxo, thioxo, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, $S(C_1$-$C_8$ alkyl), $S(C_3$-$C_8$ cycloalkyl), $S(C_1$-$C_8$ haloalkyl), $S(C_3$-$C_8$ halocycloalkyl), $S(O)_n(C_1$-$C_8$ alkyl), $S(O)_n(C_1$-$C_8$ haloalkyl), $OSO_2(C_1$-$C_8$ alkyl), $OSO_2(C_1$-$C_8$ haloalkyl), $C(=O)(C_1$-$C_8$ alkyl), $C(=O)O(C_1$-$C_8$ alkyl), $C(=O)(C_1$-$C_8$ haloalkyl), $C(=O)O(C_1$-$C_8$ haloalkyl), $C(=O)(C_3$-$C_8$ cycloalkyl), $C(=O)O(C_3$-$C_8$ cycloalkyl), $C(=O)(C_2$-$C_8$ alkenyl), $C(=O)O(C_2$-$C_8$ alkenyl), $(C_1$-$C_8$ alkyl)O $(C_1$-$C_8$ alkyl), $(C_1$-$C_8$ alkyl)S$(C_1$-$C_8$ alkyl), $(C_1$-$C_8$ alkyl)S(O)$_n$$(C_1$-$C_8$ alkyl), $(C_1$-$C_8$ alkyl)OC(=O)$(C_1$-$C_8$ alkyl), $(C_1$-$C_8$ alkyl)OC(=O)O$(C_1$-$C_8$ alkyl), $C(=O)(C_1$-$C_8$ alkyl)C(=O)O$(C_1$-$C_8$ alkyl), $(C_1$-$C_8$ alkyl)C(=O)O$(C_1$-$C_8$ alkyl), $(C_1$-$C_8$ alkyl)C(O)$(C_1$-$C_8$ alkyl), $(C_1$-$C_8$ alkyl)phenyl, $(C_1$-$C_8$ alkyl)-O-phenyl, phenyl, substituted phenyl, phenoxy, and (Het-1);

(M) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, OH, SH, NO₂, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S($C_1$-$C_8$ alkyl), S($C_3$-$C_8$ cycloalkyl), S($C_1$-$C_8$ haloalkyl), S($C_3$-$C_8$ halocycloalkyl), S(O)$_n$($C_1$-$C_8$ alkyl), S(O)$_n$($C_1$-$C_8$ haloalkyl), OSO₂($C_1$-$C_8$ alkyl), OSO₂($C_1$-$C_8$ haloalkyl), C(O)NR$^x$R$^y$, ($C_1$-$C_8$ alkyl)NR$^x$R$^y$, C(O)($C_1$-$C_8$ alkyl), C(=O)O($C_1$-$C_8$ alkyl), C(O)($C_1$-$C_8$ haloalkyl), C(=O)O($C_1$-$C_8$ haloalkyl), C(O)($C_3$-$C_8$ cycloalkyl), C(=O)O($C_3$-$C_8$ cycloalkyl), C(O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S($C_1$-$C_8$ alkyl), ($C_1$-$C_8$ alkyl)S(O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(O)($C_1$-$C_8$ alkyl), ($C_1$-$C_8$ alkyl)phenyl, ($C_1$-$C_8$ alkyl)-O-phenyl, phenyl, and phenoxy, wherein each alkyl, cycloalkyl, alkoxy, alkenyl, alkynyl, phenyl, and phenoxy may be optionally substituted with one or more substituents independently selected from H, F, Cl, Br, I, CN, OH, SH, NO₂, oxo, thioxo, NR$^x$R$^y$, $C_1$-$C_8$ alkyl, $C_1$-$C_8$ haloalkyl, $C_3$-$C_8$ cycloalkyl, $C_3$-$C_8$ halocycloalkyl, $C_3$-$C_8$ cycloalkoxy, $C_3$-$C_8$ halocycloalkoxy, $C_1$-$C_8$ alkoxy, $C_1$-$C_8$ haloalkoxy, $C_2$-$C_8$ alkenyl, $C_3$-$C_8$ cycloalkenyl, $C_2$-$C_8$ haloalkenyl, $C_2$-$C_8$ alkynyl, S($C_1$-$C_8$ alkyl), S($C_3$-$C_8$ cycloalkyl), S($C_1$-$C_8$ haloalkyl), S($C_3$-$C_8$ halocycloalkyl), S(O)$_n$($C_1$-$C_8$ alkyl), S(O)$_n$($C_1$-$C_8$ haloalkyl), OSO₂($C_1$-$C_8$ alkyl), OSO₂($C_1$-$C_8$ haloalkyl), C(=O)H, C(O)NR$^x$R$^y$, ($C_1$-$C_8$ alkyl)NR$^x$R$^y$, C(O)($C_1$-$C_8$ alkyl), C(=O)O($C_1$-$C_8$ alkyl), C(O)($C_1$-$C_8$ haloalkyl), C(=O)O($C_1$-$C_8$ haloalkyl), C(O)($C_3$-$C_8$ cycloalkyl), C(=O)O($C_3$-$C_8$ cycloalkyl), C(O)($C_2$-$C_8$ alkenyl), C(=O)O($C_2$-$C_8$ alkenyl), ($C_1$-$C_8$ alkyl)O($C_1$-$C_8$ alkyl), ($C_1$-$C_8$ alkyl)S($C_1$-$C_8$ alkyl), ($C_1$-$C_8$ alkyl)S(O)$_n$($C_1$-$C_8$ alkyl), ($C_1$-$C_8$ alkyl)OC(=O)($C_1$-$C_8$ alkyl), ($C_1$-$C_8$ alkyl)OC(=O)O($C_1$-$C_8$ alkyl), C(O)($C_1$-$C_8$ alkyl)C(=O)O($C_1$-$C_8$ alkyl), ($C_1$-$C_8$ alkyl)C(=O)O($C_1$-$C_8$ alkyl), ($C_1$-$C_8$ alkyl)C(O)($C_1$-$C_8$ alkyl), ($C_1$-$C_8$ alkyl)phenyl, ($C_1$-$C_8$ alkyl)-O-phenyl, phenyl, and phenoxy; and (N) n is each individually 0, 1, or 2.

In another embodiment, Het and L¹ are not ortho to each other, but may be meta or para, such as, for a five membered ring they are 1,3, and for a 6 membered ring they are either 1,3 or 1,4.

In another embodiment, the molecules provided have the structure of Formula One:

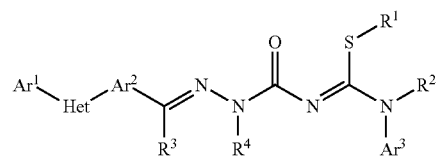

Formula One wherein:

(a) Ar¹ is a phenyl or substituted phenyl having one or more substituents independently selected from $C_1$-$C_6$ alkyl, $C_1$-$C_6$ haloalkyl, and $C_1$-$C_6$ haloalkoxy;

(b) Het is a triazolyl, imidazolyl, pyrrolyl, or pyrazolyl;

(c) Ar² is a phenyl or a substituted phenyl having one or more substituents independently selected from $C_1$-$C_6$ alkyl, $C_1$-$C_6$ haloalkyl, and $C_1$-$C_6$ haloalkoxy;

(d) R³ and R⁴ are each independently selected from H, F, Cl, $C_1$-$C_6$ alkyl, $C_1$-$C_6$ alkoxy, $C_1$-$C_6$ haloalkyl, $C_1$-$C_6$ haloalkoxy, phenyl, or phenoxy;

R¹ and R² together form a 5- to 7-membered ring containing one or more C=O, C=S, N, S or O, and such ring is optionally substituted with OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, phenyl, or phenoxy, wherein said phenyl or phenoxy is optionally substituted with one or more OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, or phenyl; and (e) Ar³ is a phenyl optionally substituted with one or more substituents independently selected from OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, phenyl, or phenoxy.

In one embodiment, Ar¹ is a substituted phenyl having one or more substituents independently selected from OCF₃, OCF₂CF₃, and CF₃. In another embodiment, Het is a 1,2,4-triazolyl. In another embodiment, Ar² is a phenyl.

In another embodiment, R¹ and R² together form a 5-membered ring containing one or two C=O, and such ring is optionally substituted with OH, F, Cl, Br, I, CN, $C_1$-$C_6$ alkyl, $C_1$-$C_6$ haloalkyl, $C_1$-$C_6$ alkoxy, $C_1$-$C_6$ haloalkoxy, phenyl or phenoxy. In another embodiment, each of R³ and R⁴ is independently H, F, Cl, or a $C_1$-$C_6$ alkyl. In another embodiment, Ar³ is a substituted phenyl with one or more substituents independently selected from OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, or $C_1$-$C_6$ haloalkoxy.

In another embodiment, the molecule has a structure selected from compounds listed in Table 1:

A1

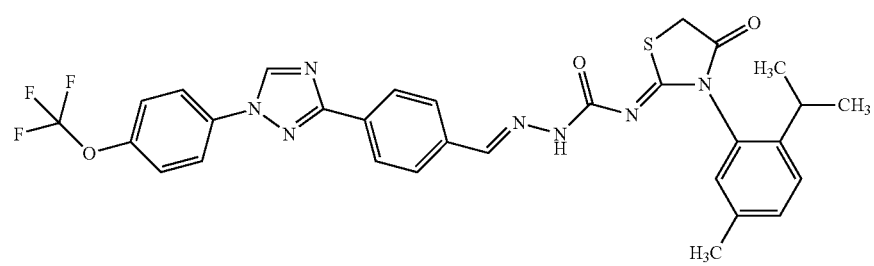 [SMILES: Cc1ccc(C(C)C)c(N2C(=O)CS/C2=N\C(=O)N/N=C/c2ccc(-c3ncn(-c4ccc(OC(F)(F)F)cc4)n3)cc2)c1]

-continued
A2
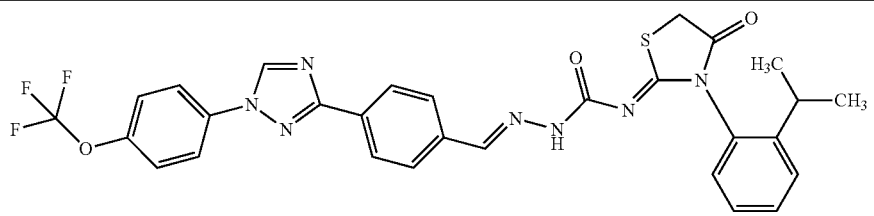
A3
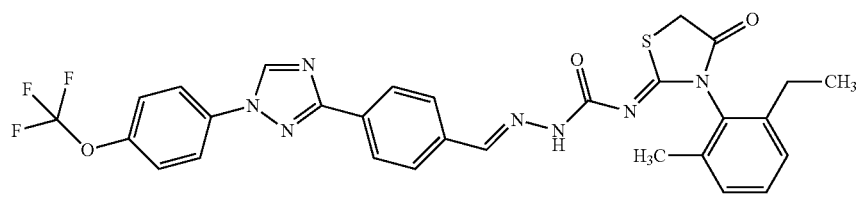 [SMILES: CCc1cccc(C)c1N1C(=O)CS/C1=N\C(=O)N/N=C/c1ccc(-c2ncn(-c3ccc(OC(F)(F)F)cc3)n2)cc1]
A4
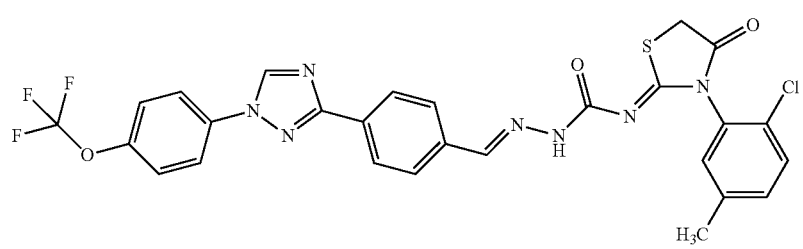 [SMILES: Cc1ccc(Cl)c(N2C(=O)CS/C2=N\C(=O)N/N=C/c2ccc(-c3ncn(-c4ccc(OC(F)(F)F)cc4)n3)cc2)c1]
A5
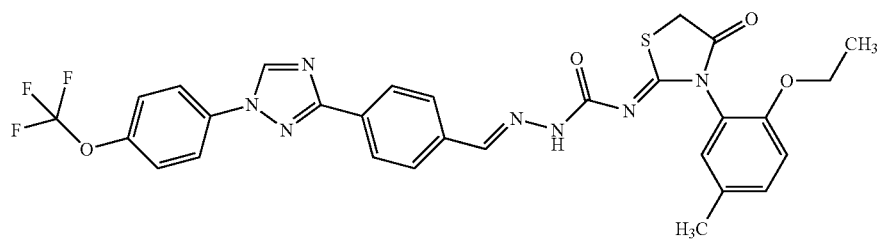 [SMILES: CCOc1ccc(C)cc1N1C(=O)CS/C1=N\C(=O)N/N=C/c1ccc(-c2ncn(-c3ccc(OC(F)(F)F)cc3)n2)cc1]
A6
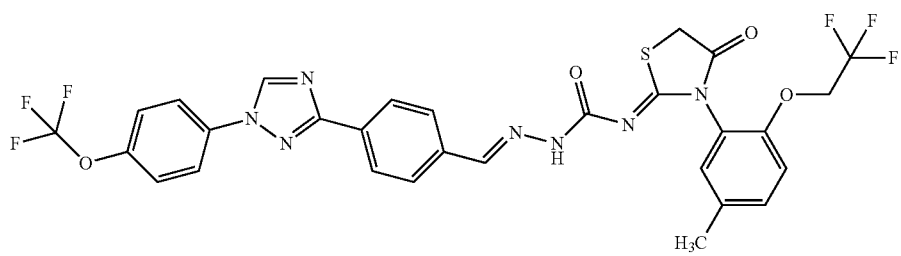 [SMILES: Cc1ccc(OCC(F)(F)F)c(N2C(=O)CS/C2=N\C(=O)N/N=C/c2ccc(-c3ncn(-c4ccc(OC(F)(F)F)cc4)n3)cc2)c1]
A7
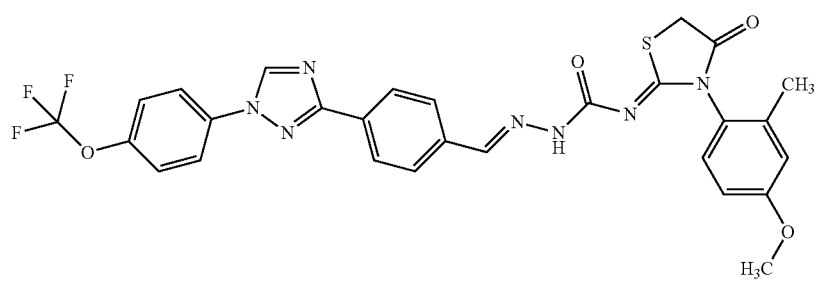 [SMILES: COc1ccc(N2C(=O)CS/C2=N\C(=O)N/N=C/c2ccc(-c3ncn(-c4ccc(OC(F)(F)F)cc4)n3)cc2)c(C)c1]
A8
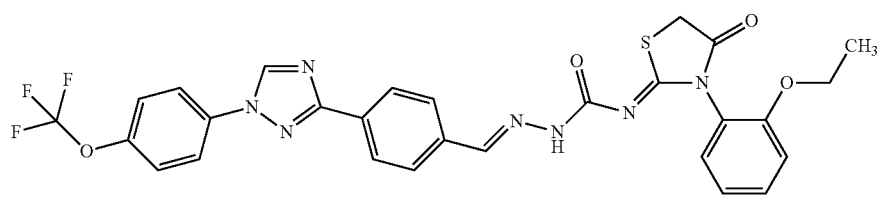 [SMILES: CCOc1ccccc1N1C(=O)CS/C1=N\C(=O)N/N=C/c1ccc(-c2ncn(-c3ccc(OC(F)(F)F)cc3)n2)cc1]

A9

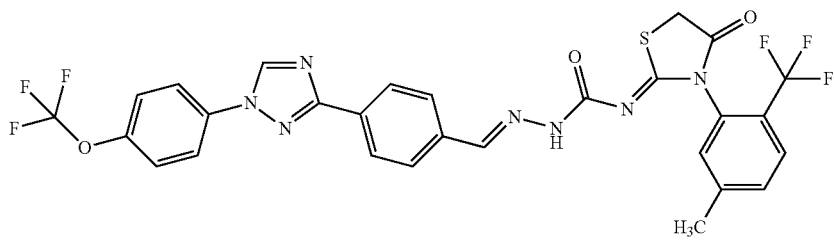 [SMILES: Cc1ccc(C(F)(F)F)c(N2C(=O)CS/C2=N\C(=O)N/N=C/c2ccc(-c3ncn(-c4ccc(OC(F)(F)F)cc4)n3)cc2)c1]

In another aspect, provided is a process to apply a molecule provided herein. The process comprises applying a molecule provided herein, to an area to control a pest, in an amount sufficient to control such pest. In one embodiment, the pest is beet armyworm (BAW), corn earworm (CEW), or green peach aphid (GPA).

In another aspect, provided is a molecule that is a pesticidally acceptable acid addition salt, a salt derivative, a solvate, or an ester derivative, of a molecule provided herein. In another aspect, provided is a molecule provided herein wherein at least one H is $^2$H or at least one C is $^{14}$C. In another aspect, provided is a composition comprising a compound provided herein and at least one other compound having insecticidal, herbicidal, acaricidal, nematicidal, or fungicidal activity. In another aspect, provided is a composition comprising a molecule provided herein and a seed.

In another aspect, provided is a process comprising applying a molecule provided herein to a genetically modified plant or a genetically-modified seed, which has been genetically modified to express one or more specialized traits. In another aspect, provided is a process comprising: orally administering or topically applying a molecule provided herein, to a non-human animal, to control endoparasites, ectoparasites, or both.

DETAILED DESCRIPTION OF THE INVENTION

The examples given for the substituents are (except for halo) non-exhaustive and must not be construed as limiting the invention disclosed in this document.

Definitions

"Alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"Alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"Alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"Alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"Alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"Alkynyloxy" means an alkynyl further consisting of a carbon-oxygen single bond, for example, pentynyloxy, hexynyloxy, heptynyloxy, octynyloxy, nonynyloxy, and decynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"Halo" means fluoro, chloro, bromo, and iodo.

"Haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

Compounds

The compounds of this invention have the structure of Formula One:

Formula One

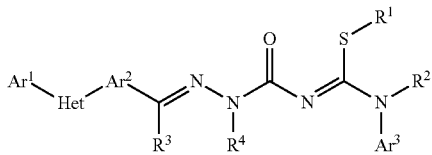

wherein:
(a) $Ar^1$ is selected from
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
  wherein said substituted furanyl, substituted phenyl, substituted pyridazinyl, substituted pyridyl, substituted pyrimidinyl, and substituted thienyl have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl, and substituted phenoxy,
    wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl) phenyl, and phenoxy;

(b) Het is a 5- or 6-membered, saturated or unsaturated, heterocyclic ring, containing one or more heteroatoms independently selected from nitrogen, sulfur, or oxygen, and where $Ar^1$ and $Ar^2$ are not ortho to each other (but may be meta or para, such as, for a five-membered ring they are 1,3 and for a 6-membered ring they are either 1,3 or 1,4), and where said heterocyclic ring may also be substituted with one or more substituents independently selected from H, F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), phenyl, phenoxy, substituted phenyl and substituted phenoxy,
  wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(c) $Ar^2$ is selected from
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
  wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy,
    wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR^xR^y$, $(C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy);

(d) $R^1$, $R^2$, $R^3$, and $R^4$ are each independently selected from H, F, Cl, $C_1$-$C_6$ alkyl, $C_3$-$C_6$ cycloalkyl, $C_3$-$C_6$ cycloalkoxy, $C_1$-$C_6$ alkoxy, $C_1$-$C_6$ haloalkyl, $C_1$-$C_6$ haloalkoxy, $C_2$-$C_6$ alkenyl, $C_2$-$C_6$ alkynyl, ($C_1$-$C_6$ alkyl)$NR^xR^y$, $C(=O)(C_1$-$C_6$ alkyl), $C(=O)O(C_1$-$C_6$ alkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, or phenoxy, wherein each alkyl, haloalkyl, hydroxyalkyl, cycloalkyl, cycloalkoxy, alkoxy, alkenyl, alkynyl, phenyl, and phenoxy are optionally substituted with one or more substituents independently selected from OH, F, Cl, Br, I, CN, $NO_2$, oxo, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR^xR^y$, ($C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

wherein $R^1$ and $R^2$ together can optionally form a 5- to 7-membered ring containing one or more C=O, C=S, N, S or O, and such ring is optionally substituted with OH, F, Cl, Br, I, CN, $NO_2$, $NR^xR^y$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), C(=O)H, C(=O)OH, $C(=O)NR^xR^y$, ($C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, or Het-1, wherein Het-1 is a 5- or 6-membered, saturated or unsaturated, heterocyclic ring, containing one or more heteroatoms independently selected from nitrogen, sulfur and oxygen, wherein said phenyl, phenoxy, or Het-1 is optionally substituted with one or more OH, F, Cl, Br, I, CN, $NO_2$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_3$-$C_6$ cycloalkoxy, $C_3$-$C_6$ halocycloalkoxy, $C_3$-$C_6$ hydroxycycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), C(=O)H, C(=O)OH, $C(=O)NR^xR^y$, ($C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), C(=O)($C_1$-$C_6$ alkyl)$C(=O)O(C_1$-$C_6$ alkyl) or phenyl, wherein $R^x$ and $R^y$ are independently selected from H, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ hydroxycycloalkyl, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), C(=O)H, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), ($C_1$-$C_6$ alkyl)$O(C_1$-$C_6$ alkyl), ($C_1$-$C_6$ alkyl)$S(C_1$-$C_6$ alkyl), $C(=O)(C_1$-$C_6$ alkyl)$C(=O)O(C_1$-$C_6$ alkyl), or phenyl; and (e) $Ar^3$ is a phenyl or Het-1;

wherein the phenyl or Het-1 is optionally substituted with one or more substituents independently selected from OH, F, Cl, Br, I, CN, $NO_2$, $NR^xR^y$, $C_1$-$C_6$ alkyl, $C_1$-$C_6$ haloalkyl, $C_1$-$C_6$ hydroxyalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $C_3$-$C_6$ cycloalkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), C(=O)H, $C(=O)NR^xR^y$, ($C_1$-$C_6$ alkyl)$NR^xR^y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $O(C_1$-$C_6$ alkyl), $S(C_1$-$C_6$ alkyl), $C(=O)(C_1$-$C_6$ alkyl)$C(=O)O(C_1$-$C_6$ alkyl), phenyl, or phenoxy.

In one embodiment, $Ar^1$ is a phenyl or substituted phenyl having one or more substituents independently selected from $C_1$-$C_6$ alkyl, $C_1$-$C_6$ haloalkyl, and $C_1$-$C_6$ haloalkoxy.

In another embodiment, Het is a triazolyl, imidazolyl, pyrrolyl, or pyrazolyl.

In another embodiment, $Ar^2$ is a phenyl or a substituted phenyl having one or more substituents independently selected from $C_1$-$C_6$ alkyl, $C_1$-$C_6$ haloalkyl, and $C_1$-$C_6$ haloalkoxy.

In another embodiment, $R^1$, $R^2$, $R^3$, and $R^4$ are each independently selected from H, F, Cl, $C_1$-$C_6$ alkyl, $C_1$-$C_6$ alkoxy, $C_1$-$C_6$ haloalkyl, $C_1$-$C_6$ haloalkoxy, phenyl, or phenoxy;

wherein $R^1$ and $R^2$ together can optionally form a 5- to 7-membered ring and is optionally substituted with OH, F, Cl, Br, I, CN, $NO_2$, $C_1$-$C_6$ alkyl, $C_1$-$C_6$ alkoxy, $C_1$-$C_6$ haloalkyl, $C_1$-$C_6$ haloalkoxy, phenyl, phenoxy, or Het-1, wherein Het-1 is a 5- or 6-membered, saturated or unsaturated, heterocyclic ring, containing one or more heteroatoms independently selected from nitrogen, sulfur and oxygen.

In another embodiment, $R^1$ and $R^2$ together form a 5- to 7-membered ring containing one or more C=O, C=S, N, S or O, and such ring is optionally substituted with OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, phenyl, or phenoxy, wherein said phenyl or phenoxy is optionally substituted with one or more OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, or phenyl.

In another embodiment, R' and $R^2$ together form a 5- to 7-membered ring which contains one or more C=O, C=S, N, S or O.

In another embodiment, $Ar^3$ is a phenyl optionally substituted with one or more substituents independently selected from OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, phenyl, or phenoxy.

In another embodiment, $Ar^1$ is a substituted phenyl having one or more substituents independently selected from $OCF_3$, $OCF_2CF_3$, and $CF_3$.

In another embodiment, Het is a substituted pyrazolyl wherein said substituted pyrazolyl has one or more substituents independently selected from H, C(=O)O($C_1$-$C_6$ alkyl), or C(=O)$NR^xR^y$.

In another embodiment, Het is 1,2,4-triazolyl.

In another embodiment, $Ar^2$ is a phenyl.

In another embodiment, $Ar^2$ is a substituted phenyl having one or more substituents independently selected from $OCF_3$, $OCF_2CF_3$, and $CF_3$.

In another embodiment, $R^1$ is H or a $C_1$-$C_6$ alkyl.
In another embodiment, $R^2$ is H or a $C_1$-$C_6$ alkyl.
In another embodiment, $R^3$ is H, F, Cl, or a $C_1$-$C_6$ alkyl.
In another embodiment, $R^3$ is H or a $C_1$-$C_6$ alkyl.
In another embodiment, $R^4$ is H, F, Cl, or a $C_1$-$C_6$ alkyl.
In another embodiment, $R^4$ is H or a $C_1$-$C_6$ alkyl.
In another embodiment, each of $R^1$ and $R^2$ is independently H or a $C_1$-$C_6$ alkyl.
In another embodiment, each of $R^3$ and $R^4$ is independently H, F, Cl, or a $C_1$-$C_6$ alkyl.
In another embodiment, $R^1$ and $R^2$ together form a 5-membered ring containing one or two C=O, and such ring is optionally substituted with OH, F, Cl, Br, I, CN, $C_1$-$C_6$ alkyl, $C_1$-$C_6$ haloalkyl, $C_1$-$C_6$ alkoxy, $C_1$-$C_6$ haloalkoxy, phenyl or phenoxy.

In another embodiment, $Ar^3$ is a substituted phenyl with one or more OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, or $C_1$-$C_6$ haloalkoxy.

In another embodiment, $Ar^3$ is a substituted phenyl having one or more substituents independently selected from $OCF_3$, $OCF_2CF_3$, and $CF_3$.

In another embodiment, the molecule has a structure selected from compounds listed in Table 1 below:

TABLE 1

Structures for Compounds

A1
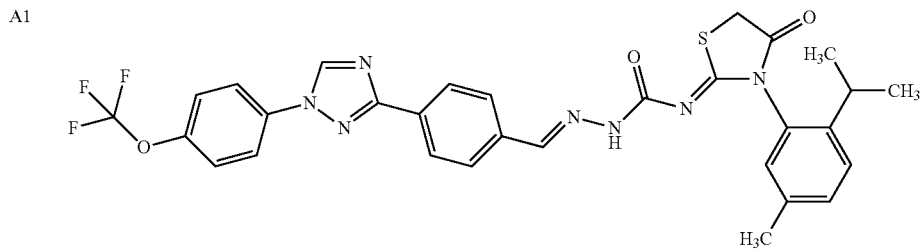

A2
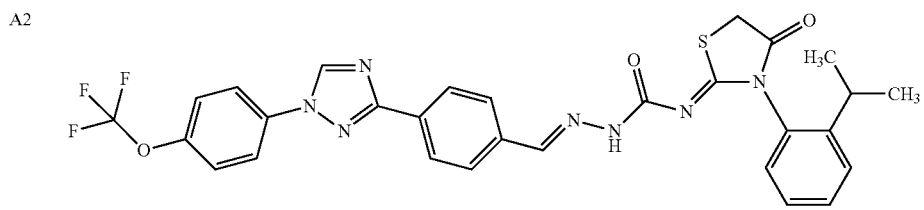

A3
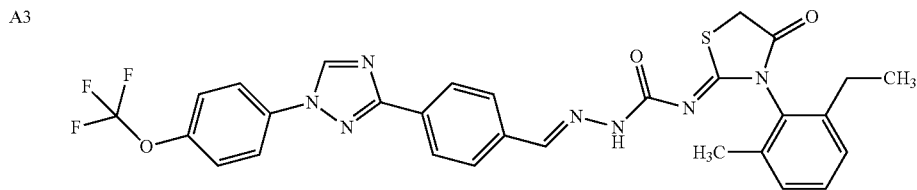

A4
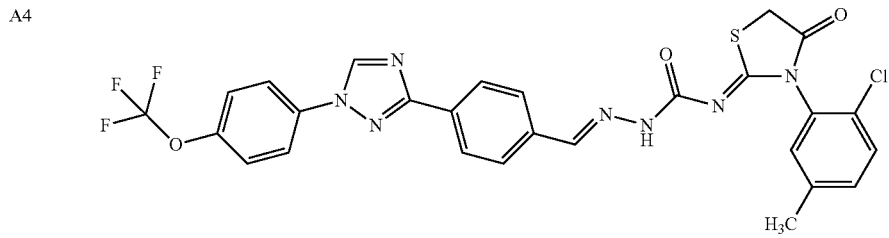

TABLE 1-continued

Structures for Compounds

A5

A6

A7

A8

A9

Preparation of Triaryl Hydrazone Ureas

Triaryl hydrazone ureas 1-4, wherein Het, $Ar^1$, $Ar^2$, $Ar^3$, $R^1$, $R^2$, $R^3$, and $R^4$ are as previously disclosed, can be prepared by treating a triaryl hydrazone 1-2, wherein Het, $Ar^1$, $Ar^2$, $R^3$, and $R^4$ are as previously disclosed, with p-nitrophenyl carbamate in a polar solvent, such as acetonitrile, and in the presence of a base, such as cesium carbonate, to form an activated intermediate in situ which is subsequently reacted with a cyclic thiourea 1-3, wherein $Ar^3$, $R^1$, and $R^2$ are as previously disclosed (Scheme 1, step b).

Hydrazones 1-2 wherein Het, $Ar^1$, $Ar^2$, $R^3$, and $R^4$ are as previously disclosed may be prepared by condensing a triaryl aldehyde or ketone 1-1 wherein Het, $Ar^1$, $Ar^2$, and $R^3$ are as previously disclosed with hydrazine hydrate or a substituted hydrazine in refluxing ethanol (Scheme 1, step a). Triaryl intermediates 1-1 can be prepared by methods previously described in the chemical literature. Several of these methods are described below.

Intermediates wherein 'Het' is a disubstituted pyridine, pyrimidine, pyrazine or pyridizine can be made by coupling of a halo- or alkylthio-substituted pyridine, pyrimidine or pyrazine with an aryl boronic acid or borate ester, under Suzuki arylation conditions. See, for example, the following.

For pyridines: Couve-Bonnaire et al. *Tetrahedron* 2003, 59, 2793 and Puglisi et al. *Eur. J. Org. Chem.* 2003, 1552.

For pyrazines: Schultheiss and Bosch *Heterocycles* 2003, 60, 1891.

For pyrimidines: Qing et al. *J. Fluorine Chem.* 2003, 120, 21 and Ceide and Montalban *Tetrahedron Lett.* 2006, 47, 4415.

For 2,4-diaryl pyrimidines: Schomaker and Delia, *J. Org. Chem.* 2001, 66, 7125.

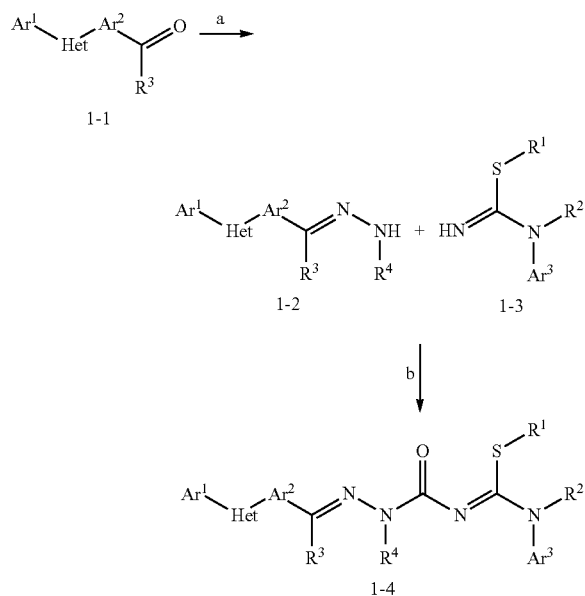

Scheme 1

Acid and Salt Derivatives and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous sodium hydroxide (NaOH), potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well-known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass *Ataenius*), *Atomaria linearis* (pygmy mangold beetle), *Aulacophora* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (housefly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape *phylloxera*), *Physokermes piceae* (spruce bud scale), *Planococcus* spp. (mealybugs), *Pseudococcus* spp. (mealybugs), *Pseudococcus brevipes* (pineapple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonic* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruit tree leafroller), *Archips rosana* (rose leaf roller), *Argyrotaenia* spp. (tortricid moths), *Argyrotaenia citrana* (orange tortrix), *Autographa gamma*, *Bonagota cranaodes*, *Borbo cinnara* (rice leaf folder), *Bucculatrix thurberiella* (cotton leaf perforator), *Caloptilia* spp. (leaf miners), *Capua reticulana*, *Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella*, *Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea grandiosella* (southwestern corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant tortrix), *Pandemis heparana* (brown apple tortrix), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarpa*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria*, *Melanoplus* spp. (grasshoppers), *Microcentrum retinerve* (angular winged katydid), *Pterophylla* spp. (katydids), *chistocerca gregaria*, *Scudderia furcata* (fork tailed bush katydid), and *Valanga nigricorni*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (*thrips*). A non-exhaustive list of these pests includes, but is not limited to, *Frankliniella fusca* (tobacco *thrips*), *Frankliniella occidentalis* (western flower *thrips*), *Frankliniella shultzei Frankliniella williamsi* (corn *thrips*), *Heliothrips haemorrhaidalis* (greenhouse *thrips*), *Riphiphorothrips cruentatus, Scirtothrips* spp., *Scirtothrips citri* (citrus *thrips*), *Scirtothrips dorsalis* (yellow tea *thrips*), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (two-spotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

Mixtures

The invention disclosed in this document can also be used with various insecticides, both for reasons of economy and synergy. Such insecticides include, but are not limited to, antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, fumigant insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

Some of the particular insecticides that can be employed beneficially in combination with the invention disclosed in this document include, but are not limited to, the following 1,2-dichloropropane, 1,3-dichloropropene, abamectin, acephate, acetamiprid, acethion, acetoprole, acrinathrin, acrylonitrile, acynonapyr, afidopyropen, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, benzpyrimoxan, bifenthrin, bioallethrin, bioethanomethrin, biopermethrin, bioresmethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chloroprallethrin, chlorphoxim, chlorprazophos, chlorpyrifos, chlorpyrifos-methyl, chlorthiophos, chromafenozide, cinerin I, cinerin II, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cyfluthrin, cyhalothrin, cyhalodiamide, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, epsilon-metofluthrin, epsilon-momfluorothrin, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, fluazaindolizine, flubendiamide, flucofuron, flucycloxuron, flucythrinate, flufenerim, flufenoxuron, flufenprox, flufiprole, fluhexafon, flupyradifurone, flupyrimin, fluvalinate, fluxametamide, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methylchloroform, methylene chloride, metofluthrin, metolcarb, metoxadiazone, mevinphos, mexacarbate, milbemectin, milbemycin oxime, mipafox, mirex, momfluorothrin, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spiropidion, spirotetramat, sulcofuron, sulfoxaflor, sulfluramid, sulfotep, sulfuryl fluoride, sulprofos, taufluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, tetraniliprole, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, tyclopyrazoflor, vamidothion, vaniliprole, XMC, xylylcarb, zeta-cypermethrin, zolaprofos, and α-ecdysone.

Additionally, any combination of the above insecticides can be used.

The invention disclosed in this document can also be used, for reasons of economy and synergy, with acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides (these categories not necessarily mutually exclusive).

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs).

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one nonionic lipophilic surface-active agent, (2) at least one nonionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, nonionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Nonionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are nonionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often nonionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV (ultra low volume) formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

Applications

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by any pest, for example, vegetable crops, fruit and nut trees, grapevines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur. Generally, pest populations, activity, or both are desirably reduced more than fifty percent, preferably more than 90 percent.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping. Compounds are applied in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

Combinations

In another embodiment of this invention, molecules of Formula A/Formula One may be used in combination (such as, in a compositional mixture, or a simultaneous or sequential application) with one or more active ingredients.

In another embodiment of this invention, molecules of Formula A/Formula One may be used in combination (such as, in a compositional mixture, or a simultaneous or sequential application) with one or more active ingredients each having a MoA that is the same as, similar to, but more likely—different from, the MoA of the molecules of Formula A/Formula One.

In another embodiment, molecules of Formula A/Formula One may be used in combination (such as, in a compositional mixture, or a simultaneous or sequential application) with one or more molecules having acaricidal, algicidal, avicidal, bactericidal, fungicidal, herbicidal, insecticidal, molluscicidal, nematicidal, rodenticidal, and/or virucidal properties.

In another embodiment, the molecules of Formula A/Formula One may be used in combination (such as, in a compositional mixture, or a simultaneous or sequential application) with one or more molecules that are antifeedants, bird repellents, chemosterilants, herbicide safeners, insect attractants, insect repellents, mammal repellents, mating disrupters, plant activators, plant growth regulators, and/or synergists.

In another embodiment, molecules of Formula A/Formula One may also be used in combination (such as in a compositional mixture, or a simultaneous or sequential application) with one or more biopesticides.

In another embodiment, in a pesticidal composition combinations of a molecule of Formula A/Formula One and an active ingredient may be used in a wide variety of weight ratios. For example, in a two-component mixture, the weight ratio of a molecule of Formula A/Formula One to an active ingredient, the weight ratios in Table A may be used. However, in general, weight ratios less than about 10:1 to about 1:10 are preferred. It is also preferred sometimes to use a three, four, five, six, seven, or more, component mixture comprising a molecule of Formula A/Formula One and an additional two or more active ingredients.

TABLE A

| Weight Ratios Molecule of the Formula A/Formula One:active ingredient |
|---|
| 100:1 to 1:100 |
| 50:1 to 1:50 |
| 20:1 to 1:20 |
| 10:1 to 1:10 |
| 5:1 to 1:5 |
| 3:1 to 1:3 |
| 2:1 to 1:2 |
| 1:1 |

Weight ratios of a molecule of Formula A/Formula One to an active ingredient may also be depicted as X:Y; wherein X is the parts by weight of a molecule of Formula A/Formula One and Y is the parts by weight of active ingredient. The numerical range of the parts by weight for X is $0<X\leq100$ and the parts by weight for Y is $0<Y\leq100$ and is shown graphically in Table B. By way of non-limiting example, the weight ratio of a molecule of Formula A/Formula One to an active ingredient may be 20:1.

Ranges of weight ratios of a molecule of Formula A/Formula One to an active ingredient may be depicted as $X_1:Y_1$ to $X_2:Y_2$, wherein X and Y are defined as above.

In one embodiment, the range of weight ratios may be $X_1:Y_1$ to $X_2:Y_2$, wherein $X_1>Y_1$ and $X_2<Y_2$. By way of non-limiting example, the range of a weight ratio of a molecule of Formula A/Formula One to an active ingredient may be between 3:1 and 1:3, inclusive of the endpoints.

In another embodiment, the range of weight ratios may be $X_1:Y_1$ to $X_2:Y_2$, wherein $X_1>Y_1$ and $X_2>Y_2$. By way of non-limiting example, the range of weight ratio of a molecule of Formula A/Formula One to an active ingredient may be between 15:1 and 3:1, inclusive of the endpoints.

In another embodiment, the range of weight ratios may be $X_1:Y_1$ to $X_2:Y_2$, wherein $X_1<Y_1$ and $X_2<Y_2$. By way of non-limiting example, the range of weight ratios of a molecule of Formula A/Formula One to an active ingredient may be between about 1:3 and about 1:20, inclusive of the endpoints.

It is envisioned that certain weight ratios of a molecule of Formula A/Formula One to an active ingredient, as presented in Table A and B, may be synergistic.

TABLE B

| active ingredient (Y) Parts by weight | 1 | 2 | 3 | 5 | 10 | 15 | 20 | 50 | 100 |
|---|---|---|---|---|---|---|---|---|---|
| 100 | X, Y |  | X, Y |  | X, Y |  |  |  |  |
| 50 | X, Y | X, Y | X, Y |  | X, Y | X, Y |  |  |  |
| 20 | X, Y |  | X, Y | X, Y | X, Y |  | X, Y |  |  |
| 15 | X, Y | X, Y |  |  |  |  | X, Y | X, Y | X, Y |
| 10 | X, Y |  | X, Y |  |  |  |  |  |  |
| 5 | X, Y | X, Y | X, Y |  |  | X, Y |  |  |  |
| 3 | X, Y | X, Y |  | X, Y | X, Y |  | X, Y | X, Y | X, Y |
| 2 | X, Y |  | X, Y | X, Y |  | X, Y |  | X, Y |  |
| 1 | X, Y | X, Y | X, Y | X, Y | X, Y | X, Y | X, Y | X, Y | X, Y | molecule of Formula A/Formula One (X) Parts by weight

Compounds of the present invention may also be useful for increasing vigor of a crop plant. This method comprises contacting the crop plant (e.g., foliage, flowers, fruit or roots) or the seed from which the crop plant is grown with a compound of Formula A/Formula One in amount sufficient to achieve the desired plant vigor effect (i.e. biologically effective amount). Typically the compound of Formula A/Formula One is applied in a formulated composition. Although the compound of Formula A/Formula One is often applied directly to the crop plant or its seed, it can also be applied to the locus of the crop plant, i.e. the environment of the crop plant, particularly the portion of the environment in close enough proximity to allow the compound of Formula A/Formula One to migrate to the crop plant. The locus relevant to this method most commonly comprises the growth medium (i.e. medium providing nutrients to the plant), typically soil in which the plant is grown. Treatment of a crop plant to increase vigor of the crop plant thus comprises contacting the crop plant, the seed from which the crop plant is grown or the locus of the crop plant with a biologically effective amount of a compound of Formula A/Formula One.

Increased crop vigor can result in one or more of the following observed effects: (a) optimal crop establishment as demonstrated by excellent seed germination, crop emergence and crop stand; (b) enhanced crop growth as demonstrated by rapid and robust leaf growth (e.g., measured by leaf area index), plant height, number of tillers (e.g., for rice), root mass and overall dry weight of vegetative mass of the crop; (c) improved crop yields, as demonstrated by time to flowering, duration of flowering, number of flowers, total biomass accumulation (i.e. yield quantity) and/or fruit or grain grade marketability of produce (i.e. yield quality); (d) enhanced ability of the crop to withstand or prevent plant disease infections and arthropod, nematode or mollusk pest infestations; and (e) increased ability of the crop to withstand environmental stresses such as exposure to thermal extremes, suboptimal moisture or phytotoxic chemicals.

The compounds of the present invention can increase the vigor of treated plants compared to untreated plants by killing or otherwise preventing feeding of phytophagous invertebrate pests in the environment of the plants. In the absence of such control of phytophagous invertebrate pests, the pests reduce plant vigor by consuming plant tissues or sap, or transmiting plant pathogens such as viruses. Even in the absence of phytophagous invertebrate pests, the compounds of the invention may increase plant vigor by modifying metabolism of plants. Generally, the vigor of a crop plant will be most significantly increased by treating the plant with a compound of the invention if the plant is grown in a nonideal environment, i.e. an environment comprising one or more aspects adverse to the plant achieving the full genetic potential it would exhibit in an ideal environment.

Of note is the present method for increasing vigor of a crop plant wherein the crop plant is grown in an environment comprising phytophagous invertebrate pests. Also of note is the present method for increasing vigor of a crop plant wherein the crop plant is grown in an environment not comprising phytophagous invertebrate pests. Also of note is the present method for increasing vigor of a crop plant wherein the crop plant is grown in an environment comprising an amount of moisture less than ideal for supporting growth of the crop plant. Of note is the present method for increasing vigor of a crop plant wherein the crop is rice. Also of note is the present method for increasing vigor of a crop plant wherein the crop is maize (corn). Also of note is the present method for increasing vigor of a crop plant wherein the crop is soybean.

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula A/Formula One, at least one additional component selected from the group consisting of surfactants, solid diluents and liquid diluents, and at least one additional biologically active compound or agent. For mixtures of the present invention, the other biologically active compounds or agents can be for together with the present compounds, including the compounds of Formula A/Formula One, to form a premix, or the other biologically active compounds or agents can be formulated separately from the present compounds, including the compounds of Formula A/Formula One, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, acynonapyr, afidopyropen ([(3S,4R,4aR,6S,6aS,12R,12aS,12bS)-3-[cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11H-naphtho[2,1-b]pyrano[3,4-e]pyran-4-yl]methyl cyclopropanecarboxylate), amidoflumet, amitraz, avermectin, azadirachtin, azinphos-methyl, benfuracarb, bensultap, benzpyrimoxan, bifenthrin, bifenazate, bistrifluron, borate, buprofezin, cadusafos, carbaryl, carbofuran, cartap, carzol, chlorantraniliprole, chiorfenapyr, chlorfluazuron, chlorpyrifos, chlorpyrifos-methyl, chromafenozide, clofentezin, clothianidin, cyantraniliprole (3-bromo-1-(3-chloro-2-pyridinyl)-N-[4-cyano-2-methyl-6-[methylamino)carbonyl]phenyl]-1H-pyrazole-5-carboxamide), cyclaniliprole (3-bromo-N-[2-bromo-4-chloro-6-[[(1-cyclopropylethyl)amino]carbonyl]phenyl]-1-(3-chloro-2-pyridinyl)-1-H-pyrazole-5-carboxamide), cycloprothrin, cycloxaprid ((5S,8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flometoquin (2-ethyl-3,7-dimethyl-6-[4-(trifluoromethoxy)phenoxy]-4-quinolinyl methyl carbonate), flonicamid, fluazaindolizine, flubendiamide, flucythrinate, flufenerim, flufenoxuron, flufenoxystrobin (methyl (αE)-2-[[2-chloro-4-(trifluoromethyl)phenoxy]methyl]-α-(methoxymethylene)benzeneacetate), fluensulfone (5-chloro-2-[(3,4,4-trifluoro-3-buten-1-yl)sulfonyl]thiazole), fluhexafon, fluopyram, flufiprole (1-[2,6-dichloro-4-(trifluoromethyl)phenyl]-5-[(2-methyl-2-propen-1-yl)amino]-4-[(trifluoromethyl)sulfinyl]-1H-pyrazole-3-carbonitrile), flupyradifurone (4-[[(6-chloro-3-pyridinyl)methyl](2,2-difluoroethyl)amino]-2(5H)-furanone), flypyrimin, fluvalinate, tau-fluvalinate, fonophos, formetanate, fosthiazate, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclopropanecarboxylate), hexaflumuron, hexythiazox, hydramethylnon, imidacloprid, indoxacarb, insecticidal soaps, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methiocarb, methomyl, methoprene, methoxychlor, methoxyfenozide, metofluthrin, monocrotophos, monofluorothrin ([2,3,5,6-tetrafluoro-4-(methoxymethyl)phenyl]methyl 3-(2-cyano-1-propen-1-yl)-2,2-dimethylcyclopropanecarboxylate), nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pyflubumide (1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide), pymetrozine, pyrafluprole, pyrethrin, pyridaben, pyridalyl, pyrifluquinazon, pyriminostrobin (methyl (αE)-2-[[[2-[(2,4-dichlorophenyl)amino]-6-(trifluoromethyl)-4-pyrimidinyl]oxy]methyl]-α-(methoxymethylene)benzeneacetate), pyriprole, pyriproxyfen, rotenone, ryanodine, silafluofen, spinetoram, spinosad, spirodiclofen, spirodion, spiromesifen, spirotetramat, sulprofos, sulfoxaflor (N-[methyloxido[1-[6-(trifluoromethyl)-3-pyridinyl]ethyl]-λ$^4$-sulfanylidene]cyanamide), tebufenozide, tebufenpyrad, teflubenzuron, tefluthrin, terbufos, tetrachlorvinphos, tetramethrin, tetramethylfluthrin ([2,3,5,6-tetrafluoro-4-(methoxymethyl)phenyl]methyl 2,2,3,3-tetramethylcyclopropanecarboxylate), tetraniliprole, thiacloprid, thiamethoxam, thiodicarb, thiosultap-sodium, tioxazafen (3-phenyl-5-(2-thienyl)-1,2,4-oxadiazole), tolfenpyrad, tralomethrin, triazamate, trichlorfon, triflumezopyrim (2,4-dioxo-1-(5-pyrimidinylmethyl)-3-[3-(trifluoromethyl)phenyl]-2H-pyrido[1,2-a]pyrimidinium inner salt), triflumuron, tyclopyrazoflor, *Bacillus thuringiensis* delta-endotoxins, entomopathogenic bacteria, entomopathogenic viruses and entomopathogenic fungi.

Of note are insecticides such as abamectin, acetamiprid, acrinathrin, afidopyropen, amitraz, avermectin, azadirachtin, benfuracarb, bensultap, bifenthrin, buprofezin, cadusafos, carbaryl, cartap, chlorantraniliprole, chlorfenapyr, chlorpyrifos, clothianidin, cyantraniliprole, cyclaniliprole, cycloprothrin, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenitrothion, fenothiocarb, fenoxycarb, fenvalerate, fipronil, flometoquin, flonicamid, flubendiamide, flufenoxuron, flufenoxystrobin, flufensulfone, flupiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, metofluthrin, monofluorothrin, nitenpyram, nithiazine, novaluron, oxamyl, pyflubumide, pymetrozine, pyrethrin, pyridaben, pyridalyl, pyriminostrobin, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumezopyrim, triflumuron, *Bacillus thuringiensis* delta-endotoxins, all strains of *Bacillus thuringiensis* and all strains of nucleo polyhedrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedrovirus (NPV) such as *Helicoverpa zea* nucleopolyhedrovirus (HzNPV), *Anagrapha falcifera* nucleopolyhedrovirus (AfNPV); and granulosis virus (GV) such as *Cydia pomortella* granulosis virus (CpGV).

Of particular note is such a combination where the other invertebrate pest control active ingredient belongs to a different chemical class or has a different site of action than the compound of Formula A/Formula One. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, acetylcholinesterase (AChE) inhibitors such as the carbamates methomyl, oxamyl, thiodicarb, triazamate, and the organophosphates chlorpyrifos; GABA-gated chloride channel antagonists such as the cyclodienes dieldrin and endosulfan, and the phenylpyrazoles ethiprole and fipronil; sodium channel modulators such as the pyrethroids bifenthrin, cyfluthrin, beta-cyfluthrin, cyhalothrin, lambda-cyhalothrin, cypermethrin, deltamethrin, dimefluthrin, esfenvalerate, metofluthrin and profluthrin; nicotinic acetylcholinereceptor (nAChR) agonists such as the neonicotinoids acetamiprid, clothianidin, dinotefuran, imidacloprid, nitenpyram, nithiazine, thiacloprid, and thiamethoxam, and sulfoxaflor; nicotinic acetylcholine receptor (nAChR) allosteric activators such as the spinosyns spinetoram and spinosad; chloride channel activators such as the avermectins abamectin and emamectin; juvenile hormone mimics such as diofenolan, methoprene, fenoxycarb and pyriproxyfen; selective homopteran feeding blockers such as pymetrozine and flonicamid; mite growth inhibitors such as etoxazole; inhibitors of mitochondrial ATP synthase such as propargite; ucouplers of oxidative phosphorylation via disruption of the proton gradient such as chlorfenapyr; nicotinic acetylcholine receptor (nAChR) channel blockers such as the nereistoxin analogs cartap; inhibitors of chitin biosynthesis such as the benzoylareas flufenoxuron, hexaflumuron, lufenuron, novaluron, noviflumuron and triflumuron, and buprofezin; dipteran moulting disrupters such as cyromazine; ecdysone receptor agonists such as the diacylhydrazines methoxyfenozide and tebufenozide; octopamine receptor agonists such as amitraz; mitochondrial complex III electron transport inhibitors such as hydramethylnon; mitochondrial complex I electron transport inhibitors such as pyridaben; voltage-dependent sodium channel blockers such as indoxacarb; inhibitors of acetyl CoA carboxylase such as the tetronic and tetramic acids spirodiclofen, spiromesifen and spirotetramat; mitochondrial complex II electron transport inhibitors such as the β-ketonitriles cyenopyrafen and cyflumetofen; ryanidine receptor modulators such as the anthranilic diamides chlorantraniliprole, cyantraniliprole and cyantraniliprole, diamides such as flubendiamide, and ryanodine receptor ligands such as ryanodine; compounds wherein the target site responsible for biological activity is unknown or uncharacterized such as azadirachtin, bifenazate, pyridalyl, pyrifluquinazon and triflumezopyrim; microbial disrupters of insect midgut membranes such as Bacillus thuringensis and the delta-endotoxins they produce and Bacillus sphaericus; and biological agents including nucleo polyhedro viruses (NPV) and other naturally occurring or genetically modified insecticidal viruses.

Further examples of biologically active compounds or agents with which compounds of this invention can be formulated are: fungicides such as acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, etaconazole, edifenphos, enoxastrobin (also known as enestroburin), epoxiconazole, ethaboxam, ethirimol, etridiazole, famoxadone, fenamidone, fenaminstrobin, fenarimol, fenbuconazole, fenfuram, fenhexamide, fenoxanil, fenpiclonil, fenpropidin, fenpropimorph, fenpyrazamine, fentin acetate, fentin hydroxide, ferbam, ferimzone, flometoquin, fluazinam, fludioxonil, flufenoxystrobin, flumorph, fluopicolide, fluopyram, fluoxastrobin, fluquinconazole, flusilazole, flusulfamide, flutianil, flutolanil, flutriafol, fluxapyroxad, folpet, fthalide (also known as phthalide), fuberidazole, furalaxyl, furametpyr, hexaconazole, hymexazole, guazatine, imazalil, imibenconazole, iminoctadine albesilate, iminoctadine triacetate, iodicarb, ipconazole, isofetamid, iprobenfos, iprodione, iprovalicarb, isoprothiolane, isopyrazam, isotianil, kasugamycin, kresoxim-methyl, mancozeb, mandipropamid, mandestrobin, maneb, mapanipyrin, mepronil, meptyldinocap, metalaxyl (including metalaxyl-M/mefenoxam), metconazole, methasulfocarb, metiram, metominostrobin, metrafenone, myclobutanil, naftitine, neo-asozin (ferric methanearsonate), nuarimol, octhilinone, ofurace, orysastrobin, oxadixyl, oxathiapiprolin, oxolinic acid, oxpoconazole, oxycarboxin, oxytetracycline, penconazole, pencycuron, penflufen, penthiopyrad, perfurazoate, phosphorous acid (including salts thereof, e.g., fosetyl-aluminm), picarbutratox, picoxystrobin, piperalin, polyoxin, probenazole, prochloraz, procymidone, propamocarb, propiconazole, propineb, proquinazid, prothiocarb, prothioconazole, pyraclostrobin, pyrametostrobin, pyraoxystrobin, pyrazophos, pyribencarb, pyributacarb, pyrifenox, pyriofenone, perisoxazole, pyrimethanil, pyrifenox, pyrrolnitrin, pyroquilon, quinconazole, quinmethionate, quinoxyfen, quintozene, silthiofam, sedaxane, simeconazole, spiroxamine, streptomycin, sulfur, tebuconazole, tebufloquin, teclofthalam, tecloftalarn, tecnazene, terbinafine, tetraconazole, thiabendazole, thifluzamide, thiophanate, thiophanate-methyl, thiram, tiadinil, tolclofos-methyl, tolprocarb, tolyfluanid, triadimefon, triadimenol, triarimol, triazoxide, tribasic copper sulfate, triclopyricarb, tridemorph, trifloxystrobin, triflumizole, trimoprhamide tricyclazole, triforine, triticonazole, uniconazole, validamycin, valifenalate (also known as valifenal), vinclozolin, zineb, ziram and zoxamide; nematocides such as fluopyram, spirotetramat, thiodicarb, fosthiazate, abamectin, iprodione, fluensulfone, dimethyl disulfide, tioxazafen, 1,3-dichloropropene (1,3-D), metam (sodium and potassium), dazomet, chloropicrin, fenamiphos, ethoprophos, cadusaphos, terbufos, imicyafos, oxamyl, carbofuran, tioxazafen, Bacillus firmus and Pasteuria nishizawae; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include The Pesticide Manual, 13th Edition, C. D. S. Tomlin, Ed., British Crop Protection Council, Farnham, Surrey, U.K., 2003 and The BioPesticide Manual, 2$^{nd}$ Edition, L. G. Copping, Ed., British Crop Protection Council, Farnham, Surrey, U.K., 2001.

Compounds of this invention can be combined or formulated with polynucleotides including, but not limited to, DNA, RNA, and/or chemically modified nucleotides influencing the amount of a particular target through down regulation, interference, suppression or silencing of the genetically derived transcript that render an insecticidal effect.

For embodiments where one or more of these various mixing partners are used, the weight ratio of these various mixing partners (in total) to the compound of Formula A/Formula One is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula A/Formula One alone.

Table C lists specific combinations of a compound of Formula A/Formula One with other invertebrate pest control agents illustrative of the mixtures, compositions and methods of the present invention. The first column of Table C lists the specific invertebrate pest control agents (e.g., "Abamectin" in the first line). The second column of Table C lists the mode of action (if known) or chemical class of the invertebrate pest control agents. The third column of Table C lists embodiments) of ranges of weight ratios for rates at which the invertebrate pest control agent can be applied relative to a compound of Formula A/Formula One (e.g., "50:1 to 1:50" of abamectin relative to a compound of Formula A/Formula One by weight). Thus, for example, the first line of Table C specifically discloses the combination of a compound of Formula A/Formula One with abamectin can be applied in a weight ratio between 50:1 to 1:50. The remaining lines of Table C are to be construed similarly. Of further note Table C lists specific combinations of a compound of Formula A/Formula One with other invertebrate pest control agents illustrative of the mixtures, compositions and methods of the present invention and includes additional embodiments of weight ratio ranges for application rates.

TABLE C

| Invertebrate Pest Control Agent | Mode of Action or Chemical Class | Typical Weight Ratio |
| --- | --- | --- |
| Abamectin | Chloride channel activator | 50:1 to 1:50 |
| Acetamiprid | Nicotinic acetylcholine receptor (nAChR) agonist | 150:1 to 1:200 |
| Amitraz | Octopamine receptor agonist | 200:1 to 1:100 |
| Avermectin | Macrocyclic lactones | 50:1 to 1:50 |
| Azadirachtin | Unknown site of action | 100:1 to 1:120 |
| Beta-cyfluthrin | Sodium channel modulators | 150:1 to 1:200 |
| Bifenthrin | Sodium channel modulators | 100:1 to 1:10 |
| Buprofezin | Chitin biosynthesis inhibitors | 500:1 to 1:50 |
| Cartap | Nicotinic acetylcholine receptor (nAChR) channel blocker | 100:1 to 1:200 |
| Chlorantraniliprole | Ryanodine receptor modulator | 100:1 to 1:120 |
| Chlorfenapyr | Uncouplers of oxidative phosphorylation | 300:1 to 1:200 |
| Chlorpyrifos | Acetylcholine esterase inhibitor | 500:1 to 1:200 |
| Clothianidin | Nicotinic acetylcholine receptor (nAChR) agonist | 100:1 to 1:400 |
| Cyantraniliprole | Ryanodine receptor modulator | 100:1 to 1:120 |
| Cyfluthrin | Sodium channel modulator | 150:1 to 1:200 |
| Cyhalothrin | Sodium channel modulator | 150:1 to 1:200 |
| Cypermethrin | Sodium channel modulator | 150:1 to 1:200 |
| Cyromazine | Dipteran moulting disrupter | 400:1 to 1:50 |
| Deltamethrin | Sodium channel modulators | 50:1 to 1:400 |
| Dieldrin | GABA-gated chloride channel antagonist | 200:1 to 1:100 |
| Dinotefuran | Nicotinic acetylcholine receptor (nAChR) agonist | 150:1 to 1:200 |
| Diofenolan | Juvenile hormone mimic | 150:1 to 1:200 |
| Emamectin | Chloride channel activator | 50:1 to 1:10 |
| Endosulfan | GABA-gated chloride channel antagonist | 200:1 to 1:100 |
| Esfenvalerate | Sodium channel modulator | 100:1 to 1:400 |
| Ethiprole | GABA-regulated chloride channel antagonist | 200:1 to 1:100 |
| Fenothiocarb | | 150:1 to 1:200 |
| Fenoxycarb | Juvenile hormone mimic | 500:1 to 1:100 |
| Fenvalerate | Sodium channel modulator | 150:1 to 1:200 |
| Fipronil | GABA-regulated chloride channel antagonist | 150:1 to 1:100 |
| Flonicamid | Selective homopteran feeding blocker | 200:1 to 1:100 |
| Flubendiamide | Ryanodine receptor modulator | 100:1 to 1:120 |
| Flufenoxuron | Chitin biosynthesis inhibitor | 200:1 to 1:100 |
| Hexaflumuron | Chitin biosynthesis inhibitor | 300:1 to 1:50 |
| Hydramethylnon | Mitochondrial complex III electron transport inhibitor | 150:1 to 1:250 |
| Imidacloprid | Nicotinic acetylcholone receptor (nAChR) agonist | 1000:1 to 1:1000 |
| Indoxacarb | Voltage-dependent sodium channel blocker | 200:1 to 1:50 |
| Lambda-cyhalothrin | Sodium channel modulator | 50:1 to 1:250 |
| Lufenuron | Chitin biosynthesis inhibitor | 500:1 to 1:250 |
| Metaflumizone | Voltage-depedent sodium channel blocker | 200:1 to 1:200 |
| Methomyl | Acetylcholine esterase inhibitor | 500:1 to 1:100 |
| Methoprene | Juvenile hormone mimic | 500:1 to 1:100 |
| Methoxyfenozide | Ecdysone receptor agonist | 50:1 to 1:50 |
| Nitenpyram | Nicotinic acetylcholine receptor (nAChR) agonist | 150:1 to 1:200 |
| Nithiazine | Nicotinic acetylcholine receptor (nAChR) agonist | 150:1 to 1:200 |
| Novaluron | Chitin biosynthesis inhibitor | 500:1 to 1:150 |
| Oxamyl | Acetylcholine esterase inhibitor | 200:1 to 1:200 |
| Pymetrozine | Selective homopteran feeding blocker | 200:1 to 1:100 |
| Pyrethrin | Sodium channel modulator | 100:1 to 1:10 |
| Pyridaben | Mitochondrial complex I electron transport inhibitor | 200:1 to 1:100 |
| Pytidalyl | Unknown site of action | 200:1 to 1:100 |

TABLE C-continued

| Invertebrate Pest Control Agent | Mode of Action or Chemical Class | Typical Weight Ratio |
|---|---|---|
| Pyriproxyfen | Juventile hormone mimic | 500:1 to 1:100 |
| Ryanodine | Ryanodine receptor ligand | 100:1 to 1:120 |
| Spinetoram | Nicotinic acetylcholine receptor (nAChR) allosteric activator | 150:1 to 1:100 |
| Spinosad | Nicotinic acetylcholine receptor (nAChR) allosteric activator | 500:1 to 1:10 |
| Spirodiclofen | Acetyl CoA carboxylase inhibitor | 200:1 to 1:200 |
| Spiromesifen | Acetyl CoA carboxylase inhibitor | 200:1 to 1:200 |
| Tebufenozide | Ecdsone receptor agonist | 500:1 to 1:250 |
| Thiacloprid | Nicotinic acetylcholine receptor (nAChR) agonist | 100:1 to 1:200 |
| Thiamethoxam | Nicotinic acetylcholine receptor (nAChR) agonist | 1250:1 to 1:1000 |
| Thiodicarb | Acetylcholine esterase inhibitor | 500:1 to 1:400 |
| Thiosultap-sodium | Nicotinic acetylcholine receptor (nAChR) channel blocker | 150:1 to 1:100 |
| Tralomethrin | Sodium channel modulator | 150:1 to 1:200 |
| Triazamate | Acetylcholine esterase inhibitor | 250:1 to 1:100 |

TABLE C-continued

| Invertebrate Pest Control Agent | Mode of Action or Chemical Class | Typical Weight Ratio |
|---|---|---|
| Triflumezopyrim | | 100:1 to 1:100 |
| Triflumuron | Chitin synthesis inhibitor | 200:1 to 1:100 |
| Bacillus thuringiensis | Biological agents | 50:1 to 1:10 |
| Bacillus thuringiensis Delta-endotoxin | Biological agents | 50:1 to 1:10 |
| NPV (e.g, Gemstar) | Biological agents | 50:1 to 1:10 |

EXAMPLES

The examples are for illustration purposes and are not to be construed as limiting the invention disclosed in this document to only the embodiments disclosed in these examples.

Starting materials, reagents and solvents which are obtained from commercial sources are used without further purification. Anhydrous solvents are purchased as Sure/Seal™ from Aldrich and are used as received. Melting points are obtained on a Thomas Hoover Unimelt capillary melting point apparatus or an OptiMelt Automated Melting Point System from Sanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw, or ACD Name Pro. If such programs are unable to name a molecule, such molecule is named using conventional naming rules. $^1$H nuclear magnetic resonance (NMR) spectral data are in parts per million (ppm, δ) and were recorded at 300, 400, or 500; $^{13}$C NMR spectral data are in ppm (δ) and were recorded at 75, 100, or 150 MHz, and $^{19}$F NMR spectral data are in ppm (δ) and were recorded at 376 MHz, unless otherwise stated.

Example 1: Preparation of N—((Z)-3-(2-isopropyl-5-methylphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A1)

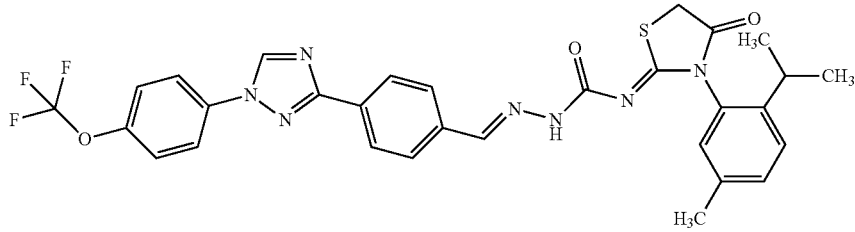 [SMILES: Cc1ccc(C(C)C)c(N2C(=O)CS/C2=N\C(=O)N/N=C/c2ccc(-c3ncn(-c4ccc(OC(F)(F)F)cc4)n3)cc2)c1]

To a stirred solution of (E)-3-(4-(hydrazonomethyl)phenyl)-1-(4-(trifluoromethoxy)phenyl)-1H-1,2,4-triazole (prepared as in Example 1, step 1 in WO2013116053A1; 0.100 grams (g), 0.288 millimoles (mmol)) in acetonitrile (4 milliliters (mL)) at room temperature was added cesium carbonate (0.094 g, 0.288 mmol) and 4-nitrophenyl carbonochloridate (0.058 g, 0.288 mmol). The reaction mixture was stirred for one hour at room temperature. 2-Imino-3-(2-isopropyl-5-methylphenyl)thiazolidin-4-one (prepared as in Example 83 in WO 2014160031A1; 0.072 g, 0.288 mmol) was added to the reaction mixture, followed by cesium carbonate (0.094 g, 0.288 mmol). The reaction mixture was stirred for one hour at room temperature and then concentrated under reduced pressure. The resulting solid was dried onto Celite® and purified by flash column chromatography using 0-60% acetonehexanes as eluent. Product fractions were combined and concentrated; the crude product was triturated with diethyl ether; and the solids were collected by filtration and dried under vacuum. The title compound was isolated as a cream colored solid (0.068 g, 38%).

The following compounds were prepared in like manner to the procedure outlined in Example 1:

N—((Z)-3-(2-Isopropylphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A2)

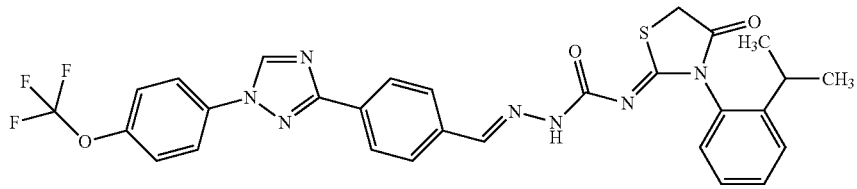 [SMILES: CC(C)c1ccccc1N1C(=O)CS/C1=N\C(=O)N/N=C/c1ccc(-c2ncn(-c3ccc(OC(F)(F)F)cc3)n2)cc1]

Isolated as a light brown solid (0.057 g, 33%).

N—((Z)-3-(2-Ethyl-6-methylphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A3)

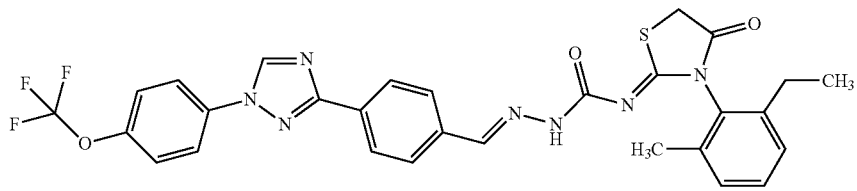 [SMILES: CCc1cccc(C)c1N1C(=O)CS/C1=N\C(=O)N/N=C/c1ccc(-c2ncn(-c3ccc(OC(F)(F)F)cc3)n2)cc1]

Isolated as a white solid (0.037 g, 21%).

N—((Z)-3-(2-Chloro-5-methylphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A4)

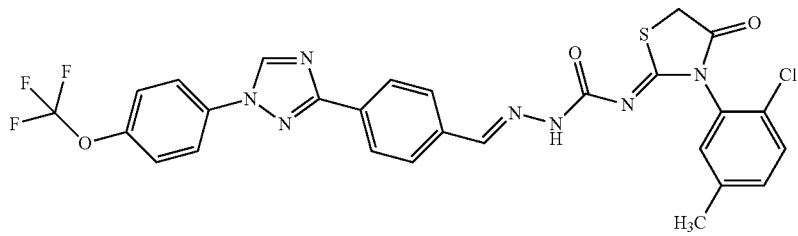 [SMILES: Cc1ccc(Cl)c(N2C(=O)CS/C2=N\C(=O)N/N=C/c2ccc(-c3ncn(-c4ccc(OC(F)(F)F)cc4)n3)cc2)c1]

Isolated as a light yellow solid (0.132 g, 37%).

N—((Z)-3-(2-Ethoxy-5-methylphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A5)

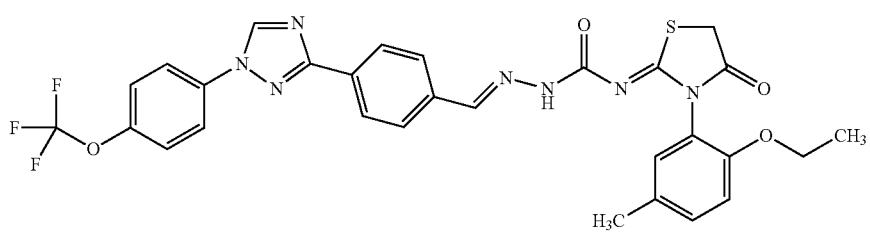 [SMILES: CCOc1ccc(C)cc1N1C(=O)CS/C1=N\C(=O)N/N=C/c1ccc(-c2ncn(-c3ccc(OC(F)(F)F)cc3)n2)cc1]

Isolated as a yellow solid (0.041 g, 11%).

N—((Z)-3-(5-Methyl-2-(2,2,2-trifluoroethoxy)phenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A6)

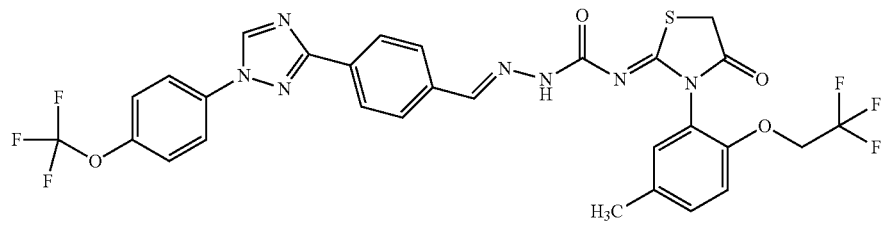 [SMILES: Cc1ccc(OCC(F)(F)F)c(N2C(=O)CS/C2=N\C(=O)N/N=C/c2ccc(-c3ncn(-c4ccc(OC(F)(F)F)cc4)n3)cc2)c1]

Isolated as a yellow solid (0.086 g, 22%).

N—((Z)-3-(4-Methoxy-2-methylphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A7)

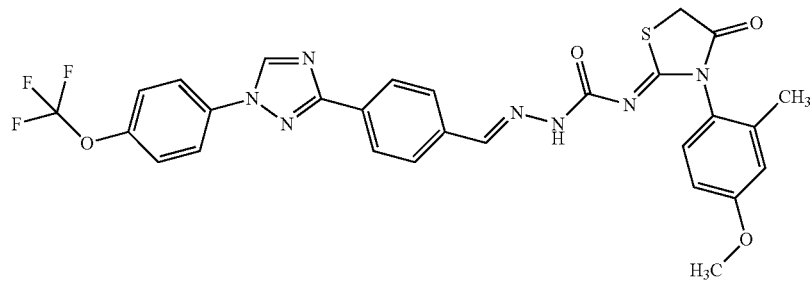 [SMILES: COc1ccc(N2C(=O)CS/C2=N\C(=O)N/N=C/c2ccc(-c3ncn(-c4ccc(OC(F)(F)F)cc4)n3)cc2)c(C)c1]

Isolated as a yellow solid (0.130 g, 37%).

N—((Z)-3-(2-Ethoxyphenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A8)

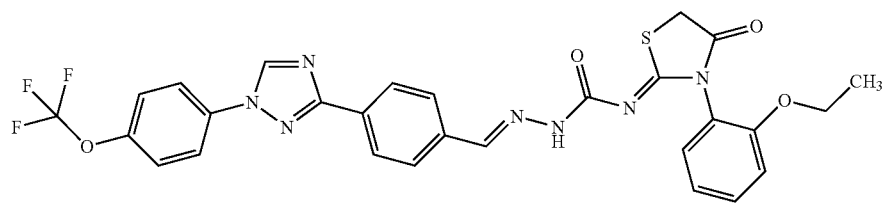 [SMILES: CCOc1ccccc1N1C(=O)CS/C1=N\C(=O)N/N=C/c1ccc(-c2ncn(-c3ccc(OC(F)(F)F)cc3)n2)cc1]

Isolated as a light yellow solid (0.047 g, 27%)

N—((Z)-3-(5-methyl-2-(trifluoromethyl)phenyl)-4-oxothiazolidin-2-ylidene)-2-((E)-4-(1-(4-(trifluoromethoxy)phenyl)-1H-1,2,4-triazol-3-yl)benzylidene)hydrazine-1-carboxamide (A9)

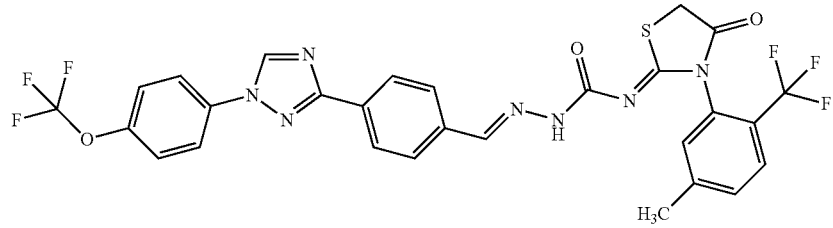 [SMILES: Cc1ccc(C(F)(F)F)c(N2C(=O)CS/C2=N\C(=O)N/N=C/c2ccc(-c3ncn(-c4ccc(OC(F)(F)F)cc4)n3)cc2)c1]

Isolated as a yellow solid (0.056 g, 30%).

Example 2: Preparation of 2-imino-3-(2-isopropylphenyl)thiazolidin-4-one (C1)

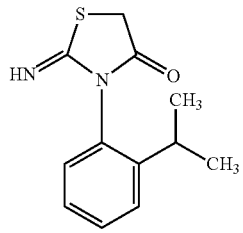 [SMILES: CC(C)c1ccccc1N1C(=N)SCC1=O]

Step 1. 2-Chloro-N-(2-isopropylphenyl)acetamide (C9)

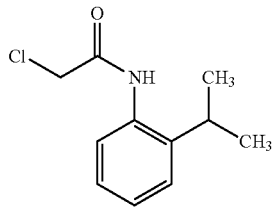

To a stirred solution of 2-isopropylaniline (3.0 g, 22.19 mmol) in ethyl acetate (22 mL) cooled in an ice bath were added sequentially sodium bicarbonate (3.73 g, 44.4 mmol) and chloroacetyl chloride (2.1 mL, 26.6 mmol) dropwise over four minutes. After stirring in the ice bath for ten minutes, the reaction mixture was warmed to room temperature and stirred for 90 minutes. Water (15 mL) was added to the reaction mixture, and the phases were separated. The organic layer was washed with brine (20 mL), dried over magnesium sulfate, filtered, and concentrated to afford the title compound as a dark solid (4.9 g, 94%): $^1$H NMR (400 MHz, CDCl$_3$) δ 8.32 (s, 1H), 7.82-7.75 (m, 1H), 7.35-7.29 (m, 1H), 7.25-7.21 (m, 2H), 4.26 (s, 2H), 3.04 (hept, J=6.9 Hz, 1H), 1.28 (d, J=6.8 Hz, 6H); $^{13}$C NMR (126 MHz, CDCl$_3$) δ 164.06, 140.06, 133.10, 126.57, 126.50, 125.77, 123.78, 43.21, 28.12, 22.87; IR (thin film) 3255, 2963, 2869, 1662, 1525 cm-1.

Step 2. 2-Imino-3-(2-isopropylphenyl)thiazolidin-4-one (C1)

To a solution of 2-chloro-N-(2-isopropylphenyl)acetamide (C9) (4.7 g, 22.20 mmol) in acetone (22.2 mL) was added potassium thiocyanate (4.32 g, 44.4 mmol) as a solid. The reaction mixture was warmed to reflux and stirred for 5 hours. The reaction mixture was then cooled to room temperature and stirred for 1 hour. Cesium carbonate (0.362 g, 1.110 mmol) was added, and the reaction mixture was stirred at room temperature for 45 minutes. The reaction mixture was then filtered, and the cake was washed with acetone (2×15 mL). The mother liquors were absorbed onto Celite® and purified by flash column chromatography using 0-60% ethyl acetate/hexanes as eluent. Product fractions were combined and concentrated. The crude product oil was triturated with ethanol (30 mL) while stirring in an ice bath for 30 minutes. The solids were collected by filtration and washed with cold ethanol (3×10 mL), then dried in a vacuum oven for 18 hours at 40° C. The title compound was isolated as a white solid (2.36 g, 46%): $^1$H NMR (400 MHz, DMSO-d$_6$) δ 9.22 (s, 1H), 7.47-7.38 (m, 2H), 7.27 (ddd, J=7.8, 6.9, 1.9 Hz, 1H), 7.08 (dd, J=7.8, 1.2 Hz, 1H), 4.32-4.11 (m, 2H), 2.70 (h, J=7.0 Hz, 1H), 1.10 (dd, J=9.2, 6.9 Hz, 6H); $^{13}$C NMR (126 MHz, DMSO-d$_6$) δ 172.37, 158.55, 146.89, 133.60, 129.72, 129.64, 126.94, 126.72, 34.20, 28.33, 24.05, 23.74; ESIMS m/z 235 ([M+H]$^+$).

The following compounds were prepared in like manner to the procedure outlined in Example 2:

3-(2-Ethyl-6-methylphenyl)-2-iminothiazolidin-4-one (C2)

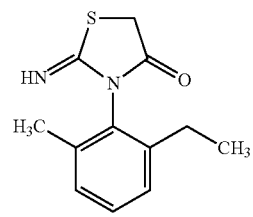 [SMILES: CCc1cccc(C)c1N1C(=N)SCC1=O]

Isolated as a white solid (4.21 g, 81%): $^1$H NMR (400 MHz, DMSO-d$_6$) δ 9.24 (s, 1H), 7.28 (t, J=7.5 Hz, 1H), 7.23-7.13 (m, 2H), 4.28 (d, J=0.7 Hz, 2H), 2.35 (q, J=7.8, 7.4 Hz, 2H), 2.03 (s, 3H), 1.12-1.03 (m, 3H); $^{13}$C NMR (126 MHz, DMSO-d$_6$) δ 171.92, 157.37, 142.10, 136.39, 133.44, 129.35, 128.47, 126.85, 34.06, 24.15, 17.71, 14.76; ESIMS m/z 235 ([M+H]$^+$).

3-(2-Chloro-5-methylphenyl)-2-iminothiazolidin-4-one (C3)

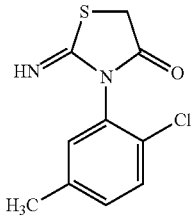

Isolated as a yellow solid (3.0 g, 90%): mp 125-127° C.; $^1$H NMR (400 MHz, DMSO-$d_6$) δ 9.31 (s, 1H), 7.49 (d, J=8.2 Hz, 1H), 7.35-7.25 (m, 1H), 7.21 (d, J=2.1 Hz, 1H), 4.30-4.13 (m, 2H), 2.32 (s, 3H); $^{13}$C NMR (126 MHz, DMSO-$d_6$) δ 170.36, 156.15, 137.25, 131.98, 130.96, 130.61, 128.76, 128.22, 33.13, 19.56; ESIMS m/z 241 ([M+H]$^+$).

3-(2-Ethoxy-5-methylphenyl)-2-iminothiazolidin-4-one (C4)

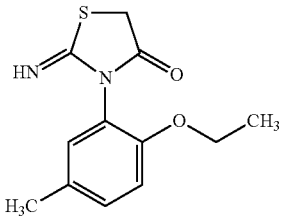 [SMILES: CCOc1ccc(C)cc1N1C(=N)SCC1=O]

Isolated as a brown solid (0.545 g, 59%): mp 65-70° C.; $^1$H NMR (400 MHz, CDCl$_3$) δ 8.31 (s, 1H), 8.17-8.10 (m, 1H), 6.88 (ddd, J=8.4, 2.1, 0.9 Hz, 1H), 6.78 (d, J=8.3 Hz, 1H), 4.11 (q, J=7.0 Hz, 2H), 3.91 (s, 2H), 2.30 (t, J=0.7 Hz, 3H), 1.46 (t, J=7.0 Hz, 3H); $^{13}$C NMR (126 MHz, CDCl$_3$) δ 162.07, 145.26, 130.58, 126.23, 125.14, 120.48, 110.91, 110.84, 64.48, 38.10, 20.94, 14.87; EIMS m/z 250.

2-Imino-3-(5-methyl-2-(2,2,2-trifluoroethoxy)phenyl)thiazolidin-4-one (C5)

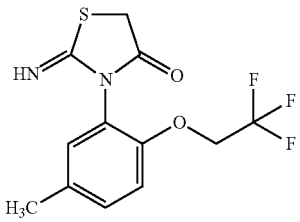 [SMILES: Cc1ccc(OCC(F)(F)F)c(N2C(=N)SCC2=O)c1]

Isolated as a white solid (0.510 g, 71%): mp 127-129° C.; $^1$H NMR (400 MHz, CDCl$_3$) δ 8.18 (d, J=15.6 Hz, 2H), 6.93 (d, J=8.3 Hz, 1H), 6.80 (d, J=8.3 Hz, 1H), 4.43 (q, J=8.0 Hz, 2H), 3.90 (s, 2H), 2.33 (d, J=0.8 Hz, 3H); $^{19}$F NMR (376 MHz, CDCl$_3$) δ -73.95; EIMS m/z 304.

2-imino-3-(4-methoxy-2-methylphenyl)thiazolidin-4-one (C6)

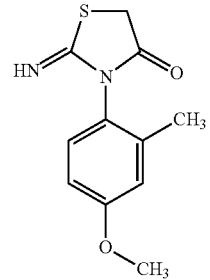 [SMILES: COc1ccc(N2C(=N)SCC2=O)c(C)c1]

Isolated as a brown gum (2.05 g, 59%): $^1$H NMR (400 MHz, DMSO-$d_6$) δ 9.18 (s, 1H), 7.02 (d, J=8.6 Hz, 1H), 6.90 (d, J=2.9 Hz, 1H), 6.83 (dd, J=8.7, 3.0 Hz, 1H), 4.24-4.09 (m, 2H), 3.77 (s, 3H), 2.02 (s, 3H); $^{13}$C NMR (101 MHz, DMSO-$d_6$) δ 171.54, 159.19, 157.53, 137.27, 130.02, 127.00, 115.46, 111.96, 55.25, 33.51, 17.24; ESIMS m/z 237 ([M+H]$^+$).

3-(2-Ethoxyphenyl)-2-iminothiazolidin-4-one (C7)

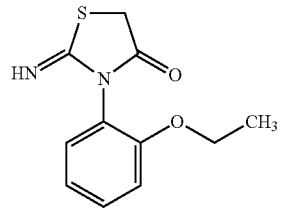 [SMILES: CCOc1ccccc1N1C(=N)SCC1=O]

Isolated as an orange oil (4.80 g, 89%): $^1$H NMR (400 MHz, CDCl$_3$) δ 7.76 (s, 1H), 7.42 (s, 1H), 7.18 (d, J=7.7 Hz, 1H), 7.12-7.02 (m, 2H), 4.09-4.04 (m, 4H), 1.34 (t, J=7.0 Hz, 3H); $^{13}$C NMR (126 MHz, CDCl$_3$) δ 170.81, 154.51, 131.33, 130.01, 121.16, 113.48, 64.30, 14.66; ESIMS m/z 237 ([M+H]$^+$).

2-Imino-3-(5-methyl-2-(trifluoromethyl)phenyl)thiazolidin-4-one (C8)

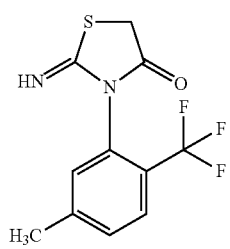 [SMILES: Cc1ccc(C(F)(F)F)c(N2C(=N)SCC2=O)c1]

Isolated as an orange solid (2.63 g, 84%): mp 118-127° C.; $^1$H NMR (400 MHz, DMSO-$d_6$) δ 9.33 (s, 1H), 7.74 (d, J=8.0 Hz, 1H), 7.50 (ddd, J=8.0, 1.8, 0.9 Hz, 1H), 7.29 (t, J=1.2 Hz, 1H), 4.29-4.09 (m, 2H), 2.41 (s, 3H); $^{19}$F NMR (376 MHz, DMSO-$d_6$) δ -59.80; ESIMS m/z 275 ([M+H]$^+$).

Using the procedures disclosed herein the following list of prophetic molecules having a structure according to Formula A may be made (Table P).

| Cmpd. No. | Structure |
|---|---|
| P1 | 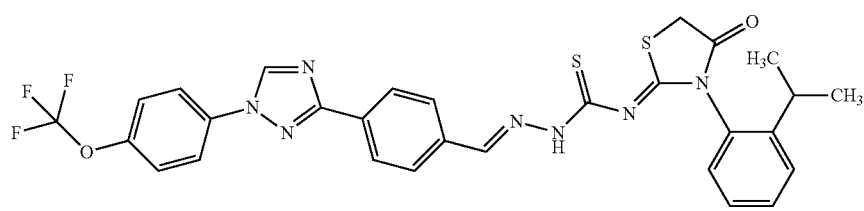 |
| P2 | 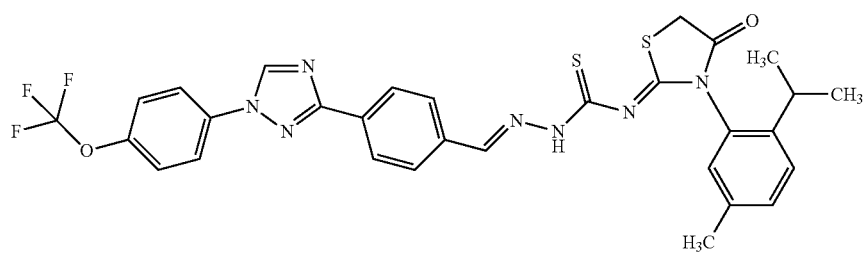 [SMILES: Cc1ccc(C(C)C)c(N2C(=O)CS/C2=N\C(=S)N/N=C/c2ccc(-c3ncn(-c4ccc(OC(F)(F)F)cc4)n3)cc2)c1] |
| P3 | 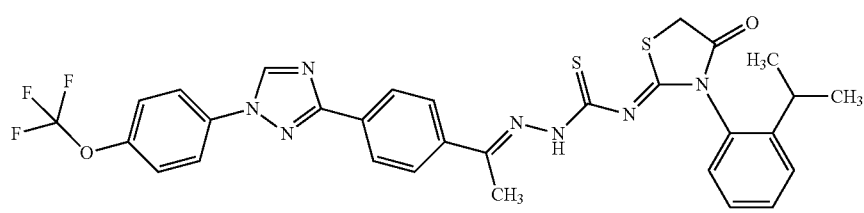 [SMILES: C/C(=N\NC(=S)/N=C1\SCC(=O)N1c1ccccc1C(C)C)c1ccc(-c2ncn(-c3ccc(OC(F)(F)F)cc3)n2)cc1] |
| P4 | 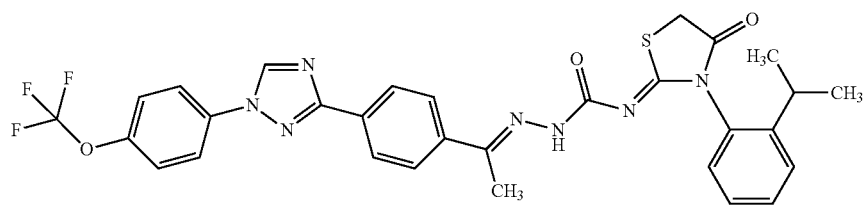 [SMILES: C/C(=N\NC(=O)/N=C1\SCC(=O)N1c1ccccc1C(C)C)c1ccc(-c2ncn(-c3ccc(OC(F)(F)F)cc3)n2)cc1] |
| P5 | 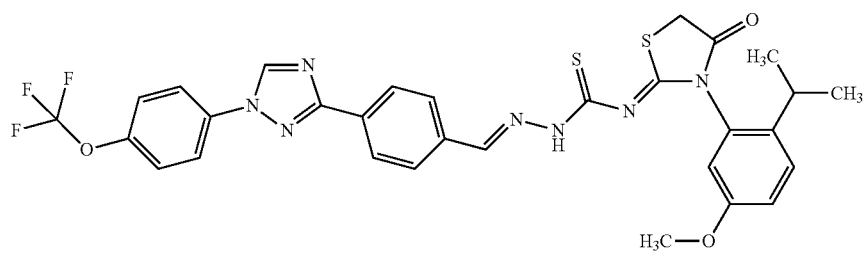 [SMILES: COc1ccc(C(C)C)c(N2C(=O)CS/C2=N\C(=O)N/N=C/c2ccc(-c3ncn(-c4ccc(OC(F)(F)F)cc4)n3)cc2)c1] |
| P6 | 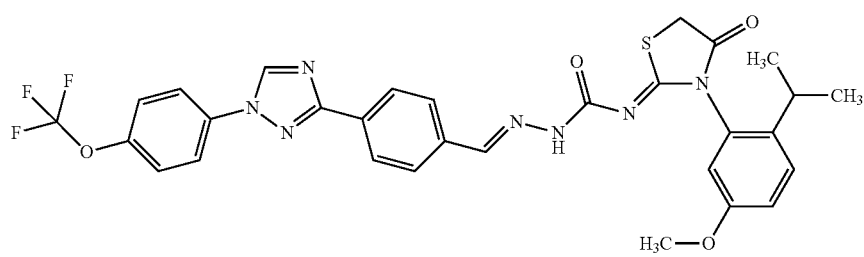 |

-continued

| Cmpd. No. | Structure |
|---|---|
| P7 | 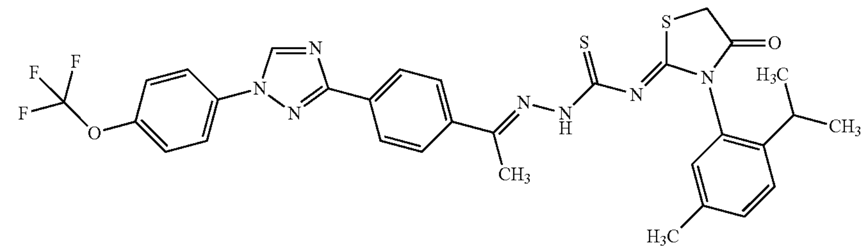 [SMILES: C/C(=N\NC(=S)/N=C1\SCC(=O)N1c1cc(C)ccc1C(C)C)c1ccc(-c2ncn(-c3ccc(OC(F)(F)F)cc3)n2)cc1] |
| P8 | 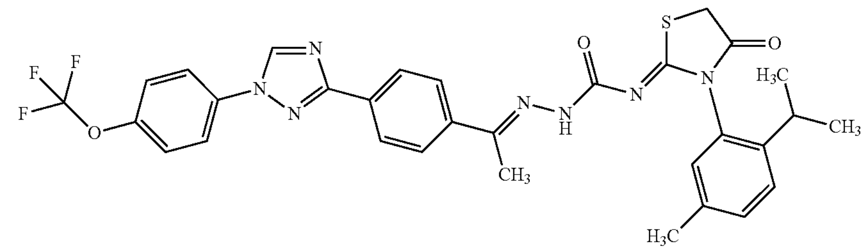 [SMILES: C/C(=N\NC(=O)/N=C1\SCC(=O)N1c1cc(C)ccc1C(C)C)c1ccc(-c2ncn(-c3ccc(OC(F)(F)F)cc3)n2)cc1] |
| P9 | 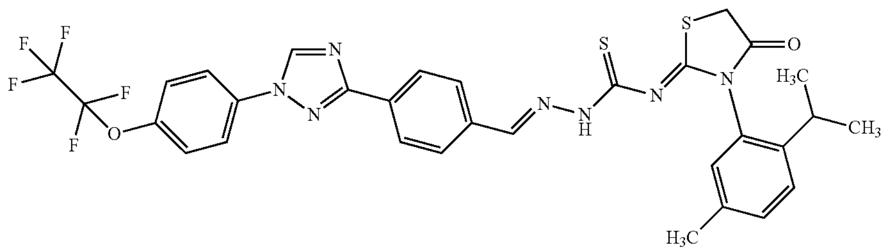 [SMILES: Cc1ccc(C(C)C)c(N2C(=O)CS/C2=N\C(=S)N/N=C/c2ccc(-c3ncn(-c4ccc(OC(F)(F)C(F)(F)F)cc4)n3)cc2)c1] |
| P10 | 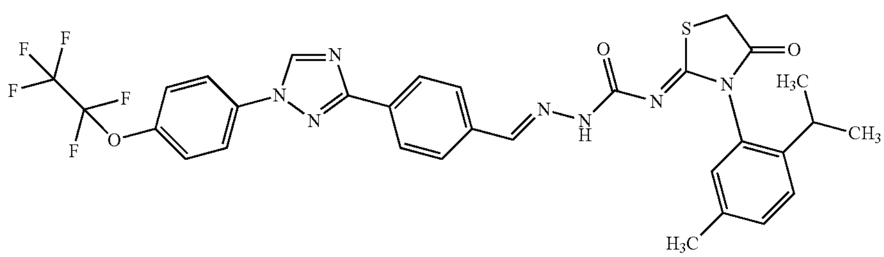 [SMILES: Cc1ccc(C(C)C)c(N2C(=O)CS/C2=N\C(=O)N/N=C/c2ccc(-c3ncn(-c4ccc(OC(F)(F)C(F)(F)F)cc4)n3)cc2)c1] |
| P11 | 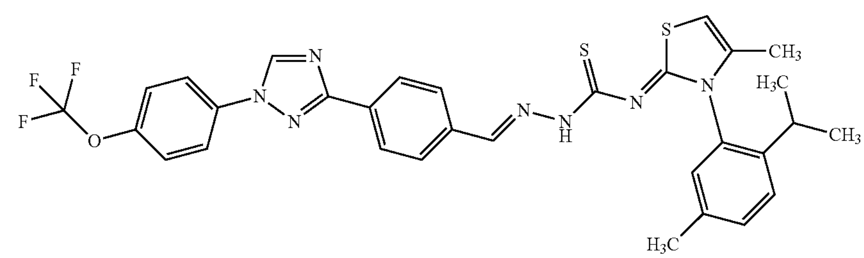 [SMILES: Cc1ccc(C(C)C)c(-n2c(C)cs/c2=N\C(=S)N/N=C/c2ccc(-c3ncn(-c4ccc(OC(F)(F)F)cc4)n3)cc2)c1] |
| P12 | 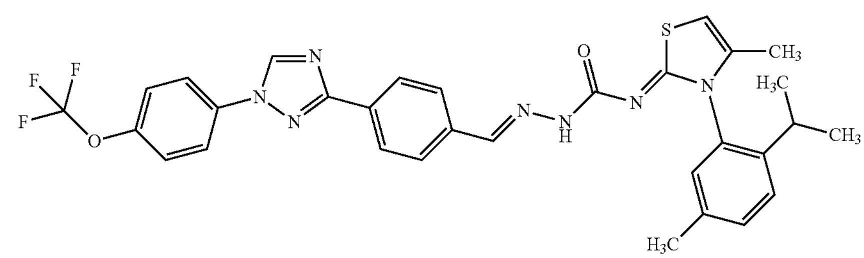 [SMILES: Cc1ccc(C(C)C)c(-n2c(C)cs/c2=N\C(=O)N/N=C/c2ccc(-c3ncn(-c4ccc(OC(F)(F)F)cc4)n3)cc2)c1] |

-continued

| Cmpd. No. | Structure |
|---|---|
| P13 | 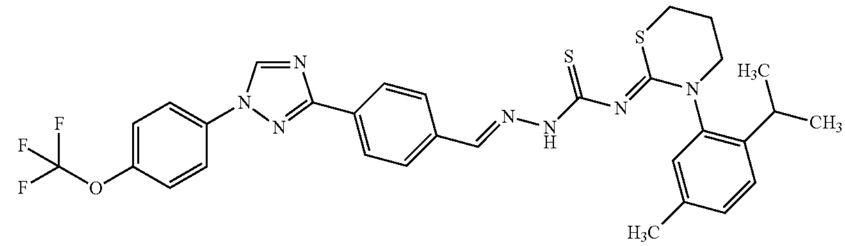 [SMILES: Cc1ccc(C(C)C)c(N2CCCS/C2=N\C(=S)N/N=C/c2ccc(-c3ncn(-c4ccc(OC(F)(F)F)cc4)n3)cc2)c1] |
| P14 | 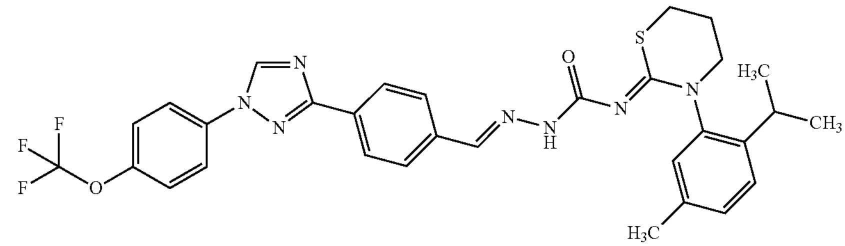 [SMILES: Cc1ccc(C(C)C)c(N2CCCS/C2=N\C(=O)N/N=C/c2ccc(-c3ncn(-c4ccc(OC(F)(F)F)cc4)n3)cc2)c1] |
| P15 | 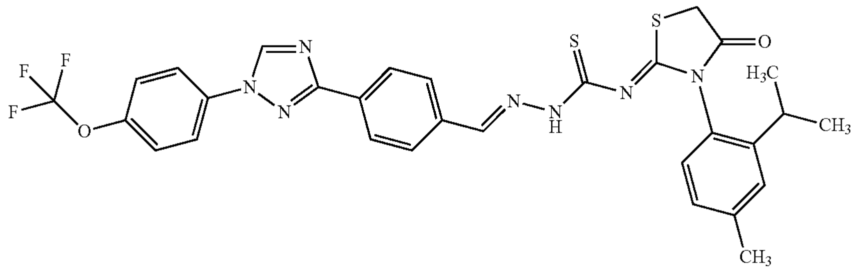 [SMILES: Cc1ccc(N2C(=O)CS/C2=N\C(=S)N/N=C/c2ccc(-c3ncn(-c4ccc(OC(F)(F)F)cc4)n3)cc2)c(C(C)C)c1] |
| P16 | 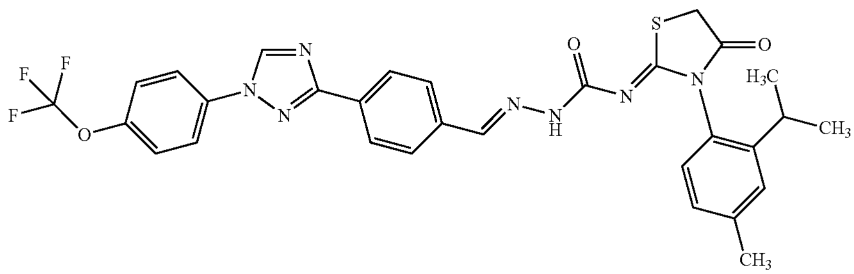 [SMILES: Cc1ccc(N2C(=O)CS/C2=N\C(=O)N/N=C/c2ccc(-c3ncn(-c4ccc(OC(F)(F)F)cc4)n3)cc2)c(C(C)C)c1] |
| P17 | 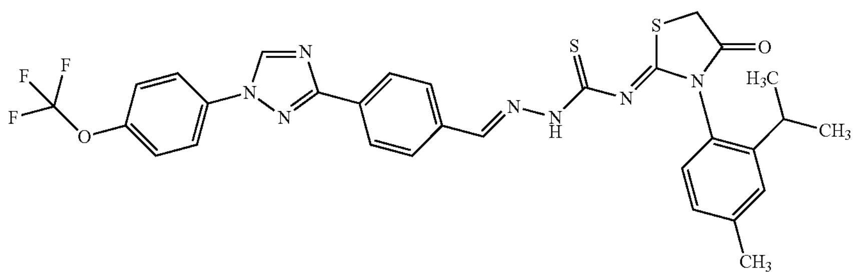 |
| P18 | 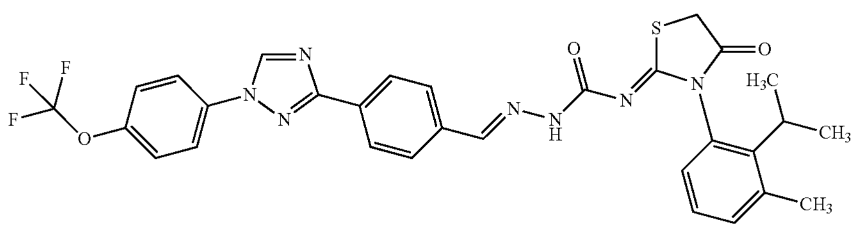 [SMILES: Cc1cccc(N2C(=O)CS/C2=N\C(=O)N/N=C/c2ccc(-c3ncn(-c4ccc(OC(F)(F)F)cc4)n3)cc2)c1C(C)C] |

-continued

| Cmpd. No. | Structure |
|---|---|
| P19 | 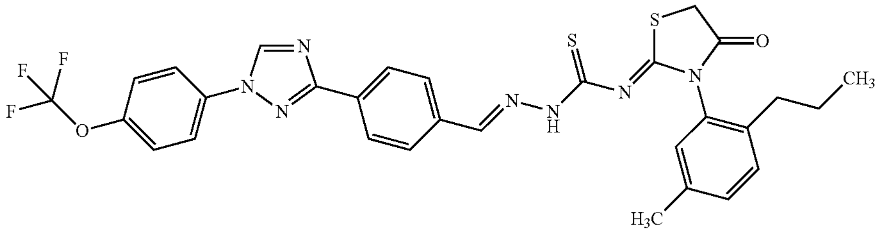 [SMILES: CCCc1ccc(C)cc1N1C(=O)CS/C1=N\C(=S)N/N=C/c1ccc(-c2ncn(-c3ccc(OC(F)(F)F)cc3)n2)cc1] |
| P20 | 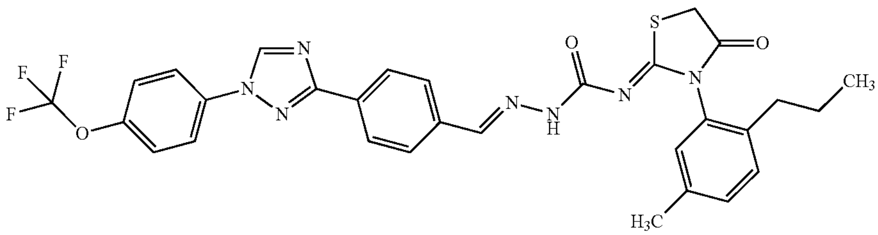 [SMILES: CCCc1ccc(C)cc1N1C(=O)CS/C1=N\C(=O)N/N=C/c1ccc(-c2ncn(-c3ccc(OC(F)(F)F)cc3)n2)cc1] |
| P21 | 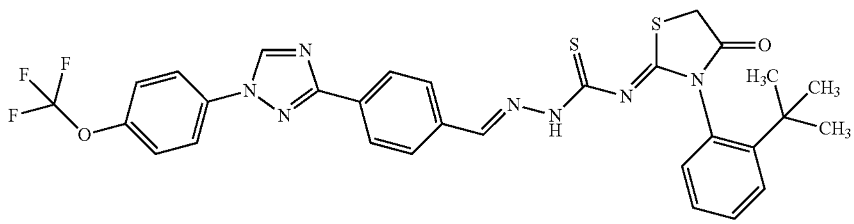 [SMILES: CC(C)(C)c1ccccc1N1C(=O)CS/C1=N\C(=S)N/N=C/c1ccc(-c2ncn(-c3ccc(OC(F)(F)F)cc3)n2)cc1] |
| P22 | 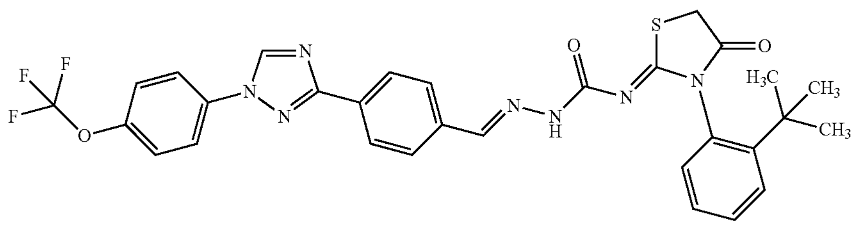 [SMILES: CC(C)(C)c1ccccc1N1C(=O)CS/C1=N\C(=O)N/N=C/c1ccc(-c2ncn(-c3ccc(OC(F)(F)F)cc3)n2)cc1] |
| P23 | 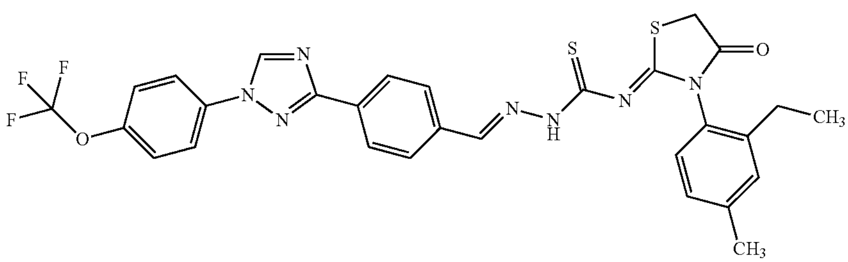 |
| P24 | 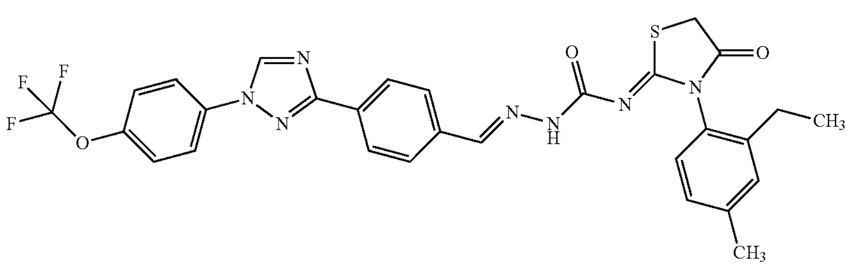 [SMILES: CCc1cc(C)ccc1N1C(=O)CS/C1=N\C(=O)N/N=C/c1ccc(-c2ncn(-c3ccc(OC(F)(F)F)cc3)n2)cc1] |

-continued
| Cmpd. No. | Structure |
|---|---|
| P25 | 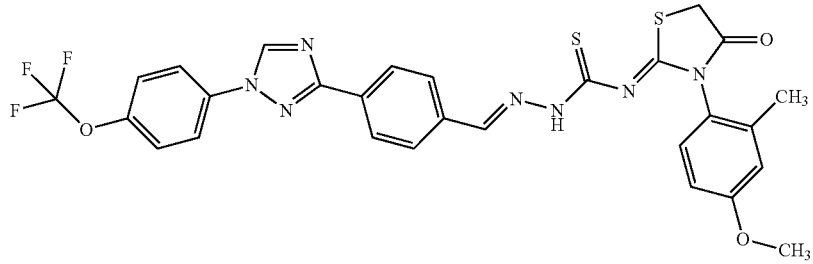 [SMILES: COc1ccc(N2C(=O)CS/C2=N\C(=S)N/N=C/c2ccc(-c3ncn(-c4ccc(OC(F)(F)F)cc4)n3)cc2)c(C)c1] |
| P26 | 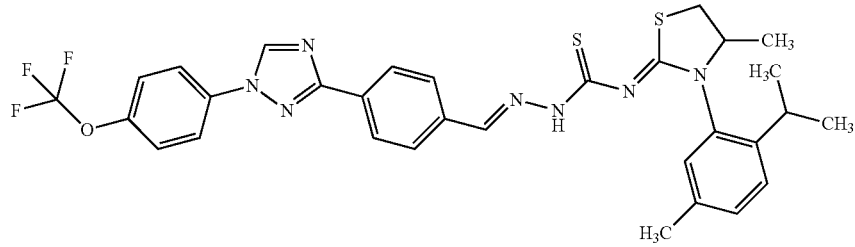 |
| P27 | 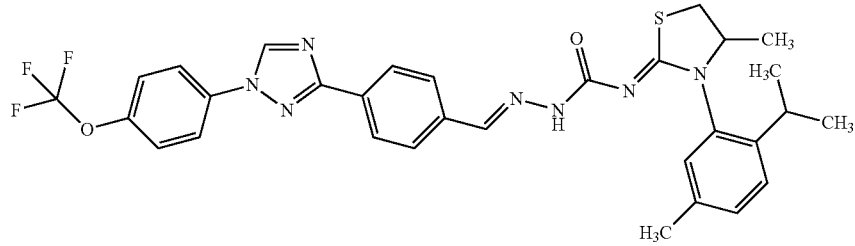 [SMILES: Cc1ccc(C(C)C)c(N2/C(=N/C(=O)N/N=C/c3ccc(-c4ncn(-c5ccc(OC(F)(F)F)cc5)n4)cc3)SCC2C)c1] |
| P28 | 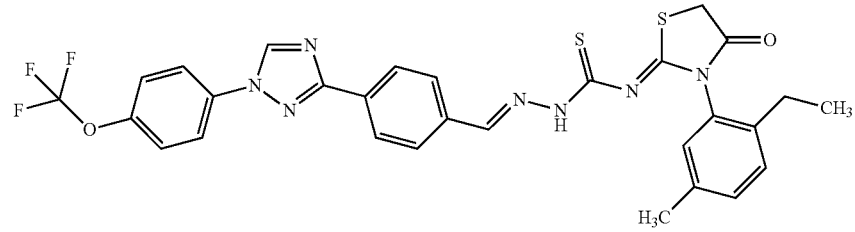 |
| P29 | 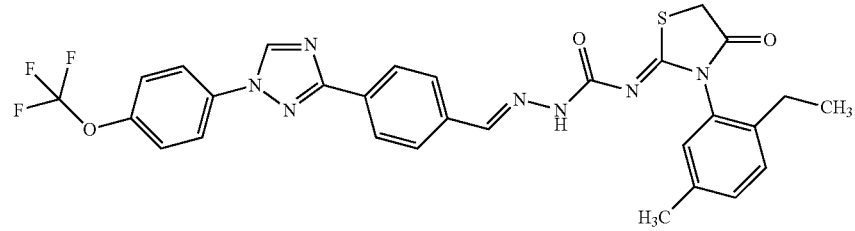 [SMILES: CCc1ccc(C)cc1N1C(=O)CS/C1=N\C(=O)N/N=C/c1ccc(-c2ncn(-c3ccc(OC(F)(F)F)cc3)n2)cc1] |
| P30 | 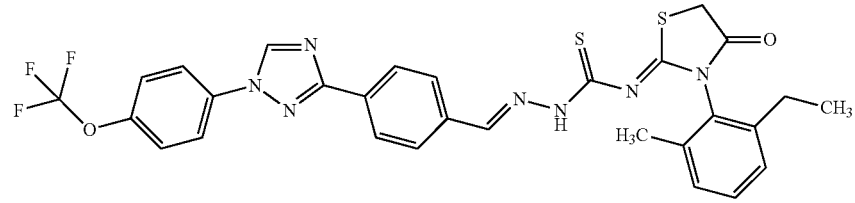 [SMILES: CCc1cccc(C)c1N1C(=O)CS/C1=N\C(=S)N/N=C/c1ccc(-c2ncn(-c3ccc(OC(F)(F)F)cc3)n2)cc1] |

| Cmpd. No. | Structure |
|---|---|
| P31 | 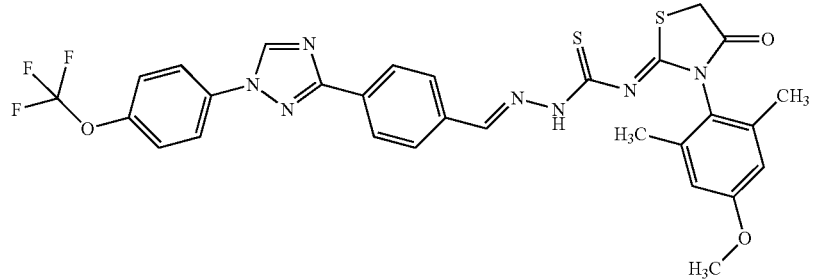 [SMILES: COc1cc(C)c(N2C(=O)CS/C2=N\C(=S)N/N=C/c2ccc(-c3ncn(-c4ccc(OC(F)(F)F)cc4)n3)cc2)c(C)c1] |
| P32 | 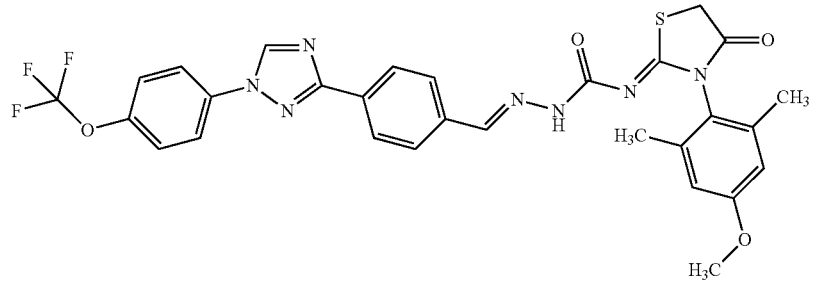 [SMILES: COc1cc(C)c(N2C(=O)CS/C2=N\C(=O)N/N=C/c2ccc(-c3ncn(-c4ccc(OC(F)(F)F)cc4)n3)cc2)c(C)c1] |
| P33 | 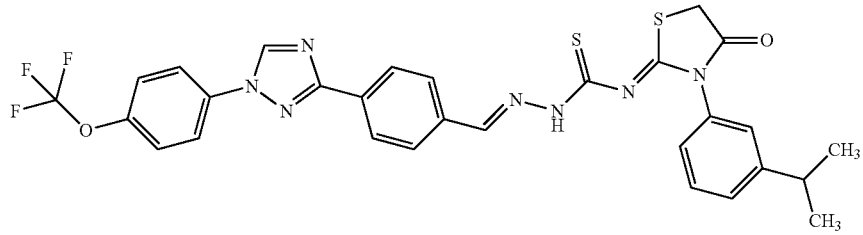 [SMILES: CC(C)c1cccc(N2C(=O)CS/C2=N\C(=O)N/N=C/c2ccc(-c3ncn(-c4ccc(OC(F)(F)F)cc4)n3)cc2)c1] |
| P34 | 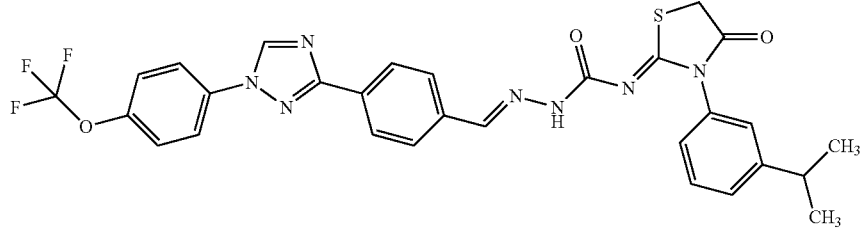 |
| P35 | 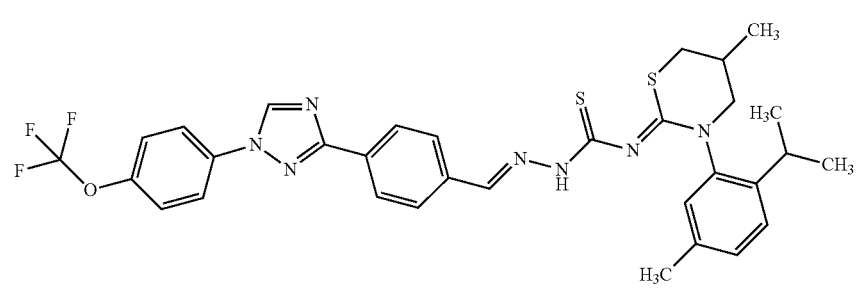 |

| Cmpd. No. | Structure |
|---|---|
| P36 | 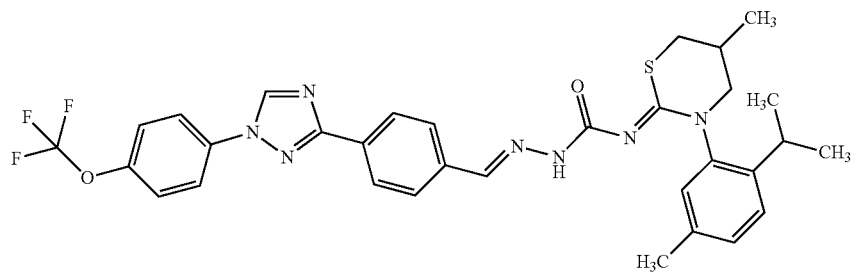 [SMILES: Cc1ccc(C(C)C)c(N2CC(C)CS/C2=N\C(=S)N/N=C/c2ccc(-c3ncn(-c4ccc(OC(F)(F)F)cc4)n3)cc2)c1] |
| P37 | 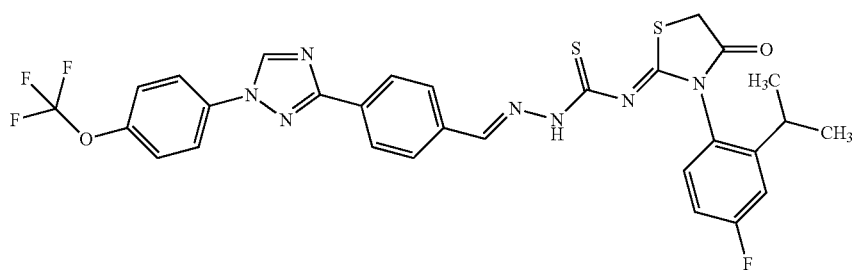 |
| P38 | 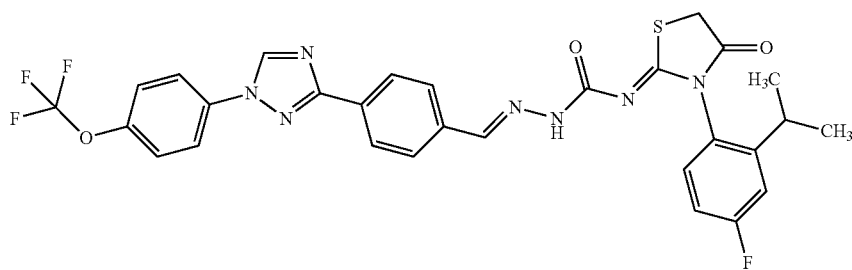 [SMILES: CC(C)c1cc(F)ccc1N1C(=O)CS/C1=N\C(=O)N/N=C/c1ccc(-c2ncn(-c3ccc(OC(F)(F)F)cc3)n2)cc1] |
| P39 | 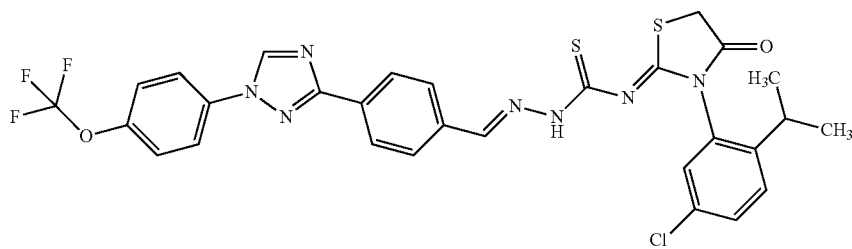 [SMILES: CC(C)c1ccc(Cl)cc1N1C(=O)CS/C1=N\C(=S)N/N=C/c1ccc(-c2ncn(-c3ccc(OC(F)(F)F)cc3)n2)cc1] |
| P40 | 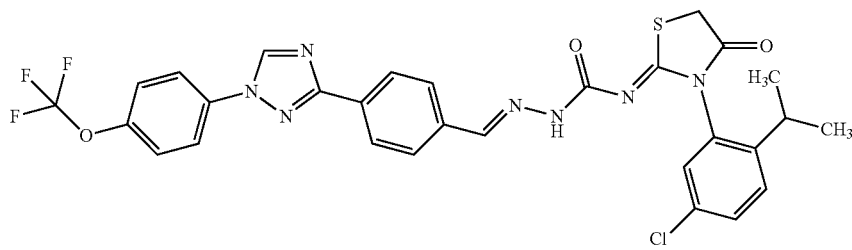 [SMILES: CC(C)c1ccc(Cl)cc1N1C(=O)CS/C1=N\C(=O)N/N=C/c1ccc(-c2ncn(-c3ccc(OC(F)(F)F)cc3)n2)cc1] |

| Cmpd. No. | Structure |
|---|---|
| P41 | 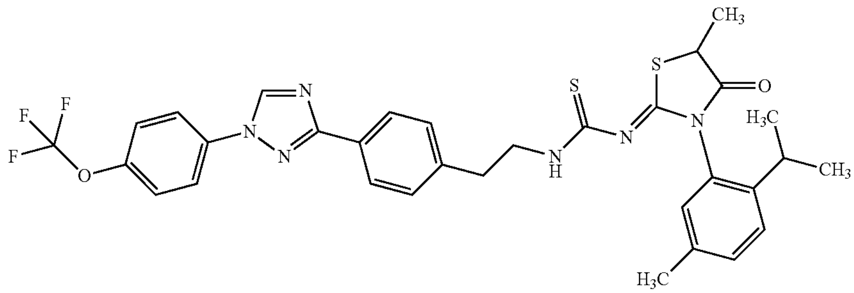 [SMILES: Cc1ccc(C(C)C)c(N2C(=O)C(C)S/C2=N\C(=S)NCCc2ccc(-c3ncn(-c4ccc(OC(F)(F)F)cc4)n3)cc2)c1] |
| P42 | 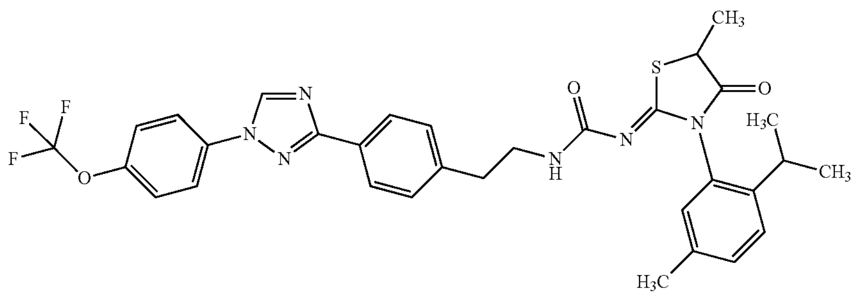 [SMILES: Cc1ccc(C(C)C)c(N2C(=O)C(C)S/C2=N\C(=O)NCCc2ccc(-c3ncn(-c4ccc(OC(F)(F)F)cc4)n3)cc2)c1] |
| P43 | 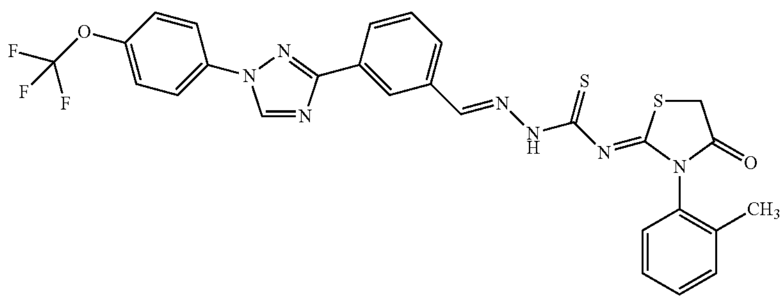 |
| P44 | 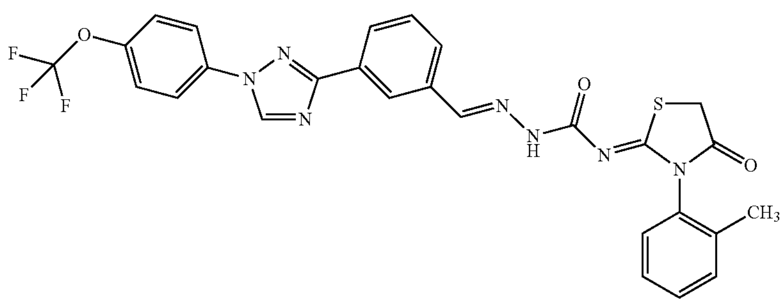 [SMILES: Cc1ccccc1N1C(=O)CS/C1=N\C(=S)N/N=C/c1cccc(-c2ncn(-c3ccc(OC(F)(F)F)cc3)n2)c1] |
| P45 | 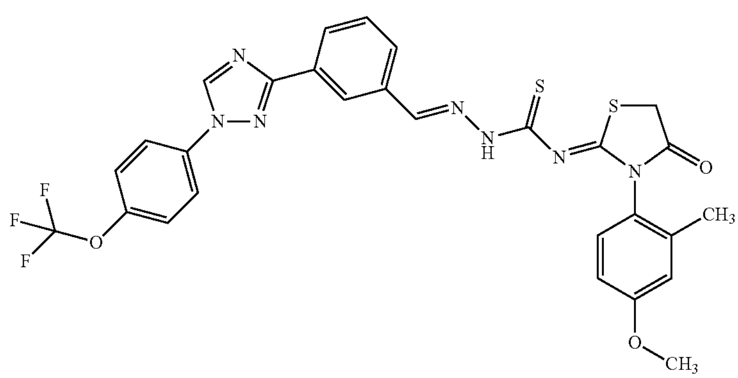 [SMILES: COc1ccc(N2C(=O)CS/C2=N\C(=S)N/N=C/c2cccc(-c3ncn(-c4ccc(OC(F)(F)F)cc4)n3)c2)c(C)c1] |

-continued
| Cmpd. No. | Structure |
|---|---|
| P46 | 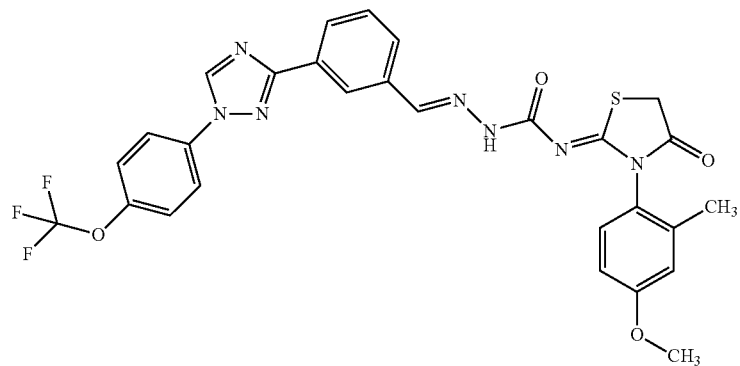 |
| P47 | 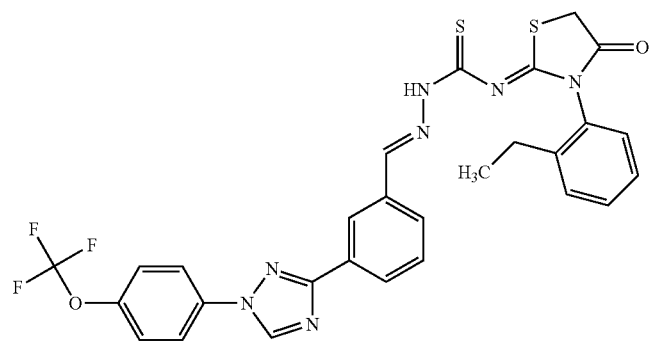 [SMILES: CCc1ccccc1N1C(=O)CS/C1=N\C(=S)N/N=C/c1cccc(-c2ncn(-c3ccc(OC(F)(F)F)cc3)n2)c1] |
| P48 | 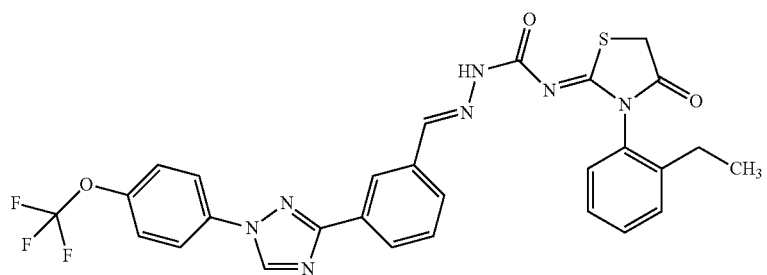 [SMILES: CCc1ccccc1N1C(=O)CS/C1=N\C(=O)N/N=C/c1cccc(-c2ncn(-c3ccc(OC(F)(F)F)cc3)n2)c1] |
| P49 | 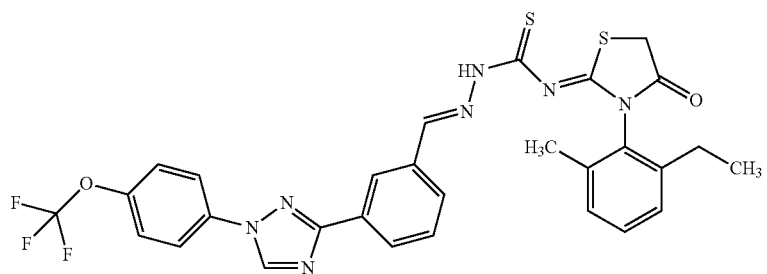 [SMILES: CCc1cccc(C)c1N1C(=O)CS/C1=N\C(=S)N/N=C/c1cccc(-c2ncn(-c3ccc(OC(F)(F)F)cc3)n2)c1] |
| P50 | 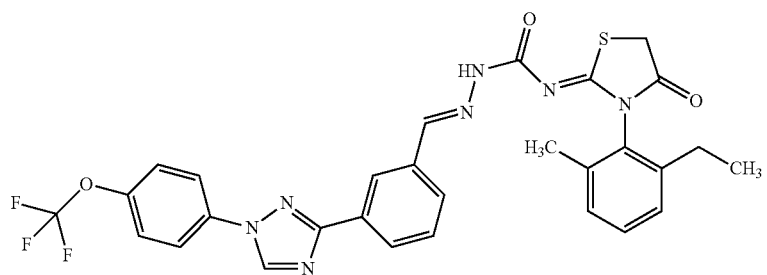 [SMILES: CCc1cccc(C)c1N1C(=O)CS/C1=N\C(=O)N/N=C/c1cccc(-c2ncn(-c3ccc(OC(F)(F)F)cc3)n2)c1] |

| Cmpd. No. | Structure |
|---|---|
| P51 | 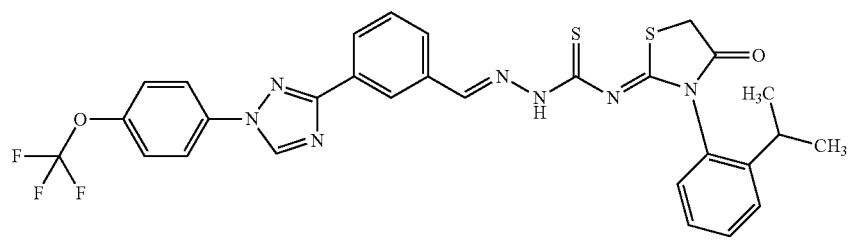 |
| P52 | 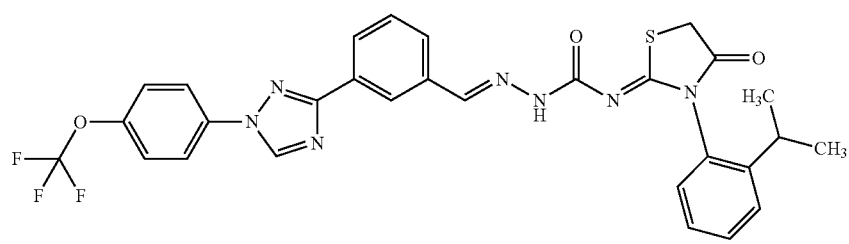 [SMILES: CC(C)c1ccccc1N1C(=O)CS/C1=N\C(=O)N/N=C/c1cccc(-c2ncn(-c3ccc(OC(F)(F)F)cc3)n2)c1] |
| P53 | 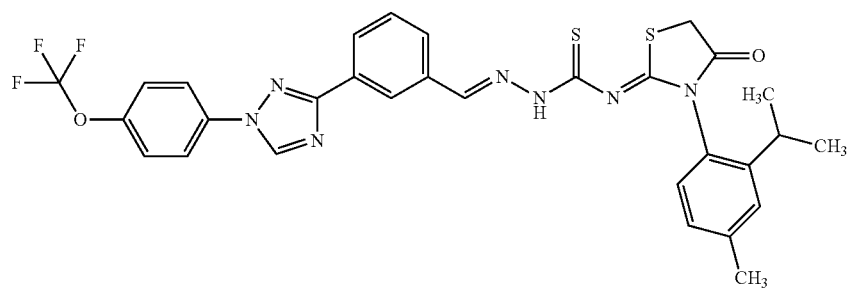 [SMILES: Cc1ccc(N2C(=O)CS/C2=N\C(=S)N/N=C/c2cccc(-c3ncn(-c4ccc(OC(F)(F)F)cc4)n3)c2)c(C(C)C)c1] |
| P54 | 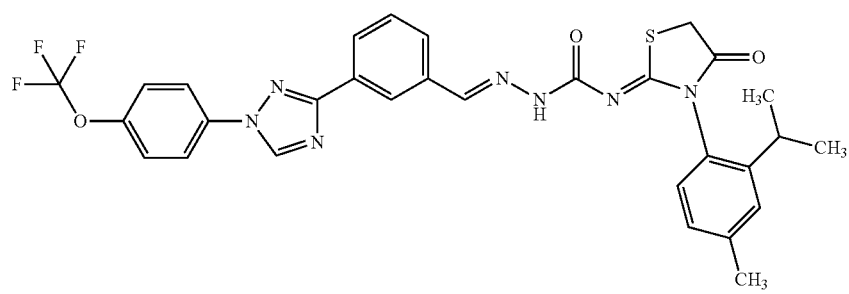 |
| P55 | 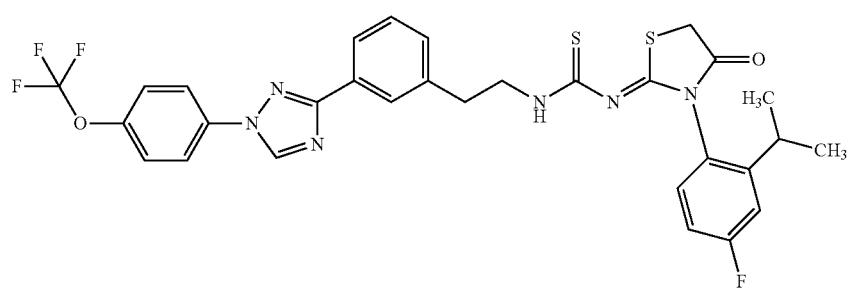 [SMILES: CC(C)c1cc(F)ccc1N1C(=O)CS/C1=N\C(=S)NCCc1cccc(-c2ncn(-c3ccc(OC(F)(F)F)cc3)n2)c1] |

| Cmpd. No. | Structure |
|---|---|
| P56 | 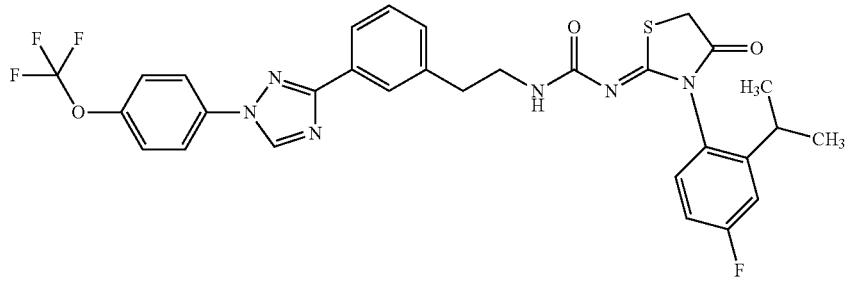 [SMILES: CC(C)c1cc(F)ccc1N1C(=O)CS/C1=N\C(=O)NCCc1cccc(-c2ncn(-c3ccc(OC(F)(F)F)cc3)n2)c1] |
| P57 | 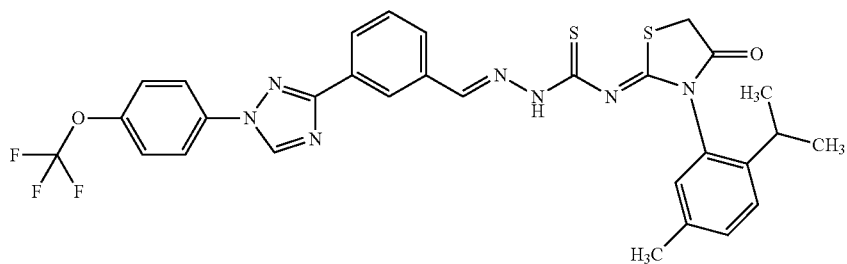 |
| P58 | 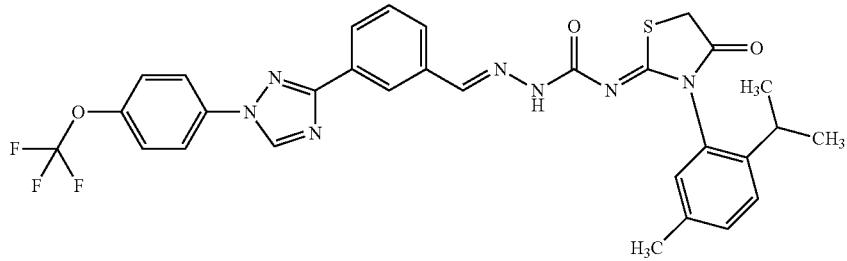 [SMILES: Cc1ccc(C(C)C)c(N2C(=O)CS/C2=N\C(=O)N/N=C/c2cccc(-c3ncn(-c4ccc(OC(F)(F)F)cc4)n3)c2)c1] |
| P59 | 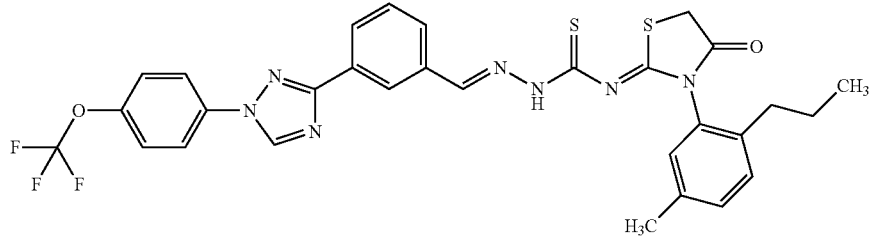 |
| P60 | 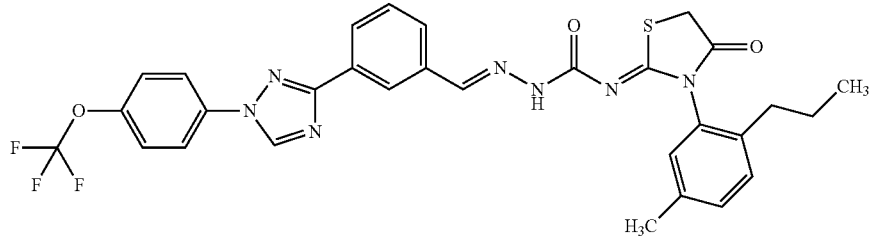 [SMILES: CCCc1ccc(C)cc1N1C(=O)CS/C1=N\C(=S)N/N=C/c1cccc(-c2ncn(-c3ccc(OC(F)(F)F)cc3)n2)c1] |

-continued
| Cmpd. No. | Structure |
|---|---|
| P61 | 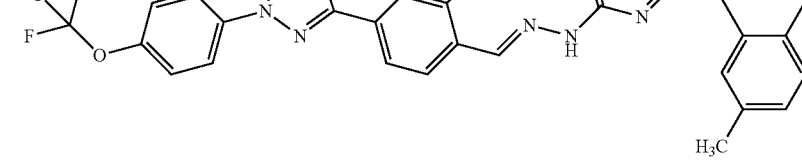 |
| P62 | 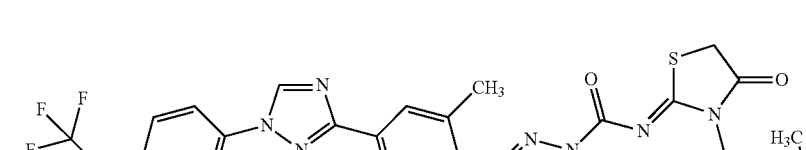 |
| P63 | 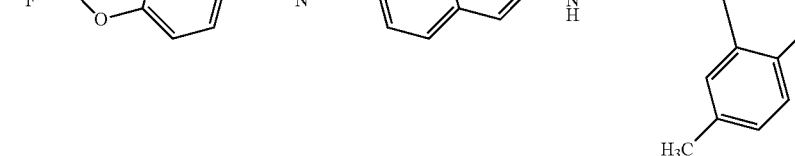 |
| P64 | 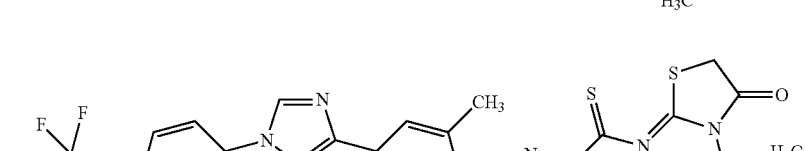 |
| P65 | 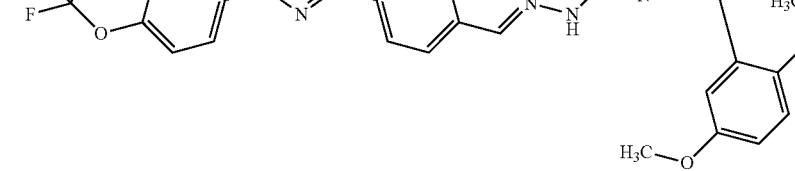 |

-continued

| Cmpd. No. | Structure |
|---|---|
| P66 | 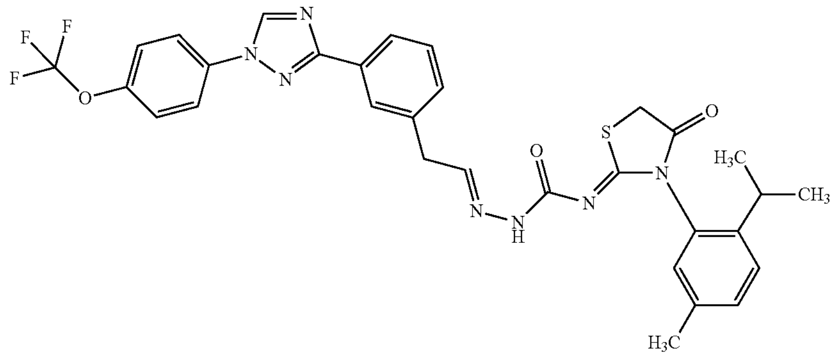 [SMILES: Cc1ccc(C(C)C)c(N2C(=O)CS/C2=N\C(=O)N/N=C/Cc2cccc(-c3ncn(-c4ccc(OC(F)(F)F)cc4)n3)c2)c1] |
| P67 | 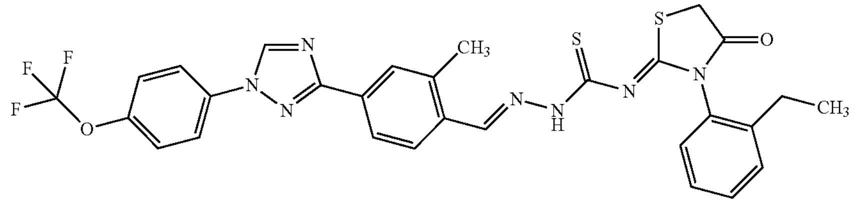 |
| P68 | 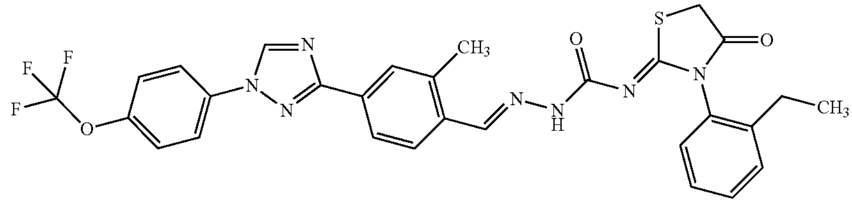 [SMILES: CCc1ccccc1N1C(=O)CS/C1=N\C(=O)N/N=C/c1ccc(-c2ncn(-c3ccc(OC(F)(F)F)cc3)n2)cc1C] |
| P69 | 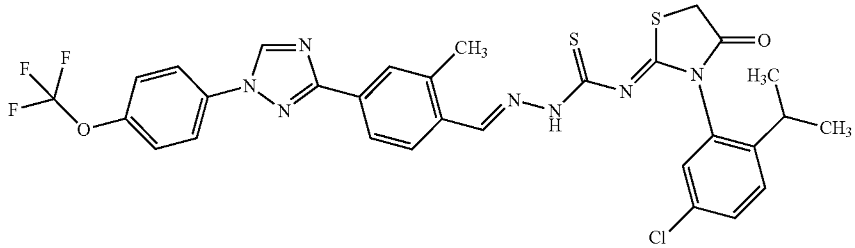 |
| P70 | 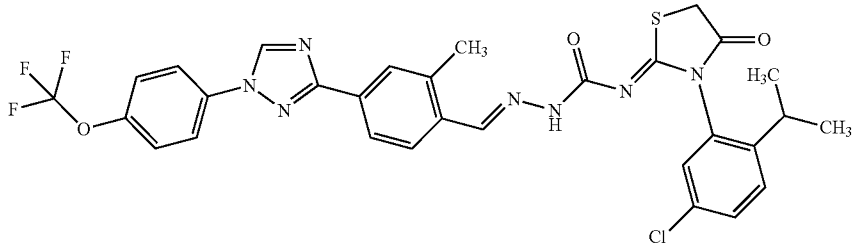 [SMILES: Cc1cc(-c2ncn(-c3ccc(OC(F)(F)F)cc3)n2)ccc1/C=N/NC(=S)/N=C1\SCC(=O)N1c1cc(Cl)ccc1C(C)C] |
| P71 | 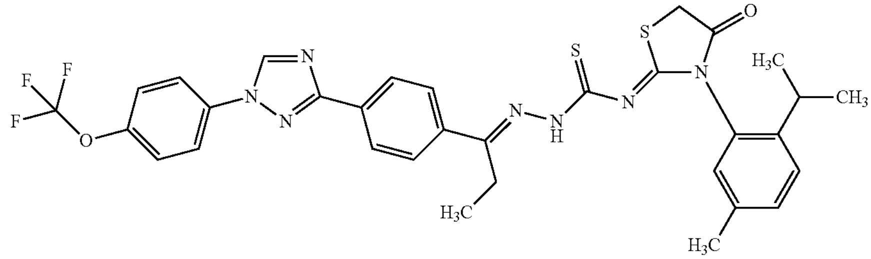 [SMILES: CC/C(=N\NC(=S)/N=C1\SCC(=O)N1c1cc(C)ccc1C(C)C)c1ccc(-c2ncn(-c3ccc(OC(F)(F)F)cc3)n2)cc1] |

-continued

| Cmpd. No. | Structure |
|---|---|
| P72 | 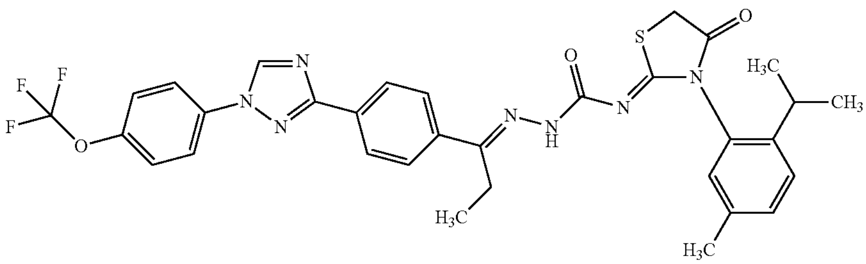 [SMILES: CC/C(=N\NC(=O)/N=C1\SCC(=O)N1c1cc(C)ccc1C(C)C)c1ccc(-c2ncn(-c3ccc(OC(F)(F)F)cc3)n2)cc1] |
| P73 | 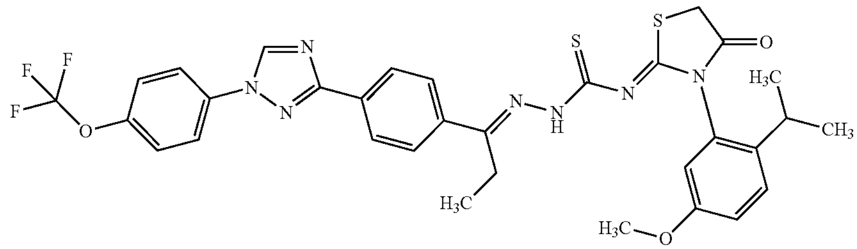 [SMILES: CC/C(=N\NC(=S)/N=C1\SCC(=O)N1c1cc(OC)ccc1C(C)C)c1ccc(-c2ncn(-c3ccc(OC(F)(F)F)cc3)n2)cc1] |
| P74 | 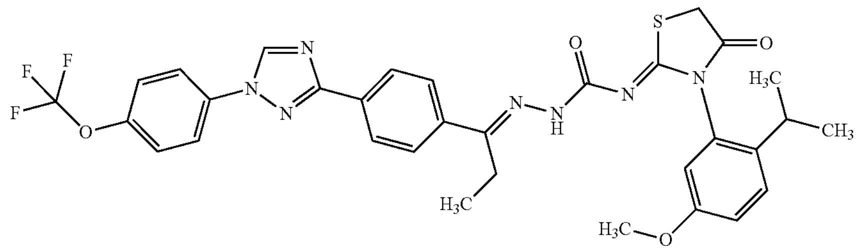 [SMILES: CC/C(=N\NC(=O)/N=C1\SCC(=O)N1c1cc(OC)ccc1C(C)C)c1ccc(-c2ncn(-c3ccc(OC(F)(F)F)cc3)n2)cc1] |
| P75 | 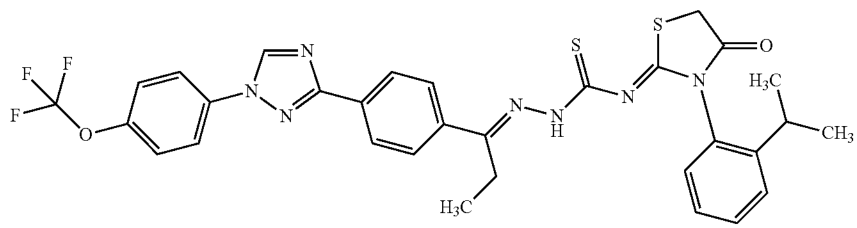 [SMILES: CC/C(=N\NC(=S)/N=C1\SCC(=O)N1c1ccccc1C(C)C)c1ccc(-c2ncn(-c3ccc(OC(F)(F)F)cc3)n2)cc1] |
| P76 | 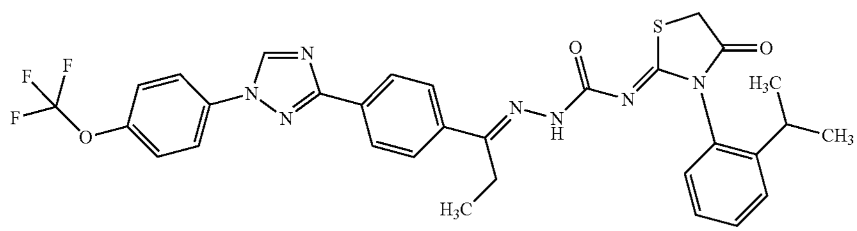 [SMILES: CC/C(=N\NC(=O)/N=C1\SCC(=O)N1c1ccccc1C(C)C)c1ccc(-c2ncn(-c3ccc(OC(F)(F)F)cc3)n2)cc1] |
| P77 | 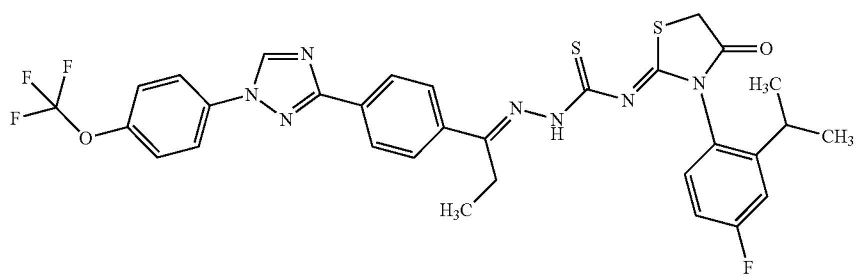 [SMILES: CC/C(=N\NC(=S)/N=C1\SCC(=O)N1c1ccc(F)cc1C(C)C)c1ccc(-c2ncn(-c3ccc(OC(F)(F)F)cc3)n2)cc1] |

| Cmpd. No. | Structure |
|---|---|
| P78 | 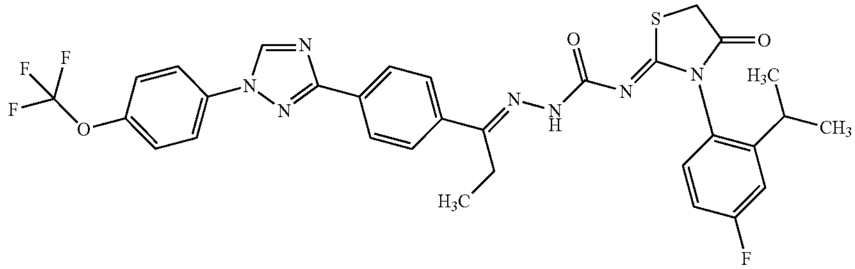 [SMILES: CC/C(=N\NC(=O)/N=C1\SCC(=O)N1c1ccc(F)cc1C(C)C)c1ccc(-c2ncn(-c3ccc(OC(F)(F)F)cc3)n2)cc1] |
| P79 | 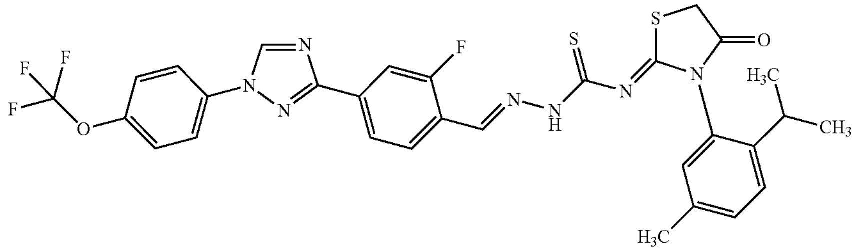 [SMILES: Cc1ccc(C(C)C)c(N2C(=O)CS/C2=N\C(=S)N/N=C/c2ccc(-c3ncn(-c4ccc(OC(F)(F)F)cc4)n3)cc2F)c1] |
| P80 | 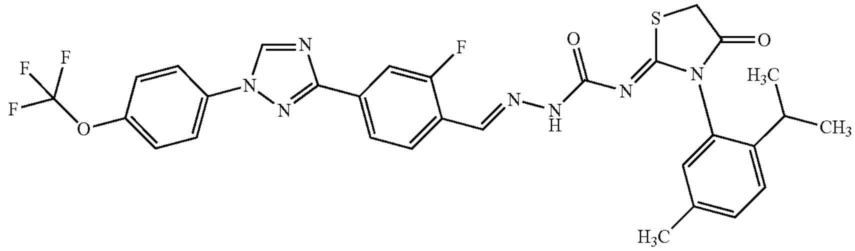 [SMILES: Cc1ccc(C(C)C)c(N2C(=O)CS/C2=N\C(=O)N/N=C/c2ccc(-c3ncn(-c4ccc(OC(F)(F)F)cc4)n3)cc2F)c1] |
| P81 | 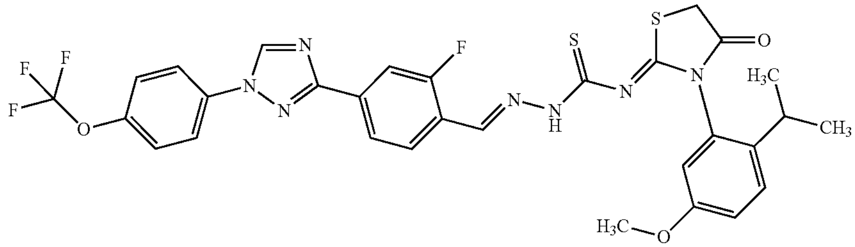 [SMILES: COc1ccc(C(C)C)c(N2C(=O)CS/C2=N\C(=S)N/N=C/c2ccc(-c3ncn(-c4ccc(OC(F)(F)F)cc4)n3)cc2F)c1] |
| P82 | 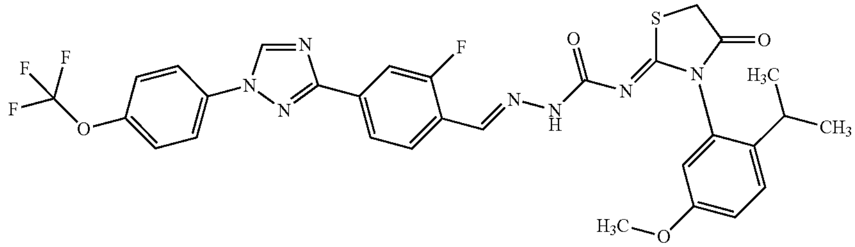 [SMILES: COc1ccc(C(C)C)c(N2C(=O)CS/C2=N\C(=O)N/N=C/c2ccc(-c3ncn(-c4ccc(OC(F)(F)F)cc4)n3)cc2F)c1] |

| Cmpd. No. | Structure |
|---|---|
| P83 | 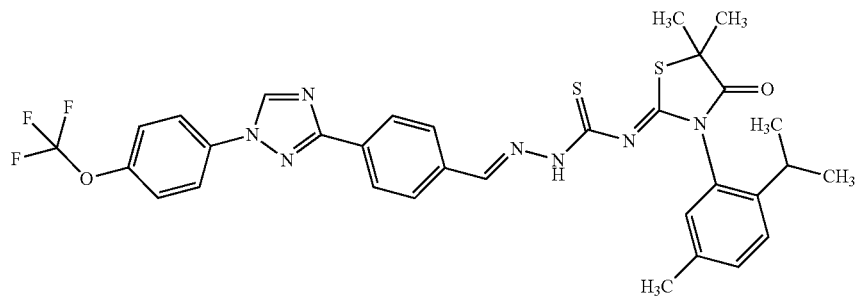 [SMILES: Cc1ccc(C(C)C)c(N2C(=O)C(C)(C)S/C2=N\C(=S)N/N=C/c2ccc(-c3ncn(-c4ccc(OC(F)(F)F)cc4)n3)cc2)c1] |
| P84 | 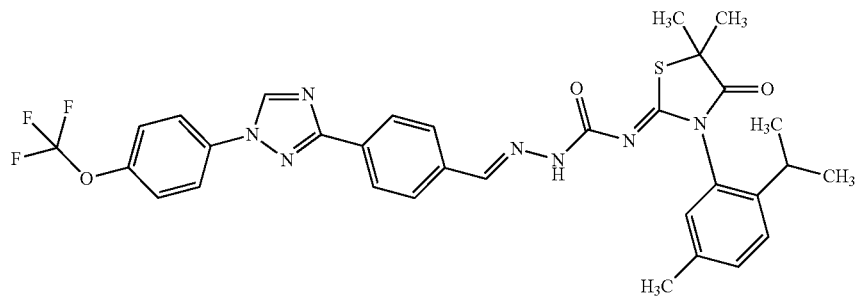 [SMILES: Cc1ccc(C(C)C)c(N2C(=O)C(C)(C)S/C2=N\C(=O)N/N=C/c2ccc(-c3ncn(-c4ccc(OC(F)(F)F)cc4)n3)cc2)c1] |
| P85 | 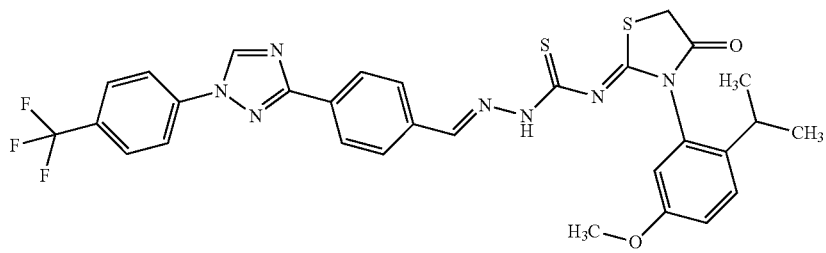 |
| P86 | 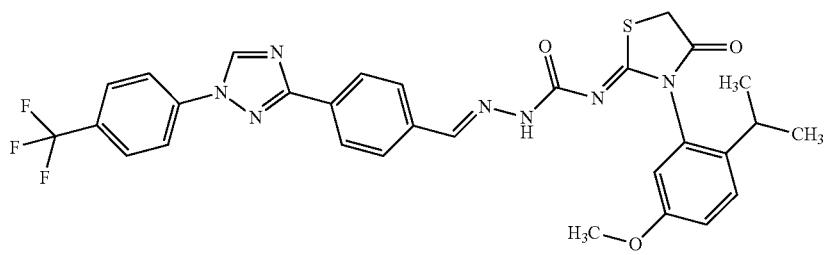 [SMILES: COc1ccc(C(C)C)c(N2C(=O)CS/C2=N\C(=O)N/N=C/c2ccc(-c3ncn(-c4ccc(C(F)(F)F)cc4)n3)cc2)c1] |
| P87 | 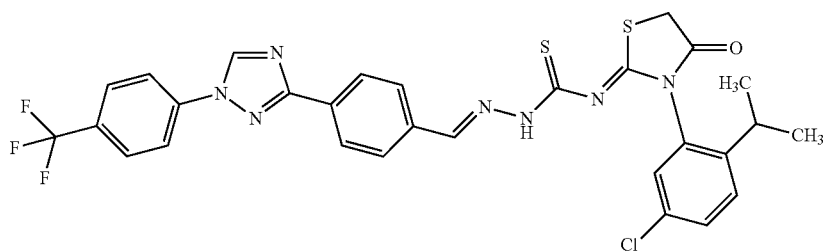 [SMILES: CC(C)c1ccc(Cl)cc1N1C(=O)CS/C1=N\C(=O)N/N=C/c1ccc(-c2ncn(-c3ccc(C(F)(F)F)cc3)n2)cc1] |

-continued

| Cmpd. No. | Structure |
|---|---|
| P88 | 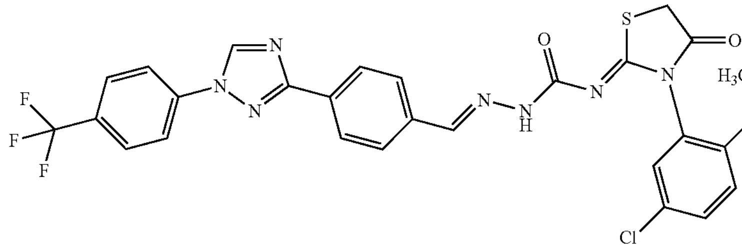 |
| P89 | 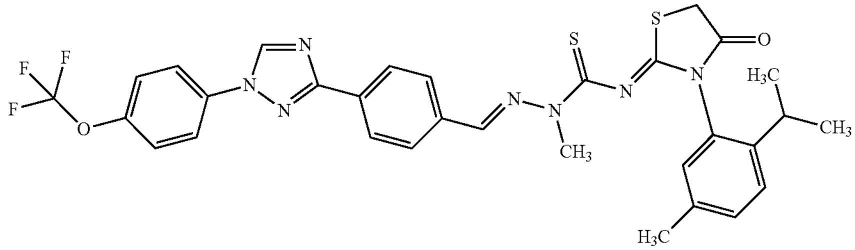 [SMILES: Cc1ccc(C(C)C)c(N2C(=O)CS/C2=N\C(=S)N(C)/N=C/c2ccc(-c3ncn(-c4ccc(OC(F)(F)F)cc4)n3)cc2)c1] |
| P90 | 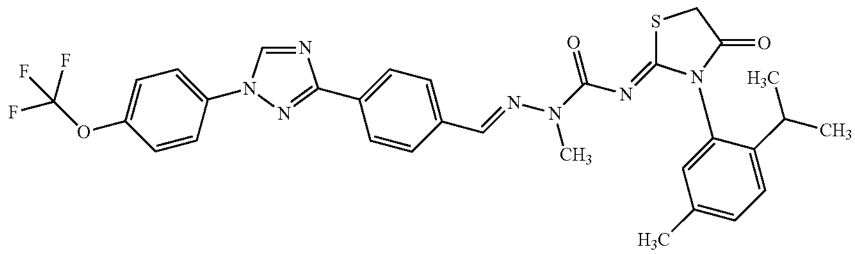 [SMILES: Cc1ccc(C(C)C)c(N2C(=O)CS/C2=N\C(=O)N(C)/N=C/c2ccc(-c3ncn(-c4ccc(OC(F)(F)F)cc4)n3)cc2)c1] |
| P91 | 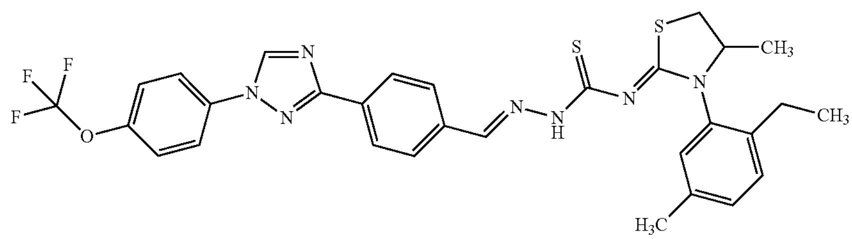 |
| P92 | 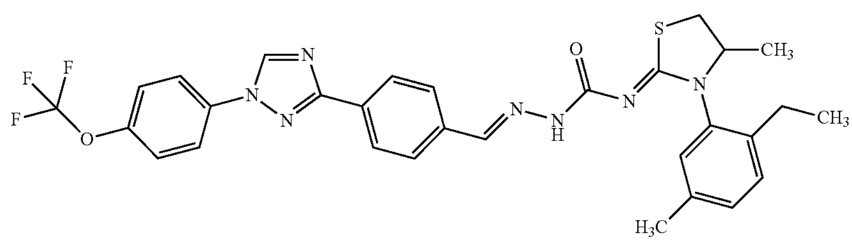 [SMILES: CCc1ccc(C)cc1N1/C(=N/C(=O)N/N=C/c2ccc(-c3ncn(-c4ccc(OC(F)(F)F)cc4)n3)cc2)SCC1C] |
| P93 | 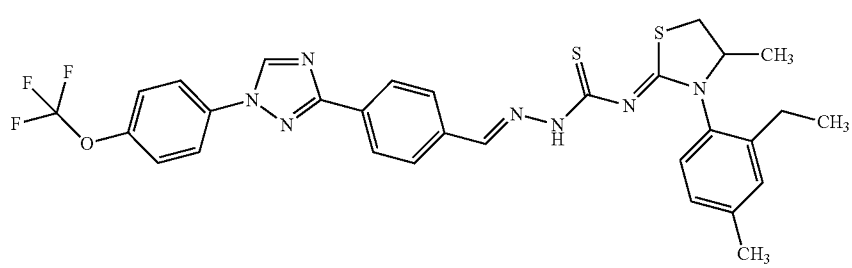 [SMILES: CCc1cc(C)ccc1N1/C(=N/C(=O)N/N=C/c2ccc(-c3ncn(-c4ccc(OC(F)(F)F)cc4)n3)cc2)SCC1C] |

| Cmpd. No. | Structure |
|---|---|
| P94 | 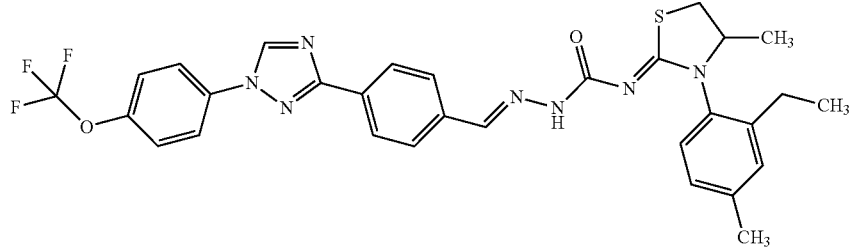 |
| P95 | 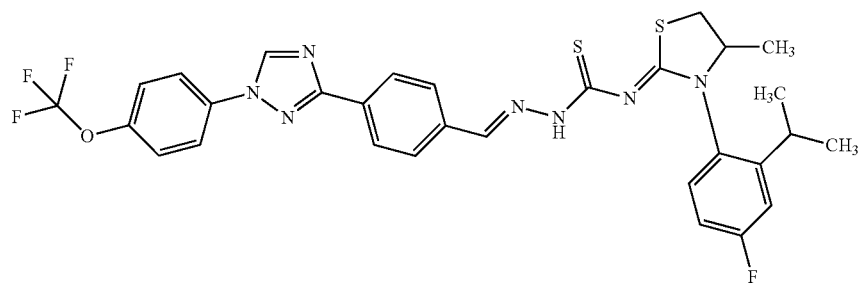 [SMILES: CC(C)c1cc(F)ccc1N1/C(=N/C(=S)N/N=C/c2ccc(-c3ncn(-c4ccc(OC(F)(F)F)cc4)n3)cc2)SCC1C] |
| P96 | 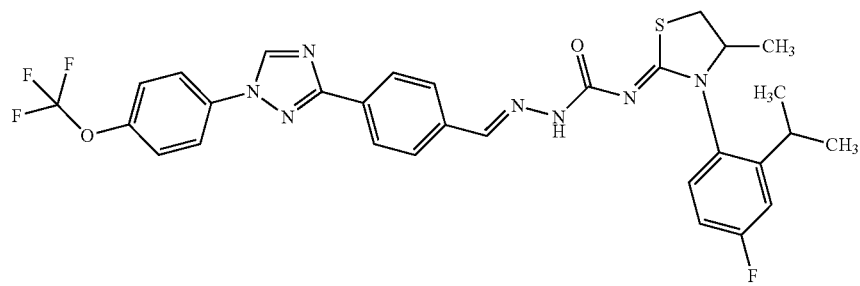 [SMILES: CC(C)c1cc(F)ccc1N1/C(=N/C(=O)N/N=C/c2ccc(-c3ncn(-c4ccc(OC(F)(F)F)cc4)n3)cc2)SCC1C] |
| P97 | 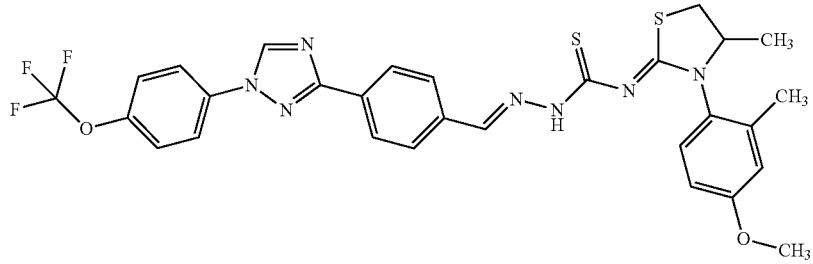 [SMILES: COc1ccc(N2/C(=N/C(=S)N/N=C/c3ccc(-c4ncn(-c5ccc(OC(F)(F)F)cc5)n4)cc3)SCC2C)c(C)c1] |
| P98 | 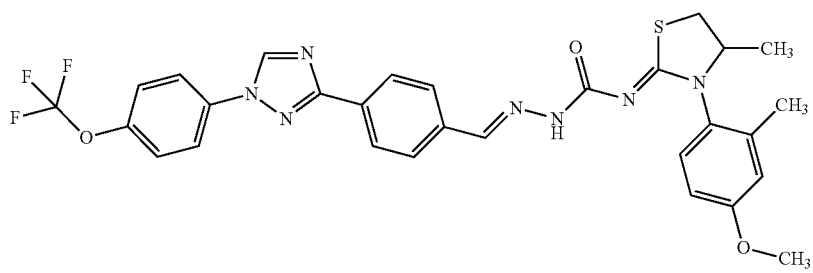 [SMILES: COc1ccc(N2/C(=N/C(=O)N/N=C/c3ccc(-c4ncn(-c5ccc(OC(F)(F)F)cc5)n4)cc3)SCC2C)c(C)c1] |

| Cmpd. No. | Structure |
|---|---|
| P99 | 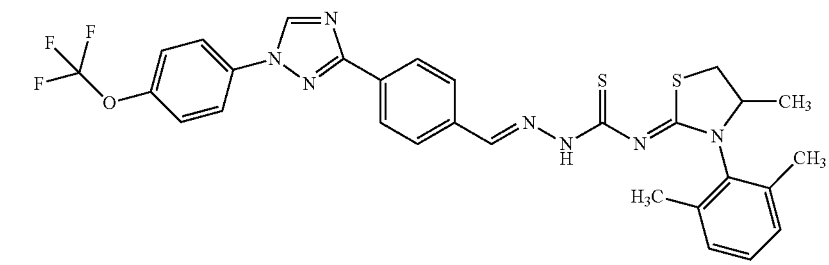 |
| P100 | 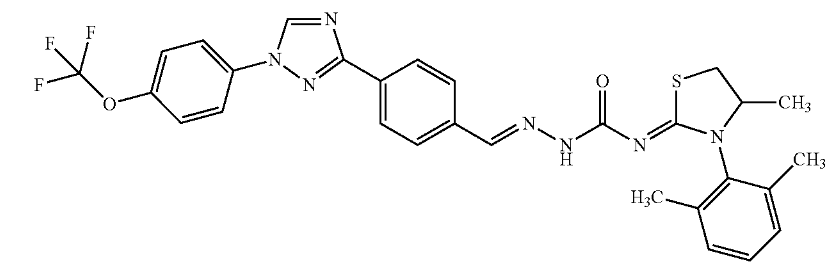 [SMILES: Cc1cccc(C)c1N1/C(=N/C(=O)N/N=C/c2ccc(-c3ncn(-c4ccc(OC(F)(F)F)cc4)n3)cc2)SCC1C] |
| P101 | 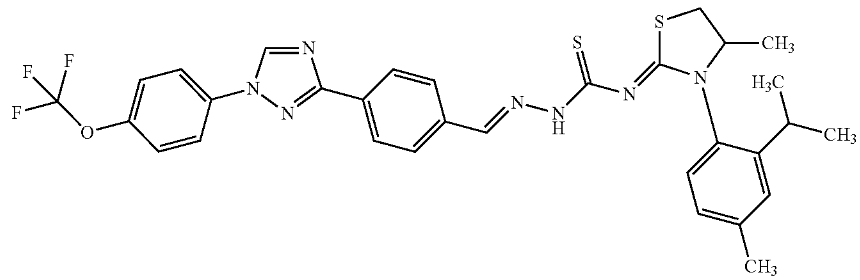 [SMILES: Cc1ccc(N2/C(=N/C(=S)N/N=C/c3ccc(-c4ncn(-c5ccc(OC(F)(F)F)cc5)n4)cc3)SCC2C)c(C(C)C)c1] |
| P102 | 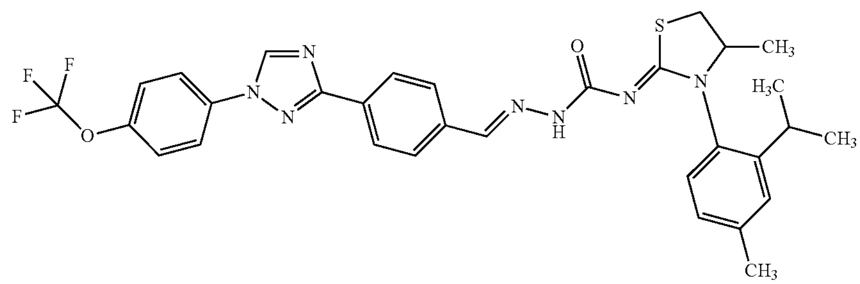 [SMILES: Cc1ccc(N2/C(=N/C(=O)N/N=C/c3ccc(-c4ncn(-c5ccc(OC(F)(F)F)cc5)n4)cc3)SCC2C)c(C(C)C)c1] |
| P103 | 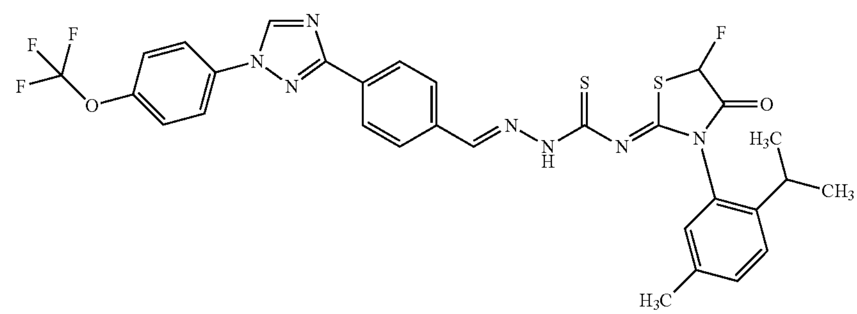 [SMILES: Cc1ccc(C(C)C)c(N2C(=O)C(F)S/C2=N\C(=S)N/N=C/c2ccc(-c3ncn(-c4ccc(OC(F)(F)F)cc4)n3)cc2)c1] |

-continued
| Cmpd. No. | Structure |
|---|---|
| P104 | 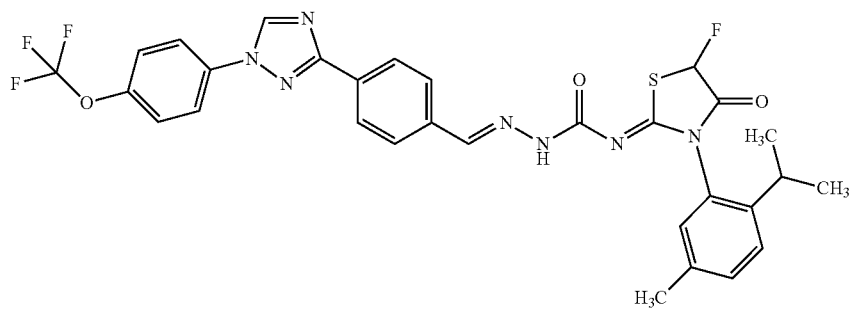 [SMILES: Cc1ccc(C(C)C)c(N2C(=O)C(F)S/C2=N\C(=O)N/N=C/c2ccc(-c3ncn(-c4ccc(OC(F)(F)F)cc4)n3)cc2)c1] |
| P105 | 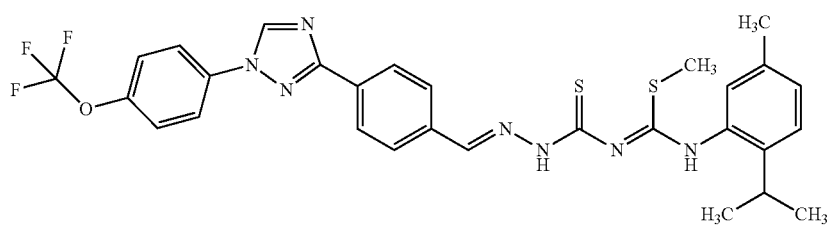 |
| P106 | 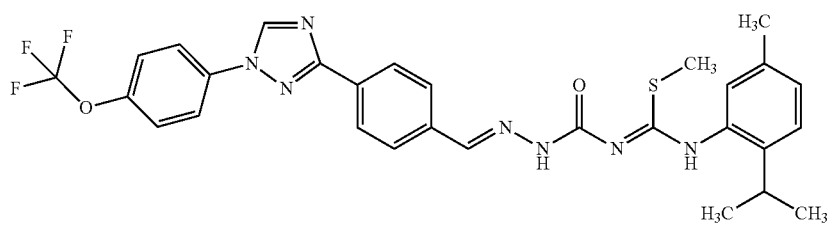 [SMILES: CS/C(=N\C(=O)N/N=C/c1ccc(-c2ncn(-c3ccc(OC(F)(F)F)cc3)n2)cc1)Nc1cc(C)ccc1C(C)C] |
| P107 | 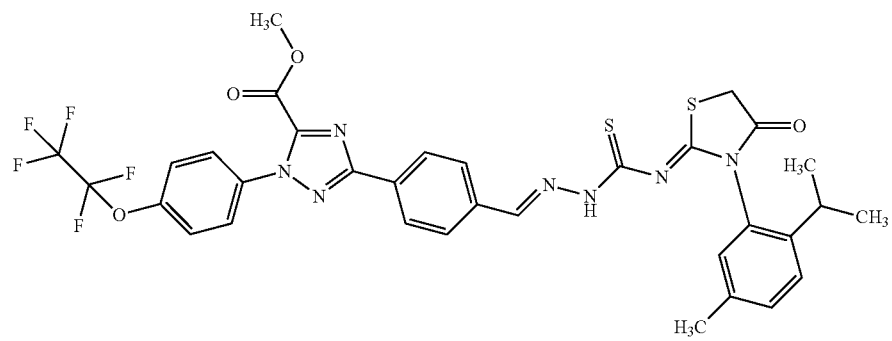 [SMILES: COC(=O)c1nc(-c2ccc(/C=N/NC(=S)/N=C3\SCC(=O)N3c3cc(C)ccc3C(C)C)cc2)nn1-c1ccc(OC(F)(F)C(F)(F)F)cc1] |
| P108 | 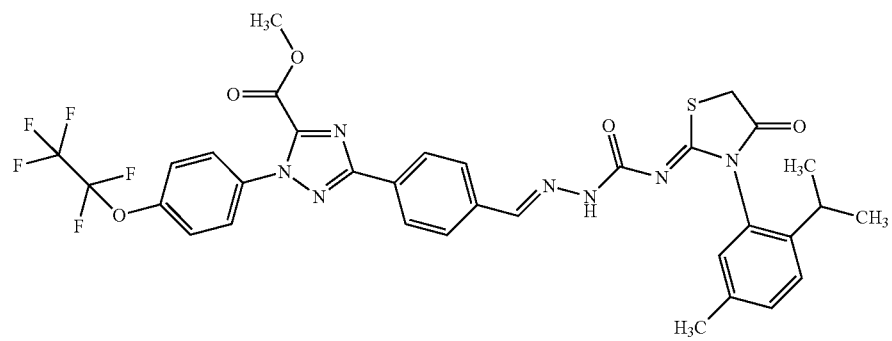 [SMILES: COC(=O)c1nc(-c2ccc(/C=N/NC(=O)/N=C3\SCC(=O)N3c3cc(C)ccc3C(C)C)cc2)nn1-c1ccc(OC(F)(F)C(F)(F)F)cc1] |

-continued
| Cmpd. No. | Structure |
|---|---|
| P109 | 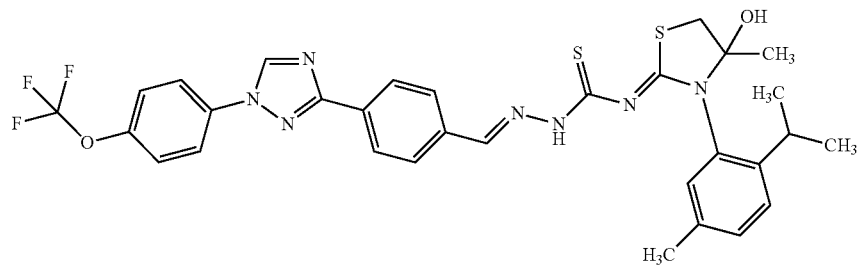 [SMILES: Cc1ccc(C(C)C)c(N2/C(=N/C(=S)N/N=C/c3ccc(-c4ncn(-c5ccc(OC(F)(F)F)cc5)n4)cc3)SCC2(C)O)c1] |
| P110 | 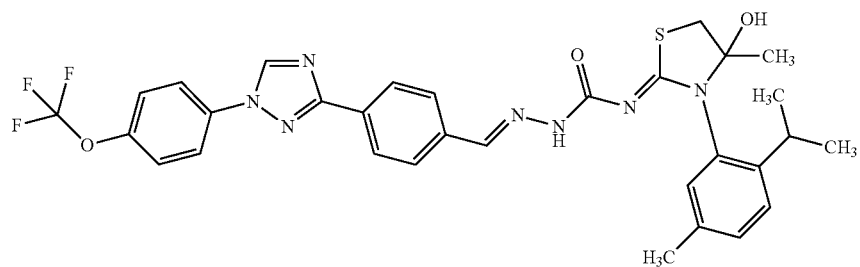 [SMILES: Cc1ccc(C(C)C)c(N2/C(=N/C(=O)N/N=C/c3ccc(-c4ncn(-c5ccc(OC(F)(F)F)cc5)n4)cc3)SCC2(C)O)c1] |
| P111 | 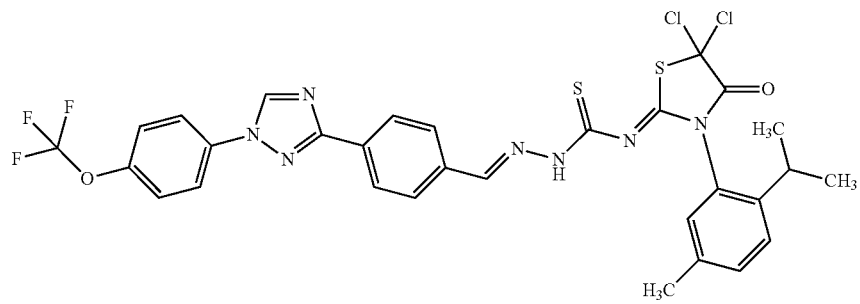 [SMILES: Cc1ccc(C(C)C)c(N2C(=O)C(Cl)(Cl)S/C2=N\C(=S)N/N=C/c2ccc(-c3ncn(-c4ccc(OC(F)(F)F)cc4)n3)cc2)c1] |
| P112 | 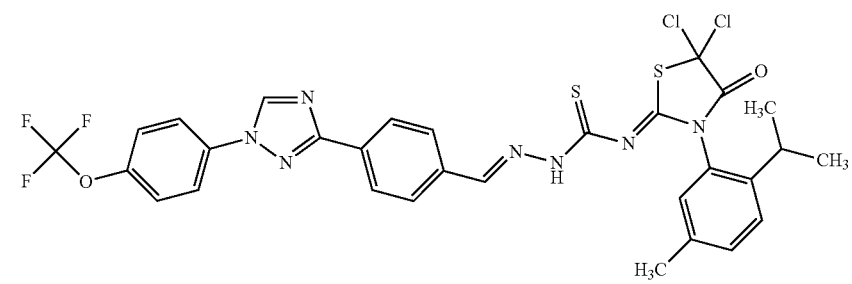 [SMILES: Cc1ccc(C(C)C)c(N2C(=O)C(Cl)(Cl)S/C2=N\C(=S)N/N=C/c2ccc(-c3ncn(-c4ccc(OC(F)(F)F)cc4)n3)cc2)c1] |
| P113 | 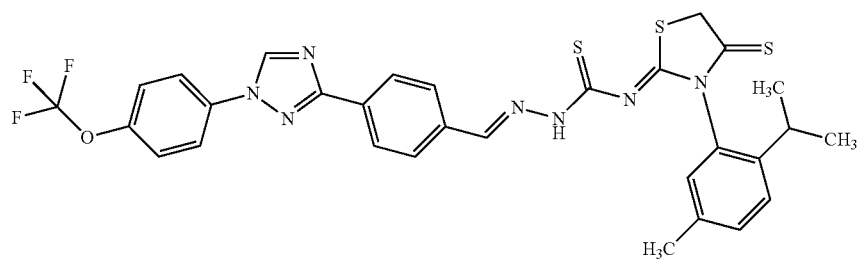 [SMILES: Cc1ccc(C(C)C)c(N2C(=S)CS/C2=N\C(=S)N/N=C/c2ccc(-c3ncn(-c4ccc(OC(F)(F)F)cc4)n3)cc2)c1] |

| Cmpd. No. | Structure |
|---|---|
| P114 | 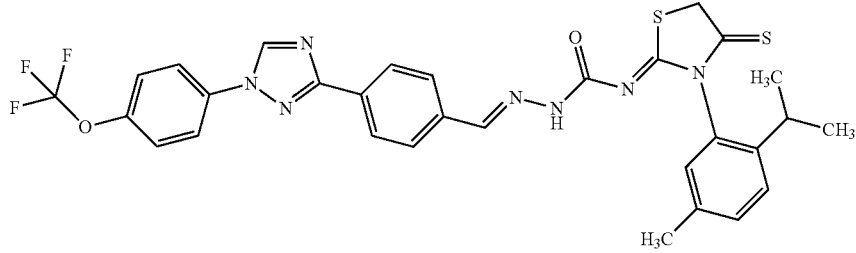 [SMILES: Cc1ccc(C(C)C)c(N2C(=S)CS/C2=N\C(=O)N/N=C/c2ccc(-c3ncn(-c4ccc(OC(F)(F)F)cc4)n3)cc2)c1] |
| P115 | 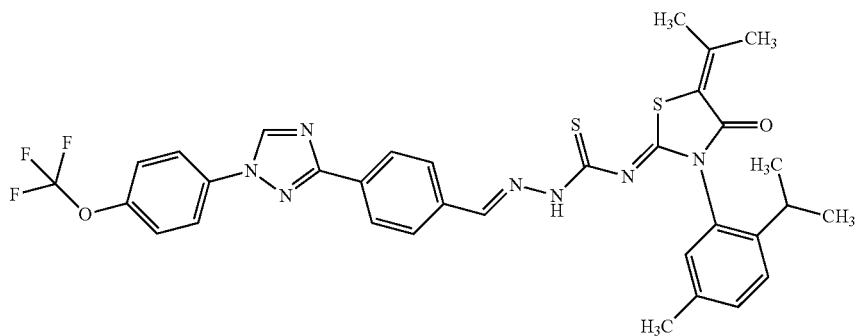 [SMILES: CC(C)=C1S/C(=N\C(=S)N/N=C/c2ccc(-c3ncn(-c4ccc(OC(F)(F)F)cc4)n3)cc2)N(c2cc(C)ccc2C(C)C)C1=O] |
| P116 | 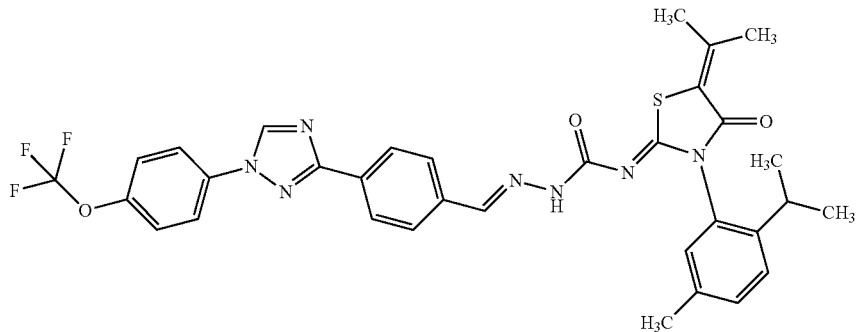 [SMILES: CC(C)=C1S/C(=N\C(=O)N/N=C/c2ccc(-c3ncn(-c4ccc(OC(F)(F)F)cc4)n3)cc2)N(c2cc(C)ccc2C(C)C)C1=O] |
| P117 | 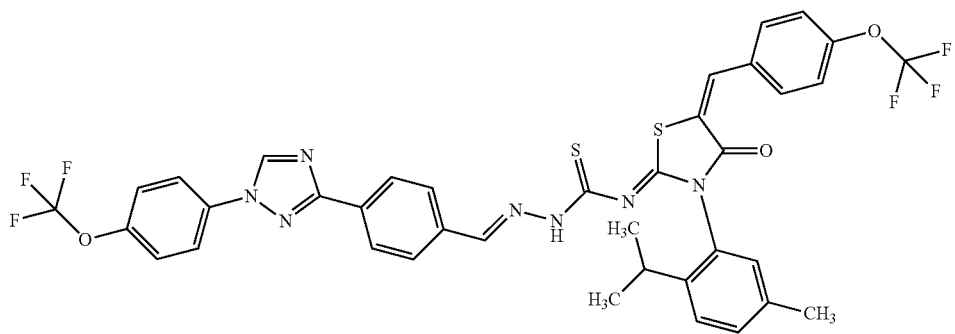 [SMILES: Cc1ccc(C(C)C)c(N2C(=O)/C(=C\c3ccc(OC(F)(F)F)cc3)S/C2=N\C(=S)N/N=C/c2ccc(-c3ncn(-c4ccc(OC(F)(F)F)cc4)n3)cc2)c1] |

-continued
| Cmpd. No. | Structure |
|---|---|
| P118 | 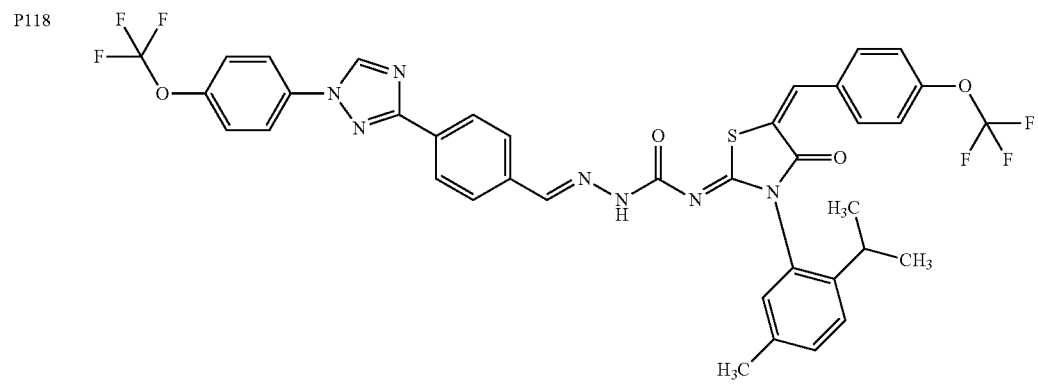 |
| P119 | 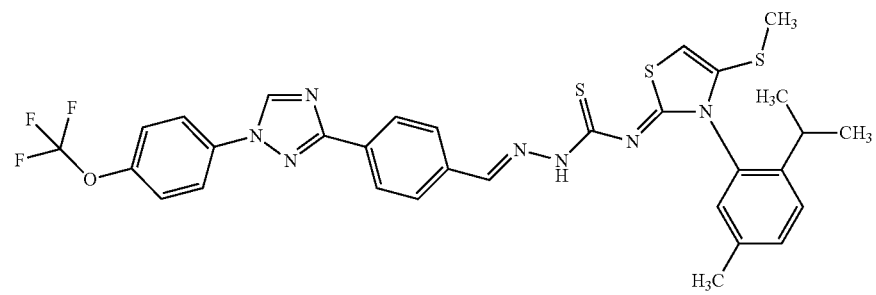 [SMILES: CSc1cs/c(=N\C(=S)N/N=C/c2ccc(-c3ncn(-c4ccc(OC(F)(F)F)cc4)n3)cc2)n1-c1cc(C)ccc1C(C)C] |
| P120 | 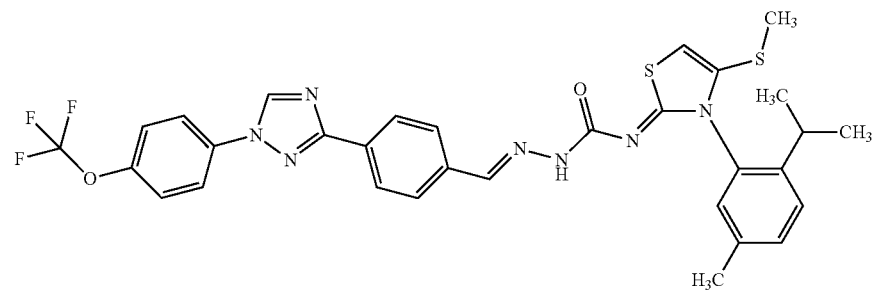 [SMILES: CSc1cs/c(=N\C(=O)N/N=C/c2ccc(-c3ncn(-c4ccc(OC(F)(F)F)cc4)n3)cc2)n1-c1cc(C)ccc1C(C)C] |
| P121 | 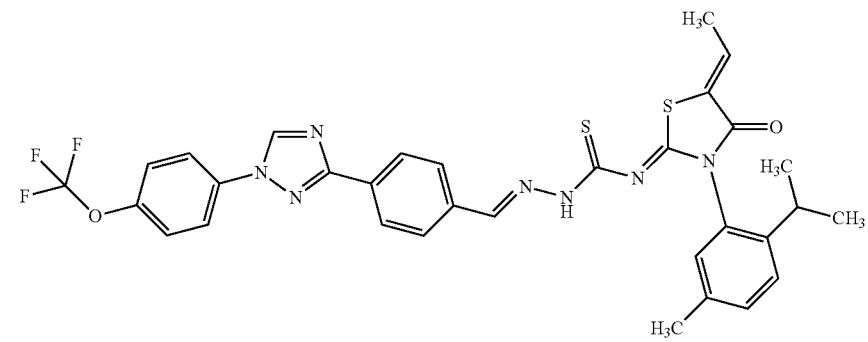 [SMILES: C/C=C1\S/C(=N\C(=S)N/N=C/c2ccc(-c3ncn(-c4ccc(OC(F)(F)F)cc4)n3)cc2)N(c2cc(C)ccc2C(C)C)C1=O] |

-continued

| Cmpd. No. | Structure |
|---|---|
| P122 | 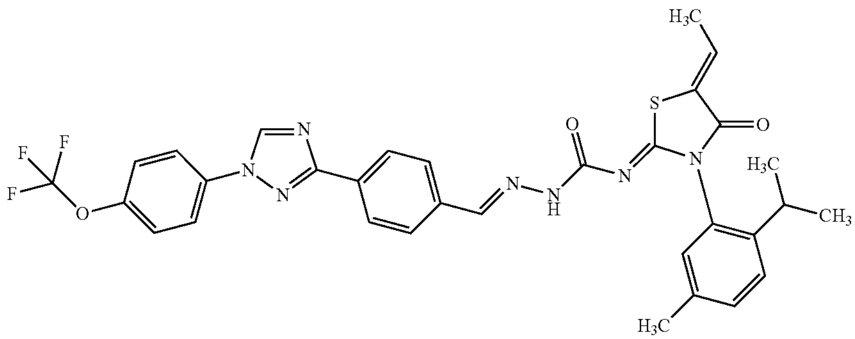 [SMILES: C/C=C1\S/C(=N\C(=O)N/N=C/c2ccc(-c3ncn(-c4ccc(OC(F)(F)F)cc4)n3)cc2)N(c2cc(C)ccc2C(C)C)C1=O] |
| P123 | 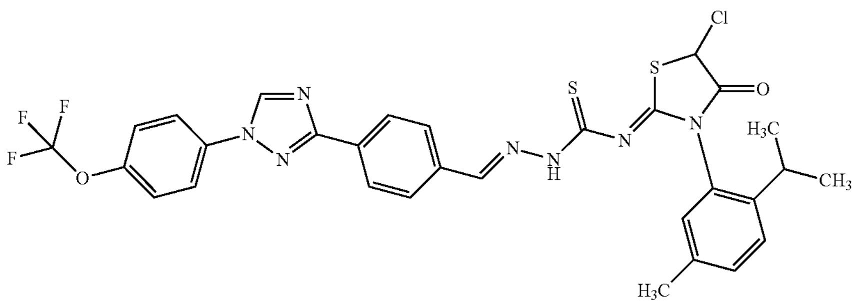 [SMILES: Cc1ccc(C(C)C)c(N2C(=O)C(Cl)S/C2=N\C(=S)N/N=C/c2ccc(-c3ncn(-c4ccc(OC(F)(F)F)cc4)n3)cc2)c1] |
| P124 | 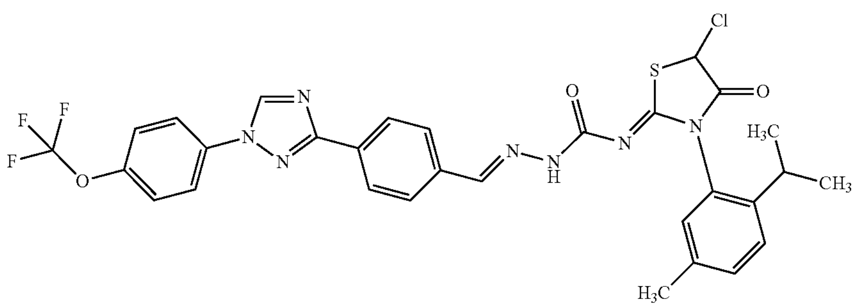 [SMILES: Cc1ccc(C(C)C)c(N2C(=O)C(Cl)S/C2=N\C(=O)N/N=C/c2ccc(-c3ncn(-c4ccc(OC(F)(F)F)cc4)n3)cc2)c1] |
| P125 | 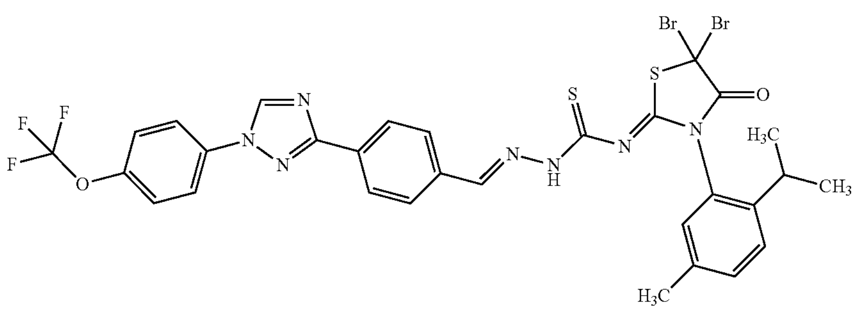 [SMILES: Cc1ccc(C(C)C)c(N2C(=O)C(Br)(Br)S/C2=N\C(=S)N/N=C/c2ccc(-c3ncn(-c4ccc(OC(F)(F)F)cc4)n3)cc2)c1] |
| P126 | 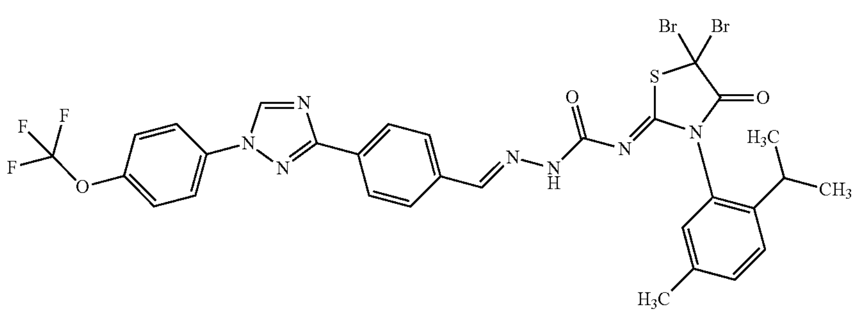 [SMILES: Cc1ccc(C(C)C)c(N2C(=O)C(Br)(Br)S/C2=N\C(=O)N/N=C/c2ccc(-c3ncn(-c4ccc(OC(F)(F)F)cc4)n3)cc2)c1] |

-continued
| Cmpd. No. | Structure |
|---|---|
| P127 | 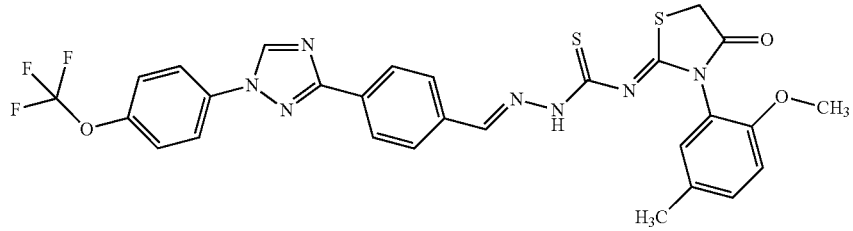 [SMILES: COc1ccc(C)cc1N1C(=O)CS/C1=N\C(=S)N/N=C/c1ccc(-c2ncn(-c3ccc(OC(F)(F)F)cc3)n2)cc1] |
| P128 | 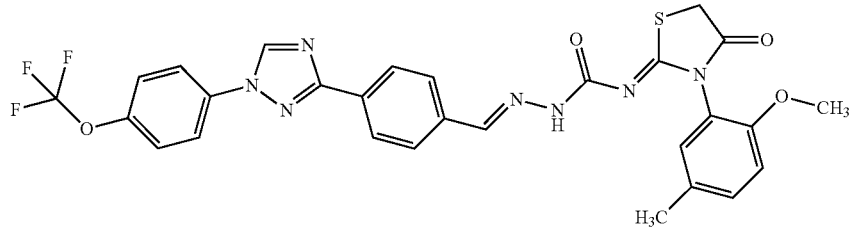 [SMILES: COc1ccc(C)cc1N1C(=O)CS/C1=N\C(=O)N/N=C/c1ccc(-c2ncn(-c3ccc(OC(F)(F)F)cc3)n2)cc1] |
| P129 | 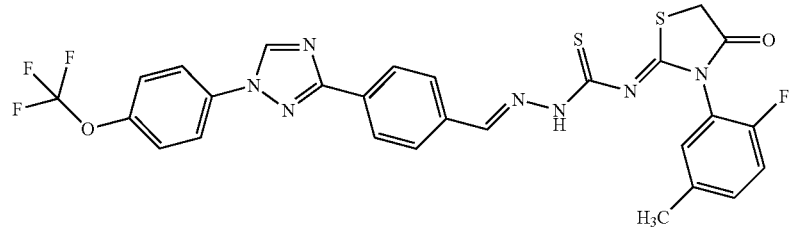 [SMILES: Cc1ccc(F)c(N2C(=O)CS/C2=N\C(=S)N/N=C/c2ccc(-c3ncn(-c4ccc(OC(F)(F)F)cc4)n3)cc2)c1] |
| P130 | 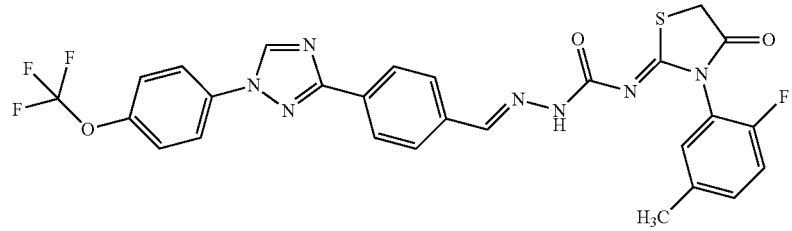 |
| P131 | 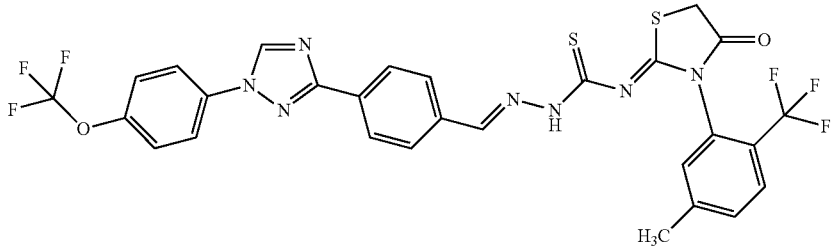 [SMILES: Cc1ccc(C(F)(F)F)c(N2C(=O)CS/C2=N\C(=S)N/N=C/c2ccc(-c3ncn(-c4ccc(OC(F)(F)F)cc4)n3)cc2)c1] |
| P132 | 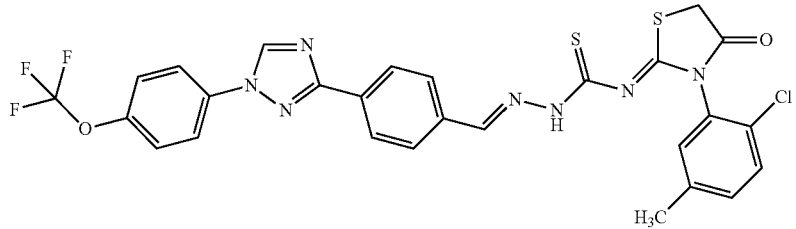 [SMILES: Cc1ccc(Cl)c(N2C(=O)CS/C2=N\C(=S)N/N=C/c2ccc(-c3ncn(-c4ccc(OC(F)(F)F)cc4)n3)cc2)c1] |

| Cmpd. No. | Structure |
|---|---|
| P133 | 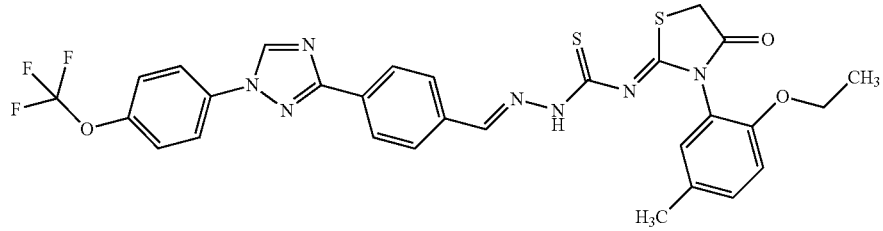 [SMILES: CCOc1ccc(C)cc1N1C(=O)CS/C1=N\C(=S)N/N=C/c1ccc(-c2ncn(-c3ccc(OC(F)(F)F)cc3)n2)cc1] |
| P134 | 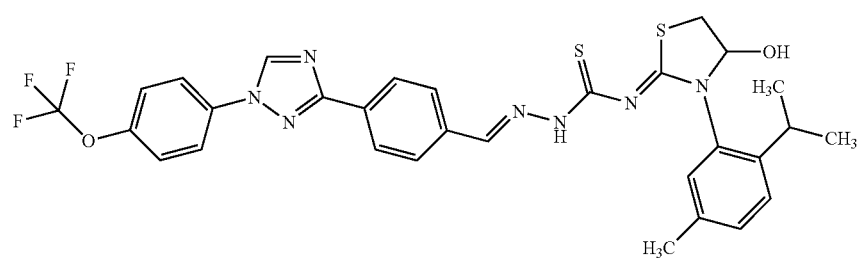 [SMILES: Cc1ccc(C(C)C)c(N2/C(=N/C(=S)N/N=C/c3ccc(-c4ncn(-c5ccc(OC(F)(F)F)cc5)n4)cc3)SCC2O)c1] |
| P135 | 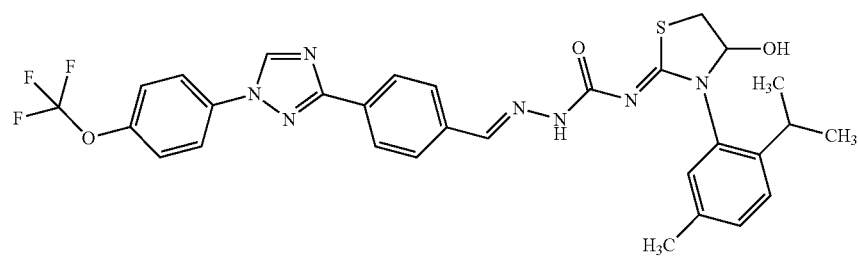 [SMILES: Cc1ccc(C(C)C)c(N2/C(=N/C(=O)N/N=C/c3ccc(-c4ncn(-c5ccc(OC(F)(F)F)cc5)n4)cc3)SCC2O)c1] |
| P136 | 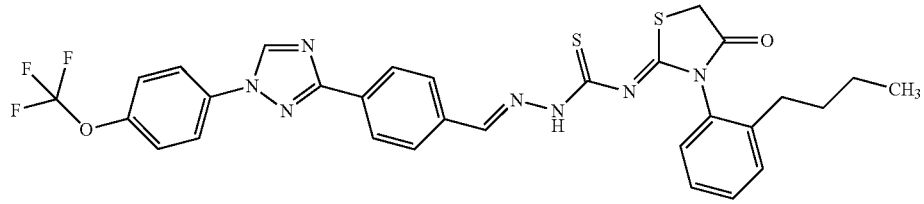 |
| P137 | 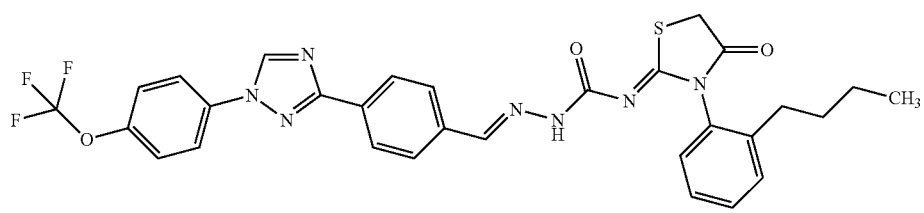 [SMILES: CCCCc1ccccc1N1C(=O)CS/C1=N\C(=S)N/N=C/c1ccc(-c2ncn(-c3ccc(OC(F)(F)F)cc3)n2)cc1] |
| P138 | 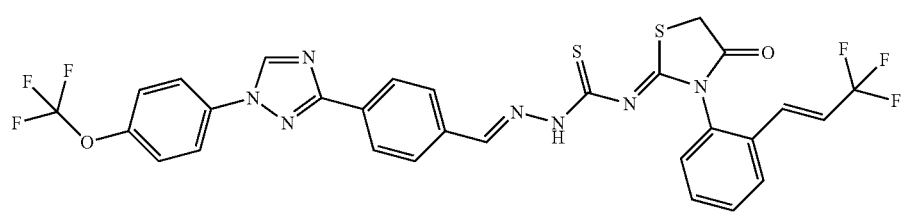 |

-continued
| Cmpd. No. | Structure |
|---|---|
| P139 | 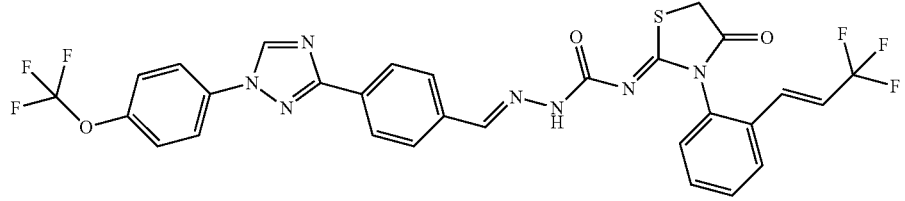 [SMILES: O=C(/N=C1\SCC(=O)N1c1ccccc1/C=C/C(F)(F)F)N/N=C/c1ccc(-c2ncn(-c3ccc(OC(F)(F)F)cc3)n2)cc1] |
| P140 | 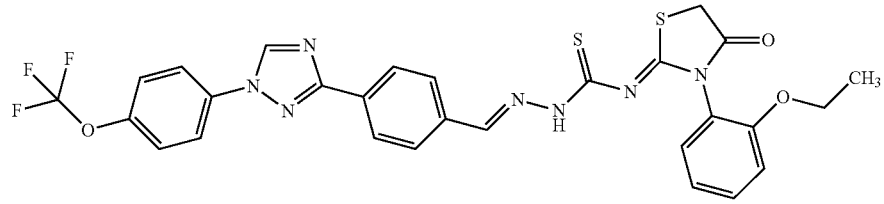 [SMILES: CCOc1ccccc1N1C(=O)CS/C1=N\C(=S)N/N=C/c1ccc(-c2ncn(-c3ccc(OC(F)(F)F)cc3)n2)cc1] |
| P141 | 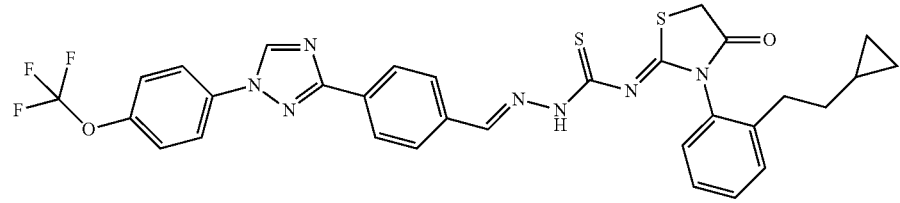 [SMILES: O=C(/N=C1\SCC(=O)N1c1ccccc1CCC1CC1)N/N=C/c1ccc(-c2ncn(-c3ccc(OC(F)(F)F)cc3)n2)cc1] |
| P142 | 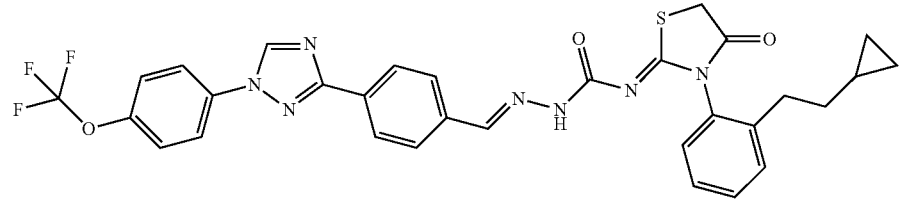 |
| P143 | 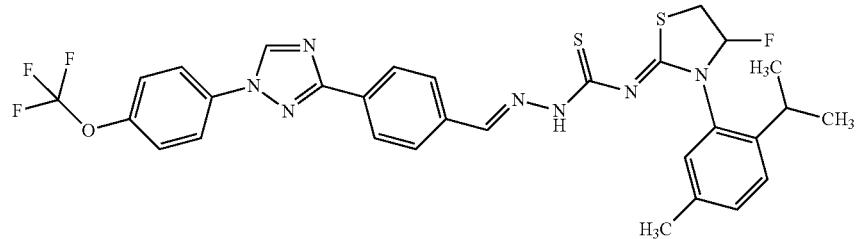 [SMILES: Cc1ccc(C(C)C)c(N2/C(=N/C(=S)N/N=C/c3ccc(-c4ncn(-c5ccc(OC(F)(F)F)cc5)n4)cc3)SCC2F)c1] |
| P144 | 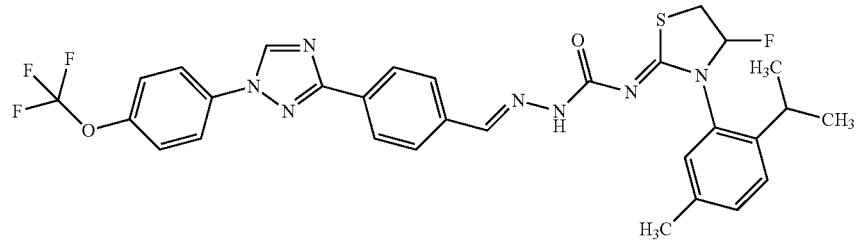 [SMILES: Cc1ccc(C(C)C)c(N2/C(=N/C(=O)N/N=C/c3ccc(-c4ncn(-c5ccc(OC(F)(F)F)cc5)n4)cc3)SCC2F)c1] |

-continued

| Cmpd. No. | Structure |
|---|---|
| P145 | 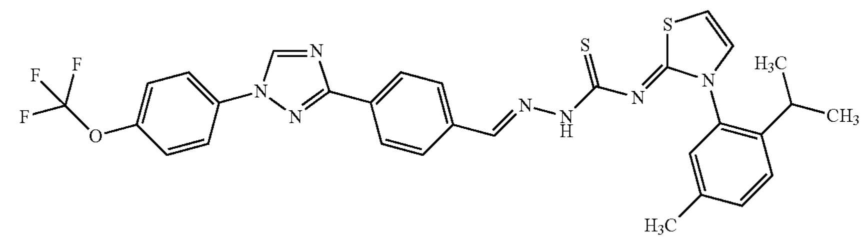 |
| P146 | 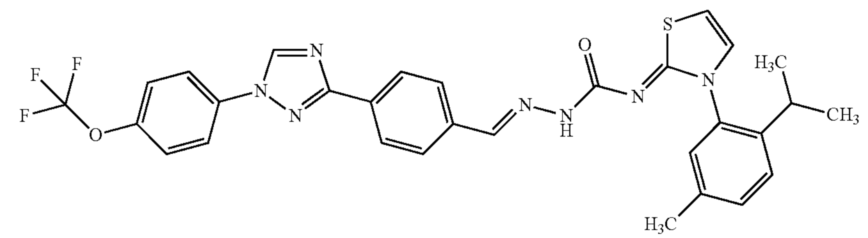 [SMILES: Cc1ccc(C(C)C)c(-n2ccs/c2=N\C(=O)N/N=C/c2ccc(-c3ncn(-c4ccc(OC(F)(F)F)cc4)n3)cc2)c1] |
| P147 | 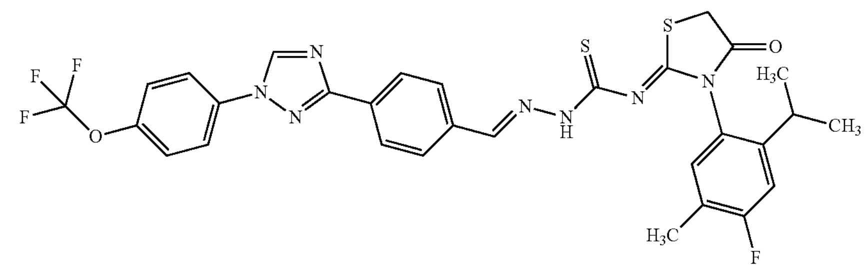 [SMILES: Cc1cc(N2C(=O)CS/C2=N\C(=S)N/N=C/c2ccc(-c3ncn(-c4ccc(OC(F)(F)F)cc4)n3)cc2)c(C(C)C)cc1F] |
| P148 | 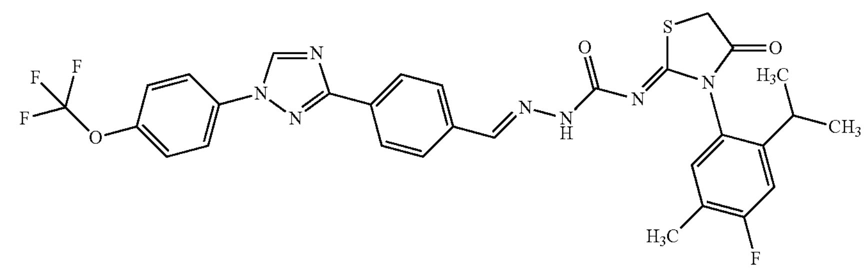 [SMILES: Cc1cc(N2C(=O)CS/C2=N\C(=O)N/N=C/c2ccc(-c3ncn(-c4ccc(OC(F)(F)F)cc4)n3)cc2)c(C(C)C)cc1F] |
| P149 | 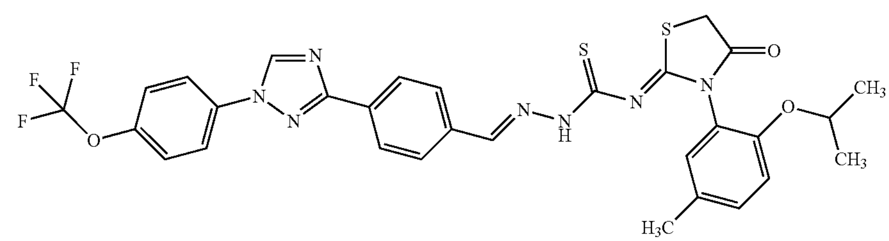 [SMILES: Cc1ccc(OC(C)C)c(N2C(=O)CS/C2=N\C(=S)N/N=C/c2ccc(-c3ncn(-c4ccc(OC(F)(F)F)cc4)n3)cc2)c1] |
| P150 | 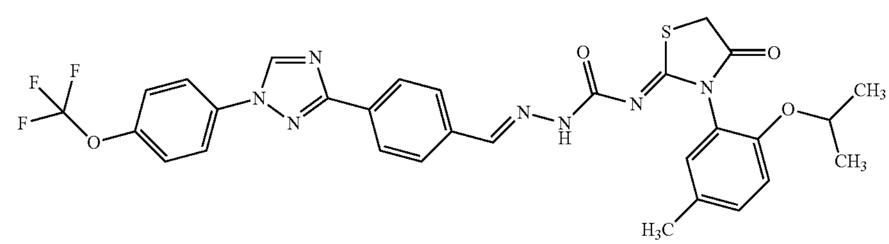 [SMILES: Cc1ccc(OC(C)C)c(N2C(=O)CS/C2=N\C(=O)N/N=C/c2ccc(-c3ncn(-c4ccc(OC(F)(F)F)cc4)n3)cc2)c1] |

-continued
| Cmpd. No. | Structure |
|---|---|
| P151 | 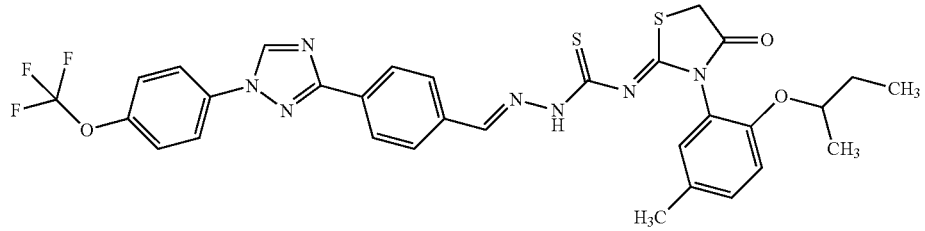 |
| P152 | 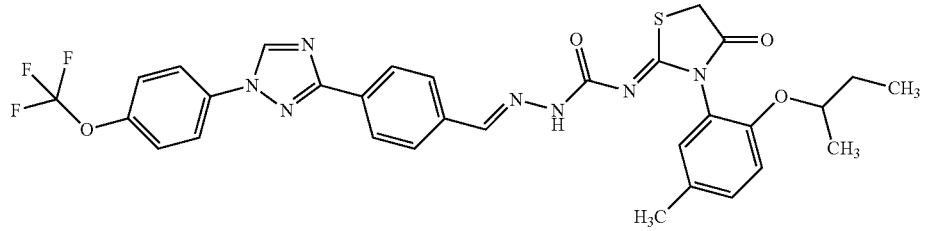 [SMILES: CCC(C)Oc1ccc(C)cc1N1C(=O)CS/C1=N\C(=O)N/N=C/c1ccc(-c2ncn(-c3ccc(OC(F)(F)F)cc3)n2)cc1] |
| P153 | 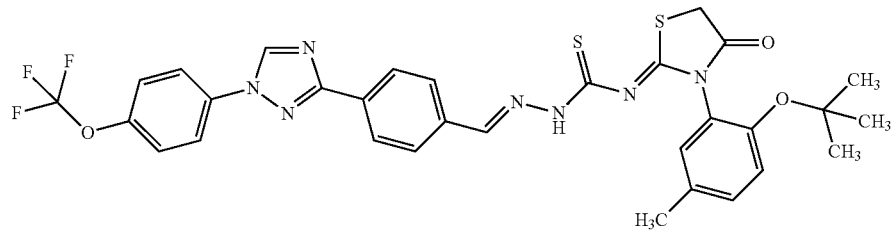 |
| P154 | 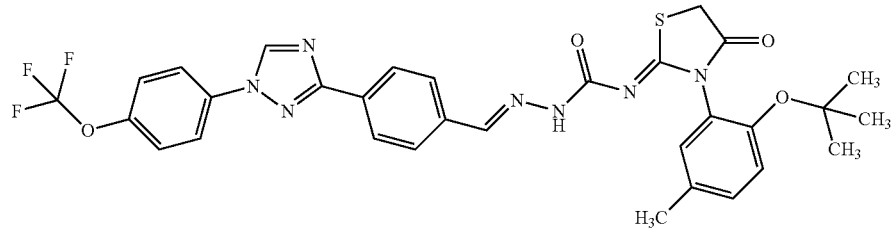 [SMILES: Cc1ccc(OC(C)(C)C)c(N2C(=O)CS/C2=N\C(=O)N/N=C/c2ccc(-c3ncn(-c4ccc(OC(F)(F)F)cc4)n3)cc2)c1] |
| P155 | 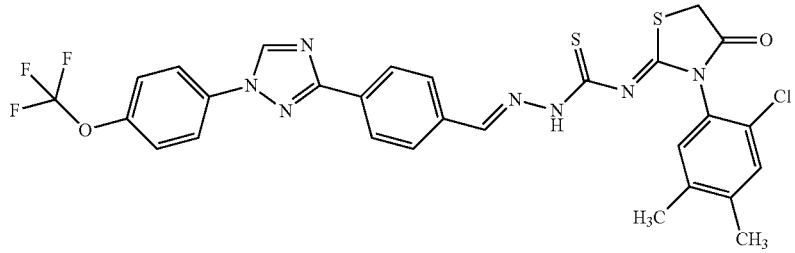 |
| P156 | 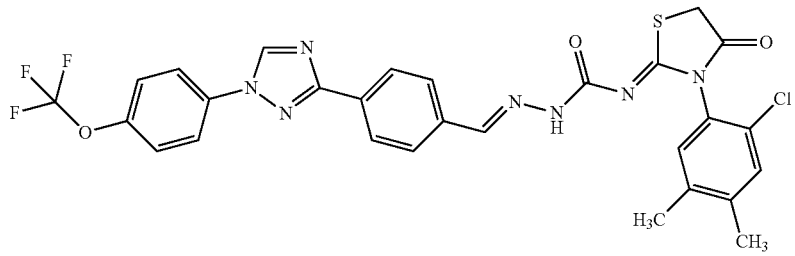 [SMILES: Cc1cc(Cl)c(N2C(=O)CS/C2=N\C(=O)N/N=C/c2ccc(-c3ncn(-c4ccc(OC(F)(F)F)cc4)n3)cc2)cc1C] |

| Cmpd. No. | Structure |
|---|---|
| P157 | 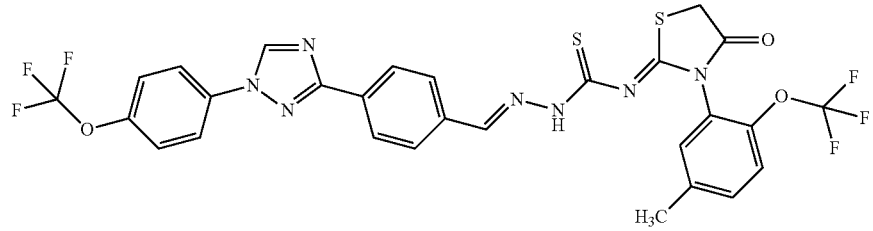 [SMILES: Cc1ccc(OC(F)(F)F)c(N2C(=O)CS/C2=N\C(=O)N/N=C/c2ccc(-c3ncn(-c4ccc(OC(F)(F)F)cc4)n3)cc2)c1] |
| P158 | 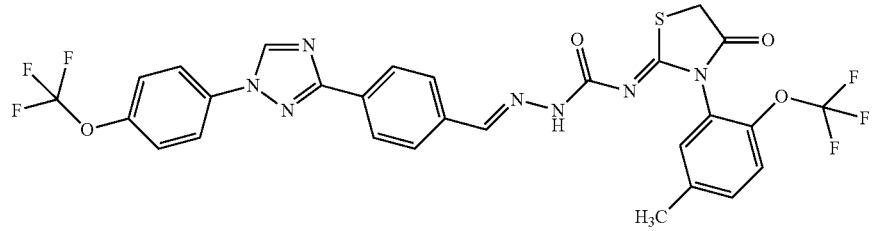 |
| P159 | 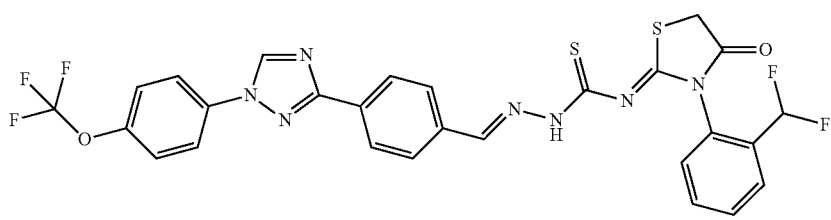 |
| P160 | 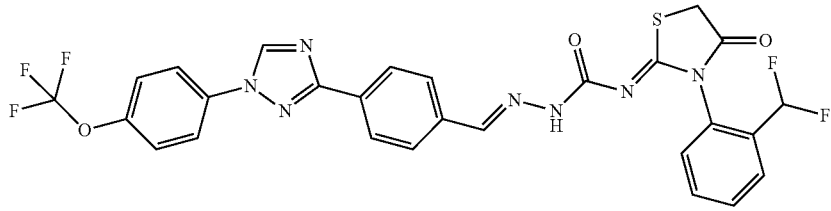 [SMILES: O=C(/N=C1\SCC(=O)N1c1ccccc1C(F)F)N/N=C/c1ccc(-c2ncn(-c3ccc(OC(F)(F)F)cc3)n2)cc1] |
| P161 | 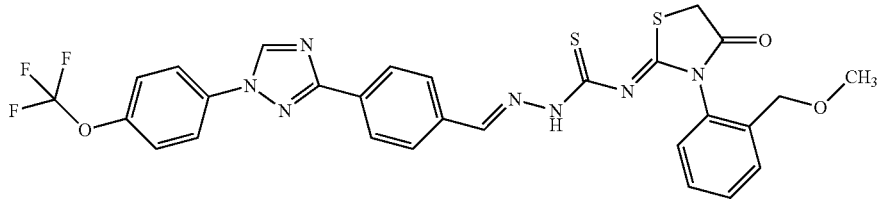 [SMILES: COCc1ccccc1N1C(=O)CS/C1=N\C(=O)N/N=C/c1ccc(-c2ncn(-c3ccc(OC(F)(F)F)cc3)n2)cc1] |
| P162 | 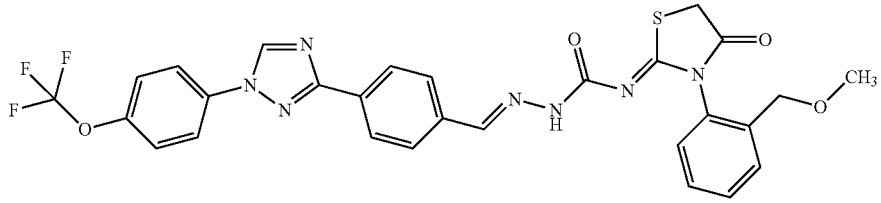 |
| P163 | 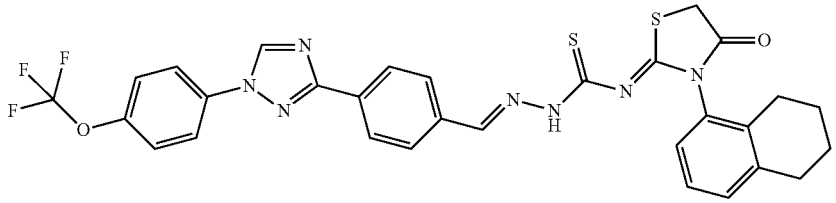 |

-continued
| Cmpd. No. | Structure |
|---|---|
| P164 | 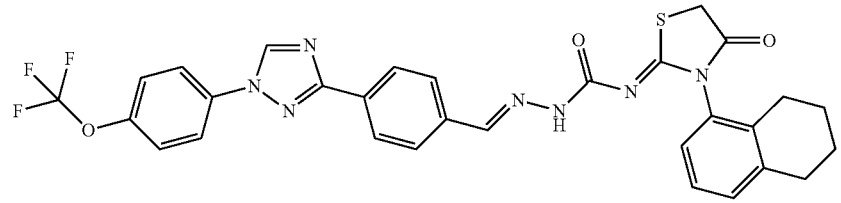 [SMILES: O=C(/N=C1\SCC(=O)N1c1cccc2c1CCCC2)N/N=C/c1ccc(-c2ncn(-c3ccc(OC(F)(F)F)cc3)n2)cc1] |
| P165 | 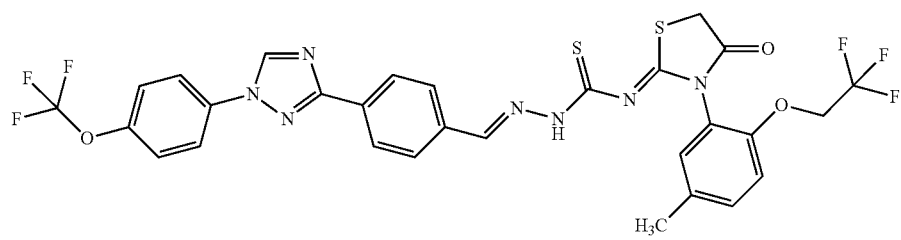 [SMILES: Cc1ccc(OCC(F)(F)F)c(N2C(=O)CS/C2=N\C(=S)N/N=C/c2ccc(-c3ncn(-c4ccc(OC(F)(F)F)cc4)n3)cc2)c1] |
| P166 | 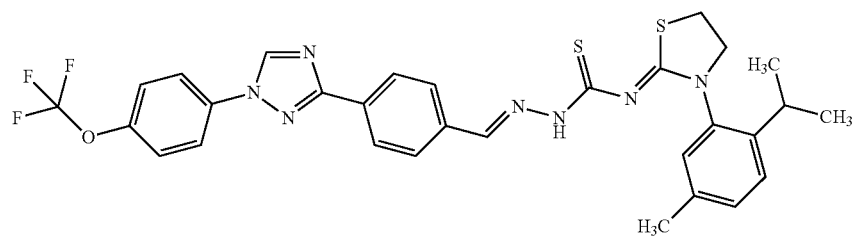 [SMILES: Cc1ccc(C(C)C)c(N2CCS/C2=N\C(=S)N/N=C/c2ccc(-c3ncn(-c4ccc(OC(F)(F)F)cc4)n3)cc2)c1] |
| P167 | 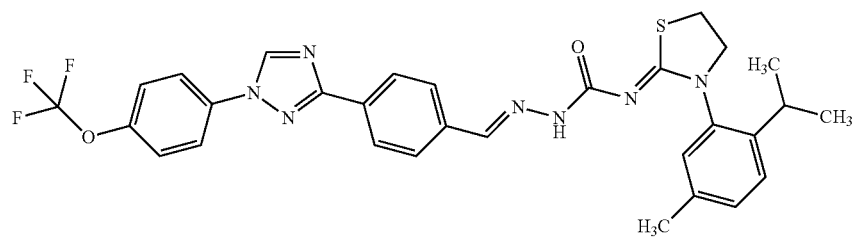 [SMILES: Cc1ccc(C(C)C)c(N2CCS/C2=N\C(=O)N/N=C/c2ccc(-c3ncn(-c4ccc(OC(F)(F)F)cc4)n3)cc2)c1] |
| P168 | 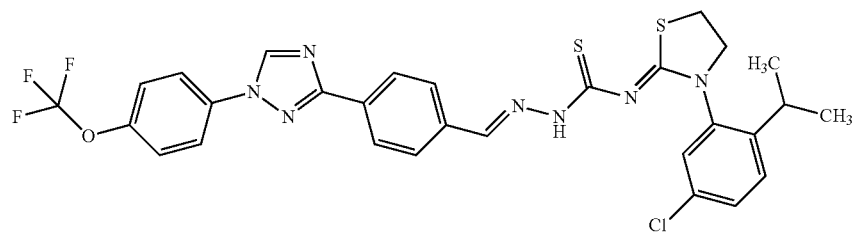 [SMILES: CC(C)c1ccc(Cl)cc1N1CCS/C1=N\C(=S)N/N=C/c1ccc(-c2ncn(-c3ccc(OC(F)(F)F)cc3)n2)cc1] |
| P169 | 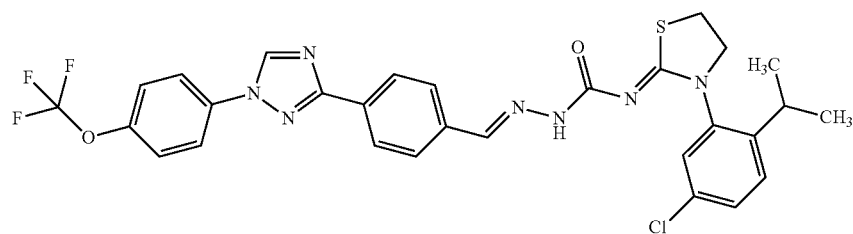 |

| Cmpd. No. | Structure |
|---|---|
| P170 | 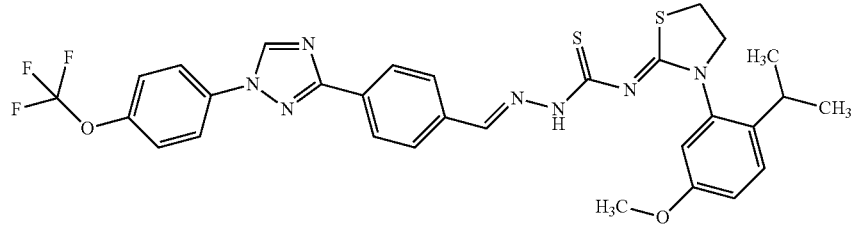 [SMILES: COc1ccc(C(C)C)c(N2CCS/C2=N\C(=S)N/N=C/c2ccc(-c3ncn(-c4ccc(OC(F)(F)F)cc4)n3)cc2)c1] |
| P171 | 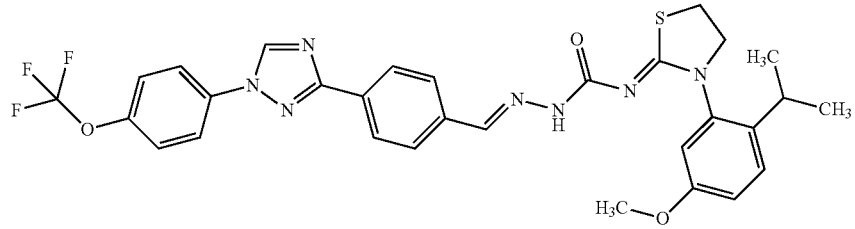 [SMILES: COc1ccc(C(C)C)c(N2CCS/C2=N\C(=O)N/N=C/c2ccc(-c3ncn(-c4ccc(OC(F)(F)F)cc4)n3)cc2)c1] |
| P172 | 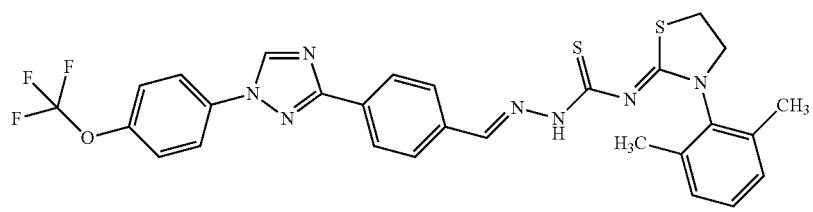 |
| P173 | 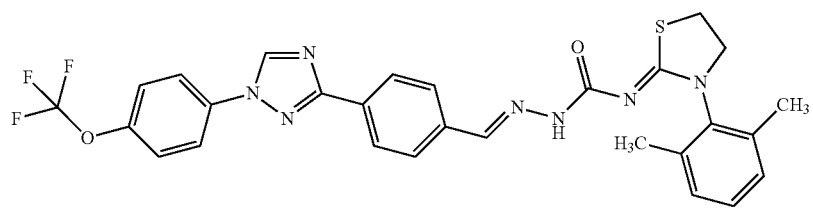 [SMILES: Cc1cccc(C)c1N1CCS/C1=N\C(=O)N/N=C/c1ccc(-c2ncn(-c3ccc(OC(F)(F)F)cc3)n2)cc1] |
| P174 | 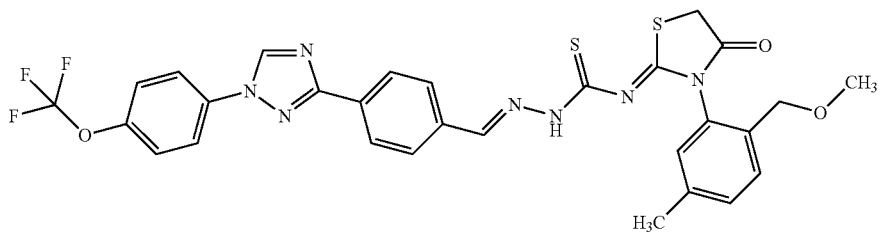 |
| P175 | 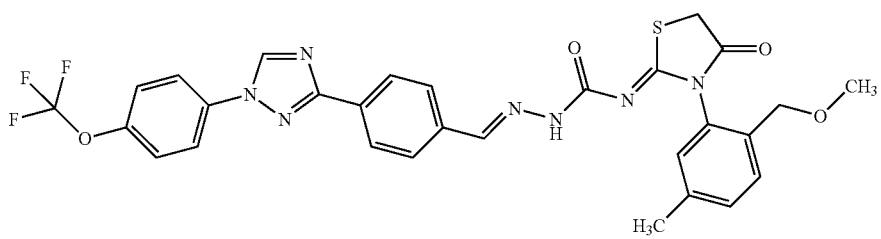 |

-continued
| Cmpd. No. | Structure |
|---|---|
| P176 | 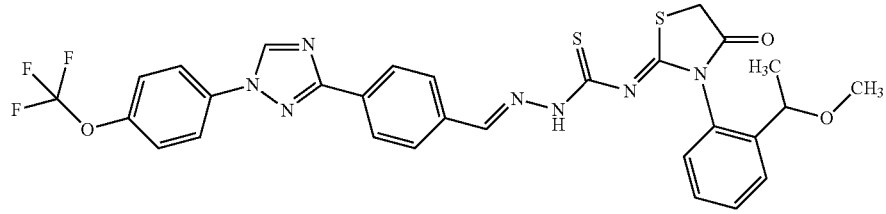 |
| P177 | 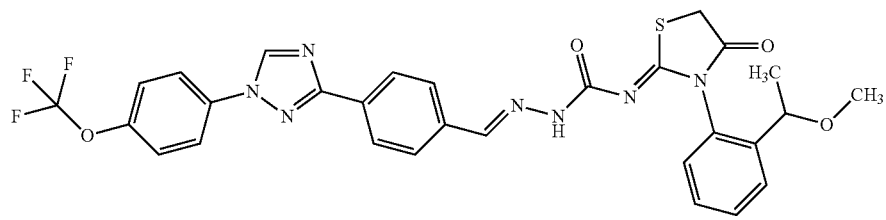 [SMILES: COC(C)c1ccccc1N1C(=O)CS/C1=N\C(=O)N/N=C/c1ccc(-c2ncn(-c3ccc(OC(F)(F)F)cc3)n2)cc1] |
| P178 | 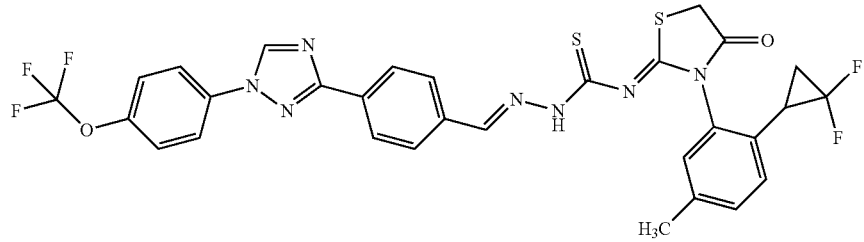 |
| P179 | 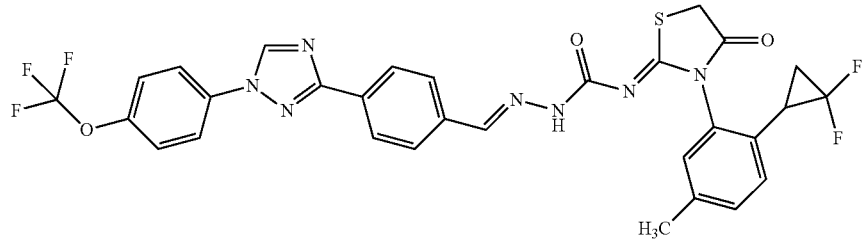 [SMILES: Cc1ccc(C2CC2(F)F)c(N2C(=O)CS/C2=N\C(=O)N/N=C/c2ccc(-c3ncn(-c4ccc(OC(F)(F)F)cc4)n3)cc2)c1] |
| P180 | 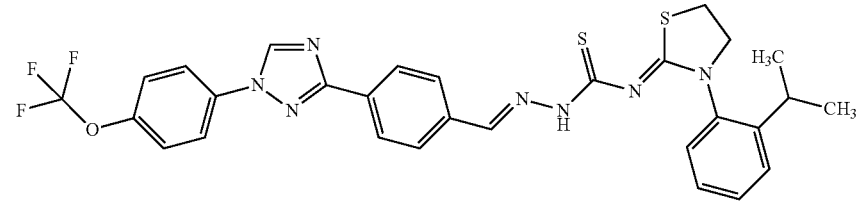 [SMILES: CC(C)c1ccccc1N1CCS/C1=N\C(=S)N/N=C/c1ccc(-c2ncn(-c3ccc(OC(F)(F)F)cc3)n2)cc1] |
| P181 | 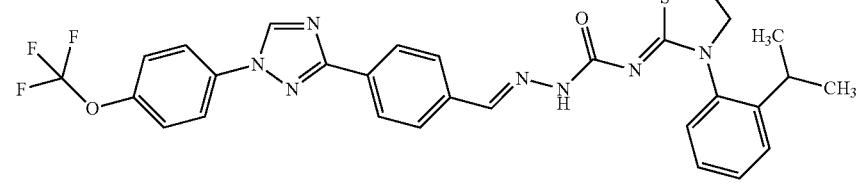 |

| Cmpd. No. | Structure |
|---|---|
| P182 | 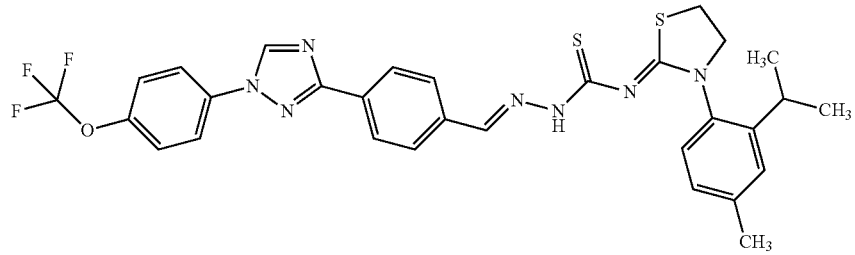 [SMILES: Cc1ccc(N2CCS/C2=N\C(=S)N/N=C/c2ccc(-c3ncn(-c4ccc(OC(F)(F)F)cc4)n3)cc2)c(C(C)C)c1] |
| P183 | 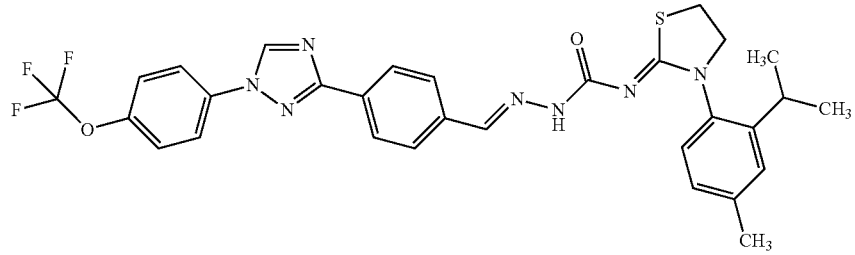 [SMILES: Cc1ccc(N2CCS/C2=N\C(=O)N/N=C/c2ccc(-c3ncn(-c4ccc(OC(F)(F)F)cc4)n3)cc2)c(C(C)C)c1] |
| P184 | 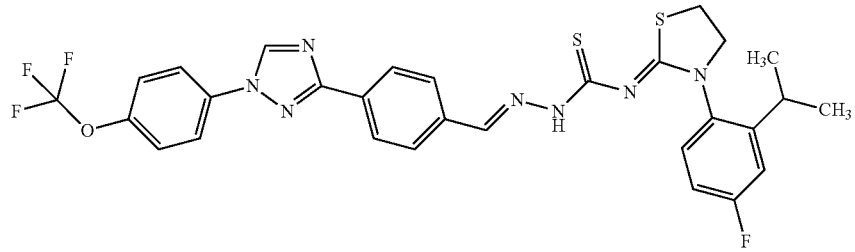 [SMILES: CC(C)c1cc(F)ccc1N1CCS/C1=N\C(=S)N/N=C/c1ccc(-c2ncn(-c3ccc(OC(F)(F)F)cc3)n2)cc1] |
| P185 | 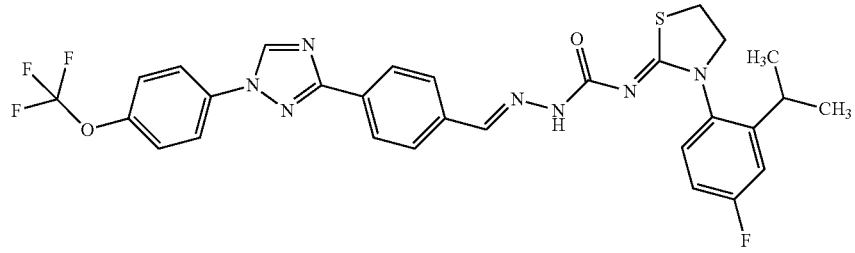 [SMILES: CC(C)c1cc(F)ccc1N1CCS/C1=N\C(=O)N/N=C/c1ccc(-c2ncn(-c3ccc(OC(F)(F)F)cc3)n2)cc1] |
| P186 | 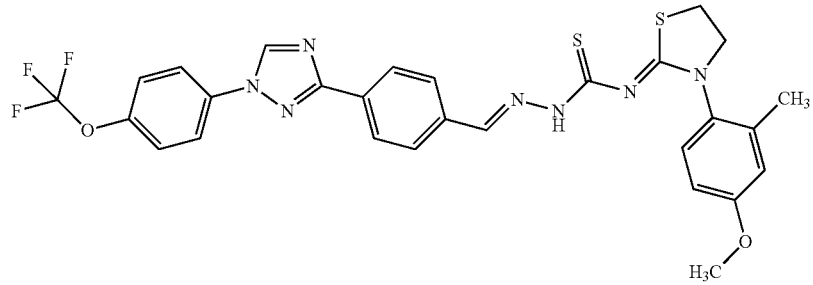 [SMILES: COc1ccc(N2CCS/C2=N\C(=S)N/N=C/c2ccc(-c3ncn(-c4ccc(OC(F)(F)F)cc4)n3)cc2)c(C)c1] |

| Cmpd. No. | Structure |
|---|---|
| P187 | 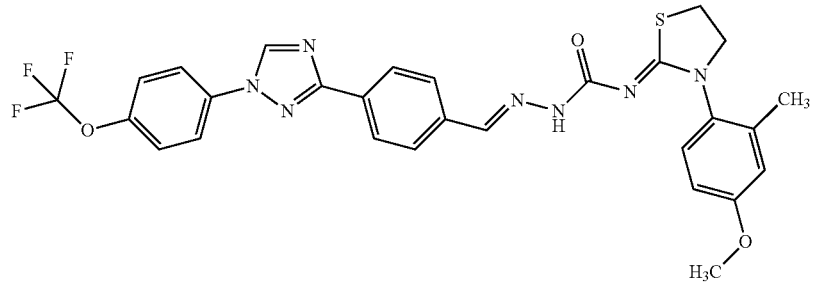 [SMILES: COc1ccc(N2CCS/C2=N\C(=O)N/N=C/c2ccc(-c3ncn(-c4ccc(OC(F)(F)F)cc4)n3)cc2)c(C)c1] |
| P188 | 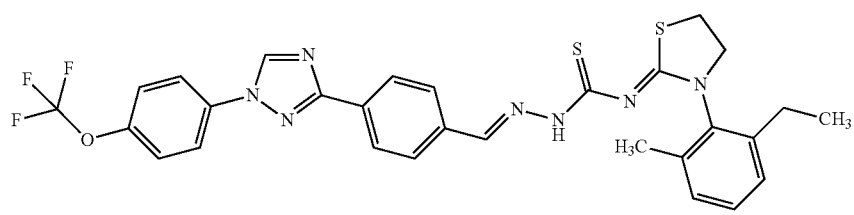 [SMILES: CCc1cccc(C)c1N1CCS/C1=N\C(=S)N/N=C/c1ccc(-c2ncn(-c3ccc(OC(F)(F)F)cc3)n2)cc1] |
| P189 | 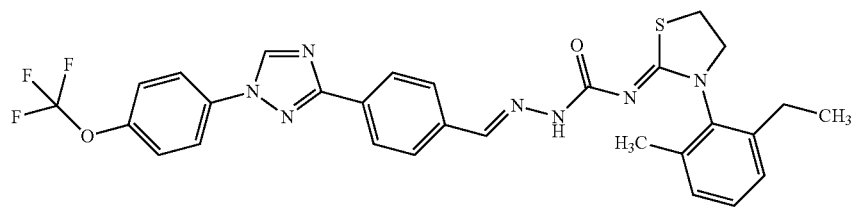 [SMILES: CCc1cccc(C)c1N1CCS/C1=N\C(=O)N/N=C/c1ccc(-c2ncn(-c3ccc(OC(F)(F)F)cc3)n2)cc1] |
| P190 | 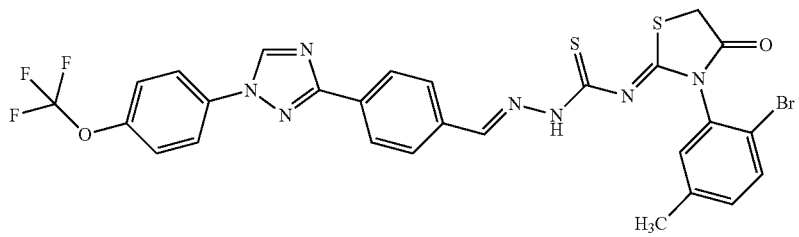 [SMILES: Cc1ccc(Br)c(N2C(=O)CS/C2=N\C(=S)N/N=C/c2ccc(-c3ncn(-c4ccc(OC(F)(F)F)cc4)n3)cc2)c1] |
| P191 | 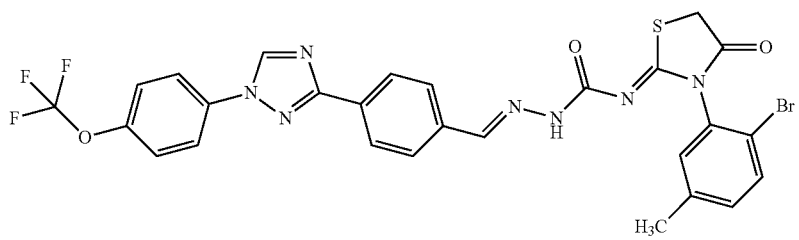 [SMILES: Cc1ccc(Br)c(N2C(=O)CS/C2=N\C(=O)N/N=C/c2ccc(-c3ncn(-c4ccc(OC(F)(F)F)cc4)n3)cc2)c1] |
| P192 | 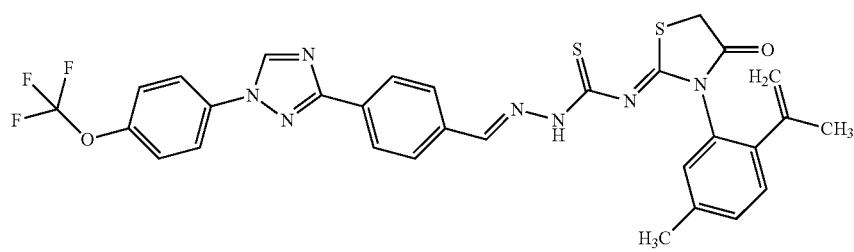 [SMILES: C=C(C)c1ccc(C)cc1N1C(=O)CS/C1=N\C(=S)N/N=C/c1ccc(-c2ncn(-c3ccc(OC(F)(F)F)cc3)n2)cc1] |

| Cmpd. No. | Structure |
|---|---|
| P193 | 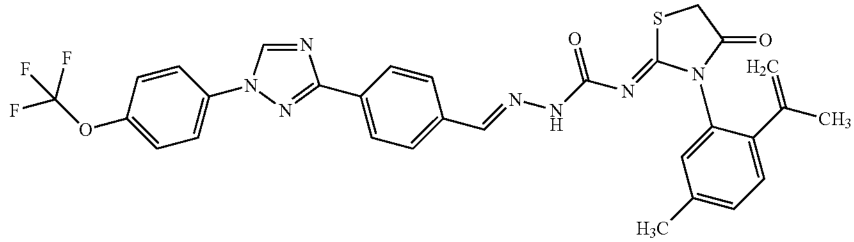 [SMILES: C=C(C)c1ccc(C)cc1N1C(=O)CS/C1=N\C(=O)N/N=C/c1ccc(-c2ncn(-c3ccc(OC(F)(F)F)cc3)n2)cc1] |
| P194 | 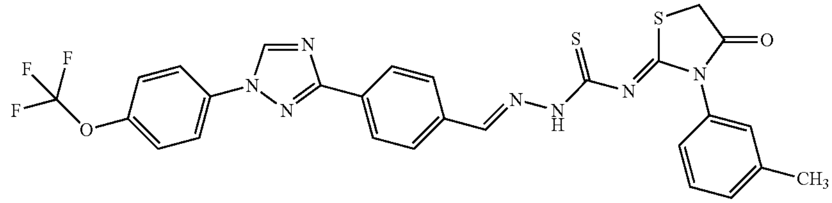 [SMILES: Cc1cccc(N2C(=O)CS/C2=N\C(=S)N/N=C/c2ccc(-c3ncn(-c4ccc(OC(F)(F)F)cc4)n3)cc2)c1] |
| P195 | 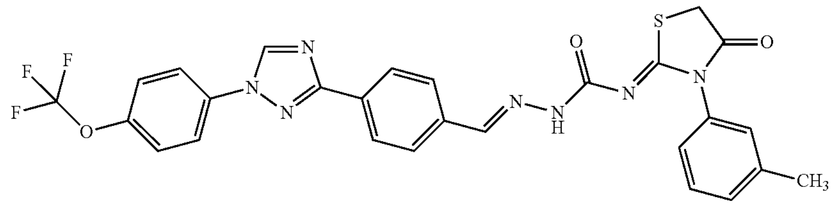 [SMILES: Cc1cccc(N2C(=O)CS/C2=N\C(=O)N/N=C/c2ccc(-c3ncn(-c4ccc(OC(F)(F)F)cc4)n3)cc2)c1] |
| P196 | 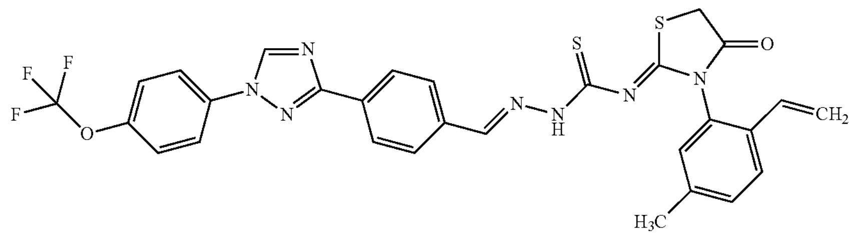 [SMILES: C=Cc1ccc(C)cc1N1C(=O)CS/C1=N\C(=S)N/N=C/c1ccc(-c2ncn(-c3ccc(OC(F)(F)F)cc3)n2)cc1] |
| P197 | 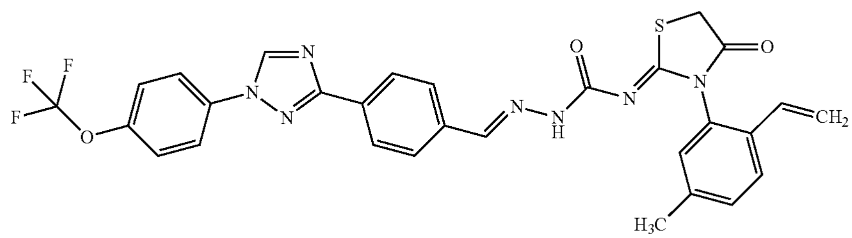 [SMILES: C=Cc1ccc(C)cc1N1C(=O)CS/C1=N\C(=O)N/N=C/c1ccc(-c2ncn(-c3ccc(OC(F)(F)F)cc3)n2)cc1] |
| P198 | 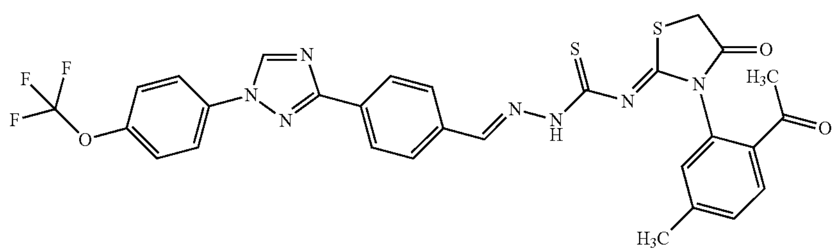 [SMILES: CC(=O)c1ccc(C)cc1N1C(=O)CS/C1=N\C(=O)N/N=C/c1ccc(-c2ncn(-c3ccc(OC(F)(F)F)cc3)n2)cc1] |

-continued

| Cmpd. No. | Structure |
|---|---|
| P199 | 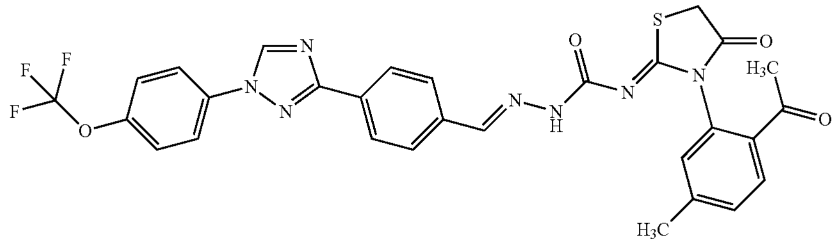 |
| P200 | 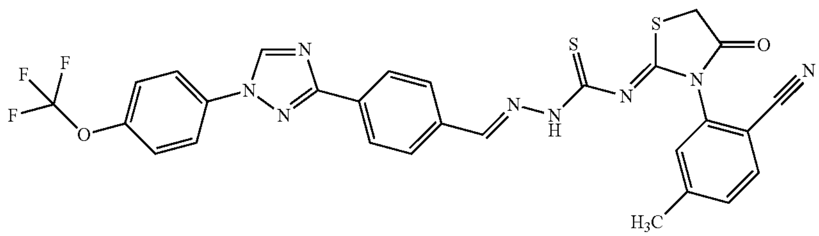 |
| P201 | 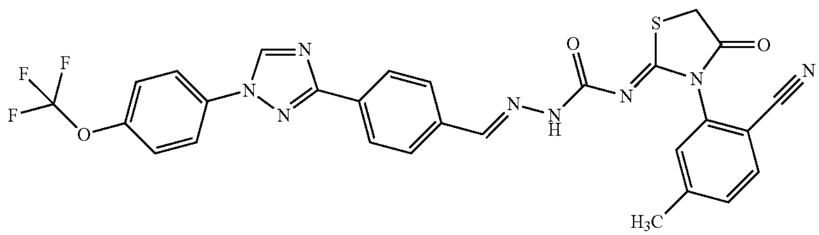 [SMILES: Cc1ccc(C#N)c(N2C(=O)CS/C2=N\C(=O)N/N=C/c2ccc(-c3ncn(-c4ccc(OC(F)(F)F)cc4)n3)cc2)c1] |
| P202 | 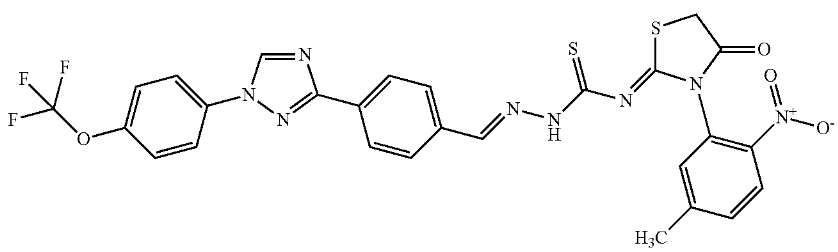 [SMILES: Cc1ccc([N+](=O)[O-])c(N2C(=O)CS/C2=N\C(=S)N/N=C/c2ccc(-c3ncn(-c4ccc(OC(F)(F)F)cc4)n3)cc2)c1] |
| P203 | 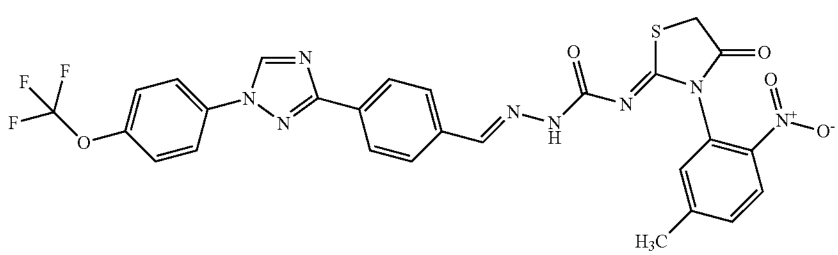 [SMILES: Cc1ccc([N+](=O)[O-])c(N2C(=O)CS/C2=N\C(=O)N/N=C/c2ccc(-c3ncn(-c4ccc(OC(F)(F)F)cc4)n3)cc2)c1] |
| P204 | 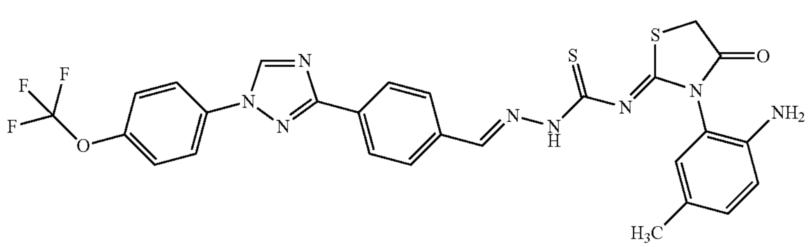 |

| Cmpd. No. | Structure |
|---|---|
| P205 | 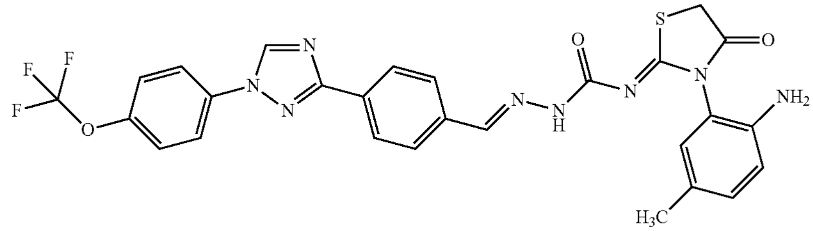 [SMILES: Cc1ccc(N)c(N2C(=O)CS/C2=N\C(=O)N/N=C/c2ccc(-c3ncn(-c4ccc(OC(F)(F)F)cc4)n3)cc2)c1] |
| P206 | 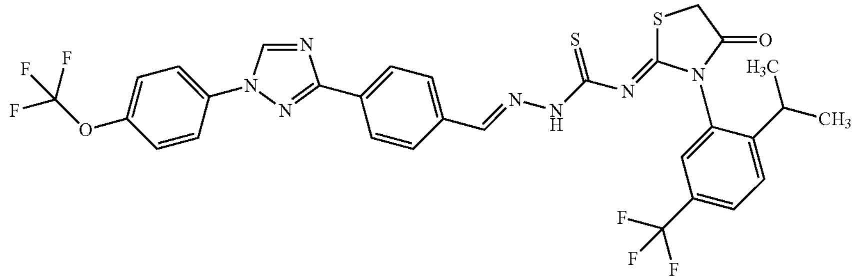 [SMILES: CC(C)c1ccc(C(F)(F)F)cc1N1C(=O)CS/C1=N\C(=S)N/N=C/c1ccc(-c2ncn(-c3ccc(OC(F)(F)F)cc3)n2)cc1] |
| P207 | 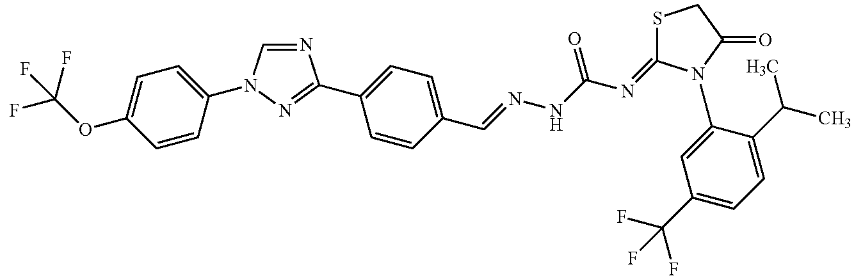 [SMILES: CC(C)c1ccc(C(F)(F)F)cc1N1C(=O)CS/C1=N\C(=O)N/N=C/c1ccc(-c2ncn(-c3ccc(OC(F)(F)F)cc3)n2)cc1] |
| P208 | 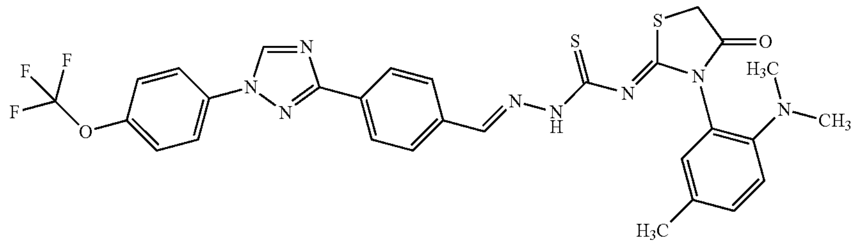 [SMILES: Cc1ccc(N(C)C)c(N2C(=O)CS/C2=N\C(=S)N/N=C/c2ccc(-c3ncn(-c4ccc(OC(F)(F)F)cc4)n3)cc2)c1] |
| P209 | 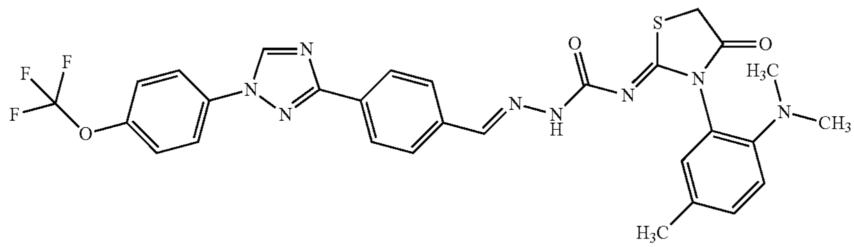 [SMILES: Cc1ccc(N(C)C)c(N2C(=O)CS/C2=N\C(=O)N/N=C/c2ccc(-c3ncn(-c4ccc(OC(F)(F)F)cc4)n3)cc2)c1] |
| P210 | 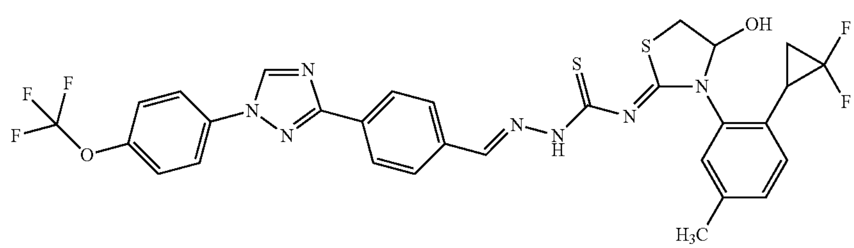 [SMILES: Cc1ccc(C2CC2(F)F)c(N2/C(=N/C(=S)N/N=C/c3ccc(-c4ncn(-c5ccc(OC(F)(F)F)cc5)n4)cc3)SCC2O)c1] |

| Cmpd. No. | Structure |
|---|---|
| P211 | 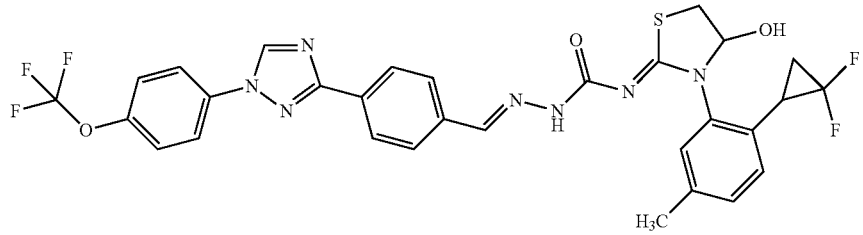 [SMILES: Cc1ccc(C2CC2(F)F)c(N2/C(=N/C(=O)N/N=C/c3ccc(-c4ncn(-c5ccc(OC(F)(F)F)cc5)n4)cc3)SCC2O)c1] |

TABLE 2

Analytical Data for Compounds in Table 1

| Cmpd. No. | Melting Point (° C.) | IR (cm⁻¹) | MASS SPEC | NMR |
|---|---|---|---|---|
| A1 | | | ESIMS m/z 622 ([M + H]$^+$) | $^1$H NMR (400 MHz, CDCl$_3$) δ 8.57 (s, 1H), 8.24-8.16 (m, 2H), 7.95 (d, J = 6.5 Hz, 1H), 7.86-7.76 (m, 4H), 7.39 (td, J = 7.8, 6.5 Hz, 4H), 7.34-7.28 (m, 1H), 6.90 (d, J = 1.2 Hz, 1H), 3.97 (d, J = 2.9 Hz, 2H), 2.66 (p, J = 6.9 Hz, 1H), 2.38 (s, 3H), 1.17 (dd, J = 7.1, 1.3 Hz, 6H); $^{19}$F NMR (376 MHz, CDCl$_3$) δ −58.02 |
| A2 | 116-117 | | ESIMS m/z 608 ([M + H]$^+$) | $^1$H NMR (400 MHz, CDCl$_3$) δ 8.57 (s, 1H), 8.54 (s, 1H), 8.25-8.17 (m, 2H), 7.94 (s, 1H), 7.85-7.77 (m, 4H), 7.54-7.47 (m, 2H), 7.43-7.32 (m, 3H), 7.09 (dt, J = 8.3, 0.7 Hz, 1H), 3.99 (d, J = 2.4 Hz, 2H), 2.70 (hept, J = 6.8 Hz, 1H), 1.20 (dd, J = 6.9, 0.9 Hz, 6H); $^{19}$F NMR (376 MHz, CDCl$_3$) δ −58.02 |
| A3 | 119-120 | | ESIMS m/z 608 ([M + H]$^+$) | $^1$H NMR (400 MHz, CDCl$_3$) δ 8.57 (s, 2H), 8.24-8.18 (m, 2H), 7.93 (s, 1H), 7.85-7.77 (m, 4H), 7.43-7.33 (m, 4H), 7.25-7.18 (m, 1H), 3.99 (s, 2H), 2.44 (q, J = 7.5 Hz, 2H), 2.14 (s, 3H), 1.18 (t, J = 7.6 Hz, 3H); $^{19}$F NMR (376 MHz, CDCl$_3$) δ −58.02 |
| A4 | | | ESIMS m/z 614 ([M + H]$^+$) | $^1$H NMR (400 MHz, CDCl$_3$) δ 8.59 (s, 1H), 8.57 (s, 1H), 8.25-8.16 (m, 2H), 7.95 (s, 1H), 7.85-7.77 (m, 4H), 7.45 (d, J = 8.3 Hz, 1H), 7.39 (dq, J = 9.0, 1.0 Hz, 2H), 7.30-7.22 (m, 1H), 7.10 (dd, J = 2.1, 0.9 Hz, 1H), 4.08-3.86 (m, 2H), 2.41 (s, 3H); $^{19}$F NMR (376 MHz, CDCl$_3$) δ −58.02 |
| A5 | | | ESIMS m/z 624 ([M + H]$^+$) | $^1$H NMR (400 MHz, CDCl$_3$) δ 8.71 (s, 1H), 8.57 (s, 1H), 8.23-8.16 (m, 2H), 7.90 (s, 1H), 7.83-7.77 (m, 4H), 7.44-7.36 (m, 2H), 7.23 (ddd, J = 8.5, 2.2, 0.8 Hz, 1H), 6.99 (dd, J = 2.2, 0.8 Hz, 1H), 6.93 (d, J = 8.4 Hz, 1H), 4.02 (q, J = 7.0 Hz, 2H), 3.93 (d, J = 6.8 Hz, 2H), 2.34 (s, 3H), 1.30 (t, J = 7.0 Hz, 3H); $^{19}$F NMR (376 MHz, CDCl$_3$) δ −58.02 |
| A6 | | | ESIMS m/z 678 ([M + H]$^+$) | $^1$H NMR (400 MHz, CDCl$_3$) δ 8.57 (s, 1H), 8.56 (s, 1H), 8.24-8.17 (m, 2H), 7.96 (s, 1H), 7.86-7.77 (m, 4H), 7.44-7.35 (m, 2H), 7.29 (ddd, J = 8.5, 2.1, 0.8 Hz, 1H), 7.10-7.03 (m, 1H), 6.98 (d, J = 8.4 Hz, 1H), 4.44-4.26 (m, 2H), 3.94 (d, J = 5.9 Hz, 2H), 2.39 (s, 3H); $^{19}$F NMR (376 MHz, CDCl$_3$) δ −58.02, −74.09 |
| A7 | | | ESIMS m/z 610 ([M + H]$^+$) | $^1$H NMR (400 MHz, CDCl$_3$) δ 8.62 (s, 1H), 8.57 (s, 1H), 8.26-8.17 (m, 2H), 7.93 (s, 1H), 7.85-7.77 (m, 4H), |

TABLE 2-continued

Analytical Data for Compounds in Table 1

| Cmpd. No. | Melting Point (° C.) | IR (cm$^{-1}$) | MASS SPEC | NMR |
|---|---|---|---|---|
| | | | | 7.42-7.36 (m, 2H), 7.05 (d, J = 8.3 Hz, 1H), 6.90-6.84 (m, 2H), 3.96 (d, J = 0.9 Hz, 2H), 3.85 (s, 3H), 2.14 (s, 3H); $^{19}$F NMR (376 MHz, CDCl$_3$) δ −58.02 |
| A8 | | | ESIMS m/z 610 ([M + H]$^+$) | $^1$H NMR (400 MHz, CDCl$_3$) δ 8.70 (s, 1H), 8.56 (s, 1H), 8.24-8.16 (m, 2H), 7.89 (s, 1H), 7.85-7.74 (m, 4H), 7.46-7.34 (m, 3H), 7.18 (dd, J = 7.7, 1.7 Hz, 1H), 7.11-6.97 (m, 2H), 4.05 (q, J = 7.0 Hz, 2H), 3.92 (d, J = 6.9 Hz, 2H), 1.31 (t, J = 7.0 Hz, 3H); $^{19}$F NMR (376 MHz, CDCl$_3$) δ −58.01 |
| A9 | | | ESIMS m/z 648 ([M + H]$^+$) | $^1$H NMR (400 MHz, CDCl$_3$) δ 8.59 (s, 1H), 8.57 (s, 1H), 8.22-8.16 (m, 2H), 7.94 (s, 1H), 7.83-7.77 (m, 4H), 7.70 (d, J = 8.1 Hz, 1H), 7.43 (ddt, J = 8.0, 1.7, 0.9 Hz, 1H), 7.39 (dt, J = 7.9, 1.0 Hz, 2H), 7.11 (s, 1H), 4.09-3.83 (m, 2H), 2.57-2.37 (m, 3H); $^{19}$F NMR (376 MHz, CDCl$_3$) δ −58.02, −61.12 |

Example 3: Bioassays

Insecticidal Test for Beet Armyworm (*Spodoptera exigua*, LAPHEG) ("BAW")

Bioassays on beet armyworm (BAW; *Spodoptera exigua*: Lepidoptera) are conducted using a 128-well diet tray assay. One to five second instar BAW larvae are placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays are covered with a clear self-adhesive cover, vented to allow gas exchange, and held at 25° C., 14:10 light-dark for five to seven days. Percent mortality is recorded for the larvae in each well; activity in the eight wells is then averaged. The results are indicated in Table 3.

Insecticidal Test for Cabbage Looper (*Trichloplusia ni*, TRIPNI) ("CL")

Bioassays on cabbage looper (CL; *Trichloplusia ni*: Lepidoptera) are conducted using a 128-well diet tray assay. One to five second instar CL larvae are placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays are covered with a clear self-adhesive cover, vented to allow gas exchange, and held at 25° C., 14:10 light-dark for five to seven days. Percent mortality is recorded for the larvae in each well; activity in the eight wells is then averaged. The results are indicated in Table 3.

Insecticidal Test for Yellow Fever Mosquito (*Aedes aegypti*, AEDSAE) ("YFM")

Master plates containing 400 μg of a molecule dissolved in 100 μL of dimethyl sulfoxide (DMSO) (equivalent to a 4000 ppm solution) are used. A master plate of assembled molecules contains 15 μL per well. To this plate, 135 μL of a 90:10 water/acetone mixture is added to each well. A robot (Biomek® NXP Laboratory Automation Workstation) is programmed to dispense 15 μL aspirations from the master plate into an empty 96-well shallow plate ("daughter" plate). There are 6 reps ("daughter" plates) created per master. The created "daughter" plates are then immediately infested with YFM larvae.

The day before plates are to be treated, mosquito eggs are placed in Millipore water containing liver powder to begin hatching (4 g. into 400 mL). After the "daughter" plates are created using the robot, they are infested with 220 μL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality. The results are indicated in Table 3.

| % Control (or Mortality) | Rating |
|---|---|
| BAW & CEW Rating Table | |
| 50-100 | A |
| More than 0-Less than 50 | B |
| Not Tested | C |
| No activity noticed in this bioassay | D |
| YFM Rating Table | |
| 80-100 | A |
| More than 0-Less than 80 | B |
| Not Tested | C |
| No activity noticed in this bioassay | D |

TABLE 3

Bioassay Activities of Compounds

| Compound | BAW % Control | CL % Control | YFM % Control |
|---|---|---|---|
| A1 | A | A | C |
| A2 | A | A | A |
| A3 | A | A | C |
| A4 | A | A | A |
| A5 | A | A | C |
| A6 | A | A | C |
| A7 | A | A | A |

TABLE 3-continued

Bioassay Activities of Compounds

| Compound | BAW % Control | CL % Control | YFM % Control |
|---|---|---|---|
| A8 | A | A | C |
| A9 | A | A | C |

We claim:
1. A compound having the structure of Formula One:

Formula One

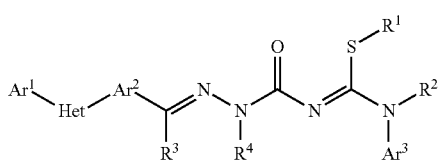

wherein:
(a) Ar$^1$ is a phenyl or substituted phenyl having one or more substituents independently selected from $C_1$-$C_6$ alkyl, $C_1$-$C_6$ haloalkyl, and $C_1$-$C_6$ haloalkoxy;
(b) Het is a triazolyl, imidazolyl, pyrrolyl, or pyrazolyl;
(c) Ar$^2$ is a phenyl or a substituted phenyl having one or more substituents independently selected from $C_1$-$C_6$ alkyl, $C_1$-$C_6$ haloalkyl, and $C_1$-$C_6$ haloalkoxy;
(d) R$^3$ and R$^4$ are each independently selected from H, F, Cl, $C_1$-$C_6$ alkyl, $C_1$-$C_6$ alkoxy, $C_1$-$C_6$ haloalkyl, $C_1$-$C_6$ haloalkoxy, phenyl, or phenoxy;
R$^1$ and R$^2$ together form a 5- to 7-membered ring containing one or more C=O, C=S, N, S or O, and such ring is optionally substituted with OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, phenyl, or phenoxy, wherein said phenyl or phenoxy is optionally substituted with one or more OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, or phenyl; and
(e) Ar$^3$ is a phenyl optionally substituted with one or more substituents independently selected from OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, phenyl, or phenoxy.

2. The compound of claim 1, wherein Ar$^1$ is a substituted phenyl having one or more substituents independently selected from $OCF_3$, $OCF_2CF_3$, and $CF_3$.

3. The compound of claim 1, wherein Het is 1,2,4-triazolyl.

4. The compound of claim 1, wherein Ar$^2$ is a phenyl.

5. The compound of claim 1, wherein Ar$^2$ is a substituted phenyl having one or more substituents independently selected from $OCF_3$, $OCF_2CF_3$, and $CF_3$.

6. The compound of claim 1, wherein R$^1$ and R$^2$ together form a 5-membered ring containing one or two C=O, and such ring is optionally substituted with OH, F, Cl, Br, I, CN, $C_1$-$C_6$ alkyl, $C_1$-$C_6$ haloalkyl, $C_1$-$C_6$ alkoxy, $C_1$-$C_6$ haloalkoxy, phenyl or phenoxy.

7. The compound of claim 1, wherein each of R$^3$ and R$^4$ is independently H, F, Cl, or a $C_1$-$C_6$ alkyl.

8. The compound of claim 1, wherein Ar$^3$ is a substituted phenyl with one or more OH, F, Cl, Br, I, $C_1$-$C_6$ alkyl, $C_1$-$C_6$ haloalkyl, $C_1$-$C_6$ hydroxyalkyl, $C_1$-$C_6$ alkoxy, or $C_1$-$C_6$ haloalkoxy.

9. The compound of claim 1 having a structure selected from compounds listed in Table 1

A1

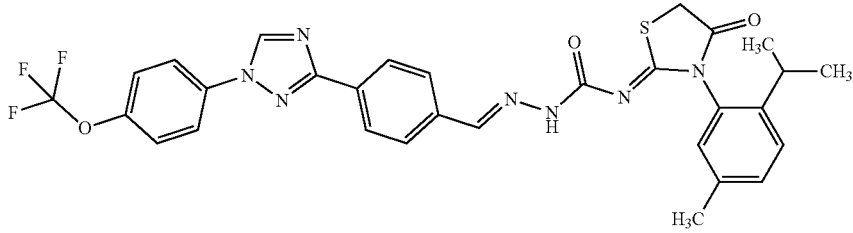 [SMILES: Cc1ccc(C(C)C)c(N2C(=O)CS/C2=N\C(=O)N/N=C/c2ccc(-c3ncn(-c4ccc(OC(F)(F)F)cc4)n3)cc2)c1]

A2

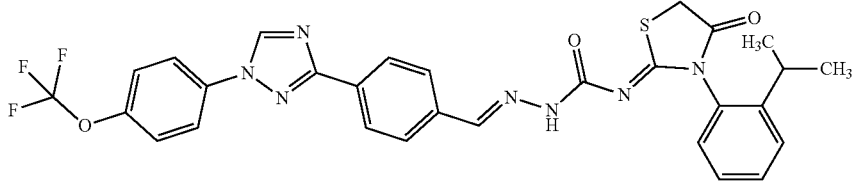 [SMILES: CC(C)c1ccccc1N1C(=O)CS/C1=N\C(=O)N/N=C/c1ccc(-c2ncn(-c3ccc(OC(F)(F)F)cc3)n2)cc1]

A3

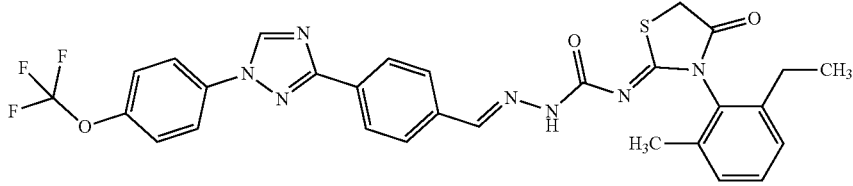 [SMILES: CCc1cccc(C)c1N1C(=O)CS/C1=N\C(=O)N/N=C/c1ccc(-c2ncn(-c3ccc(OC(F)(F)F)cc3)n2)cc1]

A4 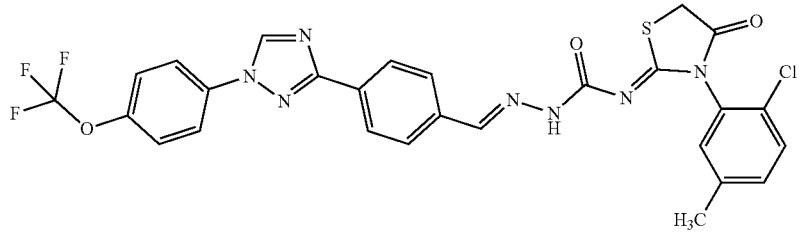 [SMILES: Cc1ccc(Cl)c(N2C(=O)CS/C2=N\C(=O)N/N=C/c2ccc(-c3ncn(-c4ccc(OC(F)(F)F)cc4)n3)cc2)c1]
A5 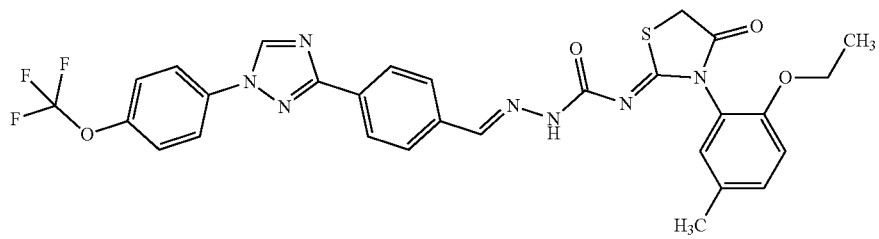 [SMILES: CCOc1ccc(C)cc1N1C(=O)CS/C1=N\C(=O)N/N=C/c1ccc(-c2ncn(-c3ccc(OC(F)(F)F)cc3)n2)cc1]
A6 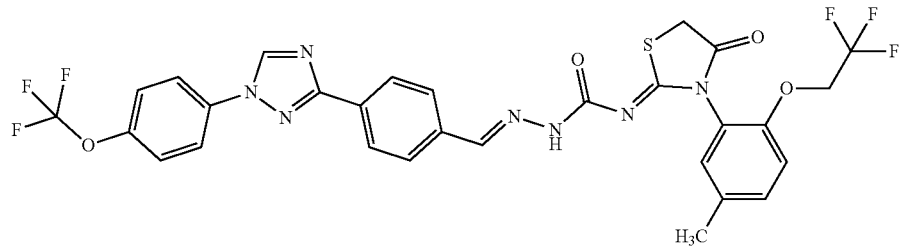 [SMILES: Cc1ccc(OCC(F)(F)F)c(N2C(=O)CS/C2=N\C(=O)N/N=C/c2ccc(-c3ncn(-c4ccc(OC(F)(F)F)cc4)n3)cc2)c1]
A7 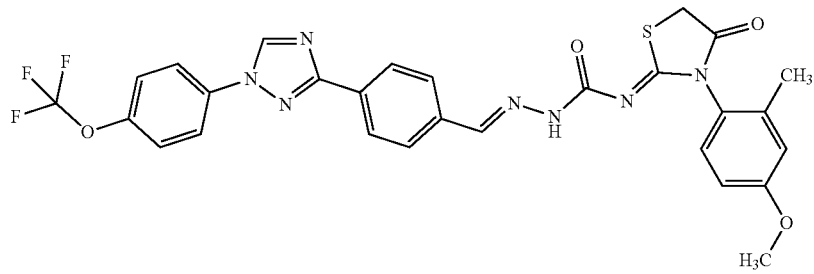 [SMILES: COc1ccc(N2C(=O)CS/C2=N\C(=O)N/N=C/c2ccc(-c3ncn(-c4ccc(OC(F)(F)F)cc4)n3)cc2)c(C)c1]
A8 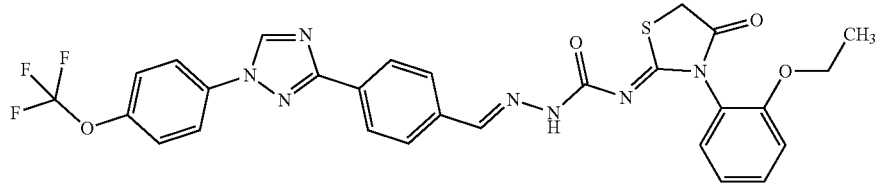 [SMILES: CCOc1ccccc1N1C(=O)CS/C1=N\C(=O)N/N=C/c1ccc(-c2ncn(-c3ccc(OC(F)(F)F)cc3)n2)cc1]
A9 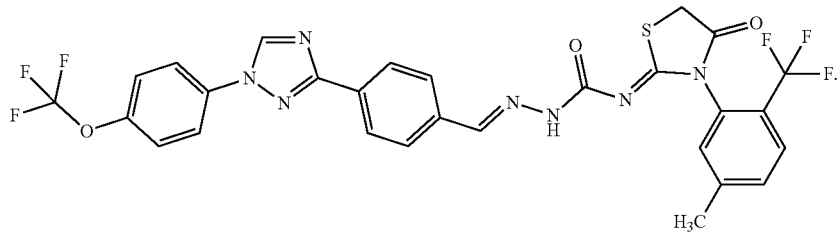 [SMILES: Cc1ccc(C(F)(F)F)c(N2C(=O)CS/C2=N\C(=O)N/N=C/c2ccc(-c3ncn(-c4ccc(OC(F)(F)F)cc4)n3)cc2)c1]
10. A process to control a pest comprising applying a compound of claim 3 to an area to control a pest in an amount sufficient to control such pest.
11. A process according to claim 10 wherein said pest is beet armyworm (BAW), cabbage looper (CL), or yellow fever mosquito (YFM).

12. A compound that is a pesticidally acceptable acid addition salt, a salt derivative, a solvate, or an ester derivative, of a molecule according to claim 1.

13. A compound according to claim 1 wherein at least one H is $^2$H or at least one C is $^{14}$C.

14. A composition comprising a compound according to claim 1 and at least one other compound having insecticidal, herbicidal, acaricidal, nematicidal, or fungicidal activity.

15. A composition comprising a compound according to claim 1 and a seed.

16. A process of using the compound of formula I comprising applying the compound to a genetically modified plant, or genetically-modified seed, which has been genetically modified to express one or more specialized traits.

17. A process of using the compound of formula I comprising: orally administering; or topically applying; the compound, to a non-human animal, to control endoparasites, ectoparasites, or both.

* * * * *